(12) United States Patent
Huang et al.

(10) Patent No.: US 11,701,342 B2
(45) Date of Patent: Jul. 18, 2023

(54) CO-THERAPIES INCLUDING A METASTASIS INHIBITOR

(71) Applicants: NOVITA PHARMACEUTICALS, INC., New York, NY (US); CORNELL UNIVERSITY, Ithaca, NY (US)

(72) Inventors: Xin-Yun Huang, New York, NY (US); Jue Jillian Zhang, New York, NY (US); Christy Young Shue, Towaco, NJ (US)

(73) Assignees: CORNELL UNIVERSITY, Ithaca, NY (US); NOVITA PHARMACEUTICALS, INC., New York, NY (US)

( * ) Notice: Subject to any disclaimer, the term of this patent is extended or adjusted under 35 U.S.C. 154(b) by 254 days.

(21) Appl. No.: 16/766,156

(22) PCT Filed: Nov. 20, 2018

(86) PCT No.: PCT/US2018/062069
§ 371 (c)(1),
(2) Date: May 21, 2020

(87) PCT Pub. No.: WO2019/104067
PCT Pub. Date: May 31, 2019

(65) Prior Publication Data
US 2020/0352911 A1    Nov. 12, 2020

Related U.S. Application Data

(60) Provisional application No. 62/590,067, filed on Nov. 22, 2017.

(51) Int. Cl.
*A61K 31/4162* (2006.01)
*A61K 31/337* (2006.01)
(Continued)

(52) U.S. Cl.
CPC ........ *A61K 31/4162* (2013.01); *A61K 31/337* (2013.01); *A61K 31/501* (2013.01);
(Continued)

(58) Field of Classification Search
CPC .............. A61K 2300/00; A61K 31/337; A61K 31/416; A61K 31/422; A61K 31/427;
(Continued)

(56) References Cited

U.S. PATENT DOCUMENTS

2006/0263362 A1   11/2006   Ochiai et al.
2008/0200458 A1    8/2008   Barbosa et al.
(Continued)

FOREIGN PATENT DOCUMENTS

WO    WO-2015/127125 A1    8/2015

OTHER PUBLICATIONS

Perez (The oncologist 1998:3, pp. 373-389) (Year: 1998).*
(Continued)

*Primary Examiner* — Savitha M Rao
(74) *Attorney, Agent, or Firm* — Foley & Lardner LLP

(57) ABSTRACT

Provided are methods of increasing a response to a chemotherapeutic agent or an immunotherapeutic agent in a patient in need thereof, and methods of treating cancer in a patient in need thereof, comprising administering to the patient a chemotherapeutic agent or an immunotherapeutic agent and a metastasis inhibiting compound, as described in this disclosure.

11 Claims, 3 Drawing Sheets

(51) Int. Cl.
  *A61K 31/501* (2006.01)
  *A61K 31/675* (2006.01)
  *A61K 31/704* (2006.01)
  *C07K 16/28* (2006.01)
  *A61P 35/00* (2006.01)
  *A61K 45/06* (2006.01)

(52) U.S. Cl.
  CPC .......... *A61K 31/675* (2013.01); *A61K 31/704* (2013.01); *A61K 45/06* (2013.01); *A61P 35/00* (2018.01); *C07K 16/2818* (2013.01)

(58) Field of Classification Search
  CPC .. A61K 31/501; A61K 31/675; A61K 31/704; A61K 39/39541; A61K 2039/505; A61K 31/4162; A61K 45/06; A61P 35/00; C07D 403/12; C07D 405/12; C07D 413/12; C07D 417/12; C07K 16/2818
  See application file for complete search history.

(56) References Cited

U.S. PATENT DOCUMENTS

2014/0037551 A1  2/2014  Zang et al.
2015/0299191 A1  10/2015  Huang et al.
2015/0374860 A1  12/2015  O'Neill et al.

OTHER PUBLICATIONS

Extended Search Report on EP 18880764.8 dated Jul. 6, 2021 (10 pages).
Han, et al., "Improving fascin inhibitors to block tumor cell migration and metastasis", Molecular Oncology 10(7): 966-980 (2016).
International Preliminary Report on Patentability on PCT/US2018/062069 dated Jun. 4, 2020 (8 pages).
Lee, et al., "Synthesis and anti-proliferative activity evaluation of N3-acyl-N5-aryl-3,5-diaminoindazole analogues as anti-head and neck cancer agent", DARU Journal of Pharmaceutical Sciences 22(1): 9 pages (2014).
International Search Report and Written Opinion, issued in International Application No. PCT/US2018/062069, 16 pages (dated Feb. 4, 2019).
Flynn et al., "Novel combination strategies for enhancing efficacy of immune checkpoint inhibitors in the treatment of metastatic solid malignancies", Expert Opinion on Pharmacotherapy, 2017, vol. 18, No. 14, pp. 1477-1490.
Ghebeh et al., "Fascin is involved in the chemotherapeutic resistance of breast cancer cells predominantly via the PI3K/Akt pathway", British Journal of Cancer, 111.8 (2014): 1552-1561.

* cited by examiner

CO-THERAPIES INCLUDING A METASTASIS INHIBITOR

CROSS-REFERENCE TO RELATED APPLICATIONS

The present application is the U.S. National Stage of PCT/US2018/062069, filed Nov. 20, 2018, which claims priority on U.S. Provisional Application No. 62/590,067, filed on Nov. 22, 2017, the content of which is incorporated herein by reference.

FIELD

The present technology relates generally to compounds, compositions and methods for treating or preventing cancer.

BACKGROUND

Tumor metastasis is the major cause of mortality of cancer patients. Inhibition of tumor metastasis will significantly increase the survival rate of cancer patients. Metastasis is a multi-step process wherein a primary tumor spreads from its initial site to secondary tissues/organs. Weiss, L. Metastasis of cancer: a conceptual history from antiquity to the 1990s. *Cancer Metastasis Rev* 19, I-XI, 193-383 (2000); Fidler, I. J. The pathogenesis of cancer metastasis: the 'seed and soil' hypothesis revisited. *Nat Rev Cancer* 3, 453-458 (2003); Valastyan, S. & Weinberg, R. A. Tumor metastasis: molecular insights and evolving paradigms. *Cell* 147, 275-292, (2011). Tumor cell migration and organ invasion are critical steps in metastasis. ndeelis, J., Singer, R. H. & Segall, J. E. The great escape: when cancer cells hijack the genes for chemotaxis and motility. *Annu Rev Cell Dev Biol* 21, 695-718 (2005). Migration provides tumor cells the ability to leave the primary tumor bed (local invasion), enter into blood vessels, and then exit the circulation and infiltrate distant tissues/organs. There have been important new insights into the biology of local tumor growth, and these are being exploited as new targets for treatment. But it is critical also to understand and interrupt the process of tumor metastasis as that is ultimately the terminal event leading to cancer mortality.

For cell migration and invasion to proceed, actin cytoskeleton must be reorganized by forming polymers and bundles to cause dynamic changes in cell shapes. Id.; Mogilner, A. & Rubinstein, B. The physics of filopodial protrusion. *Biophys J* 89, 782-795 (2005); Pollard, T. D. & Cooper, J. A. Actin, a central player in cell shape and movement. *Science* 326, 1208-1212, (2009). Among the morphological structures supported by actin filaments, one of the most prominent protrusive organelles is filopodia which are fundamental to cell shape and motility events. Manila, P. K. & Lappalainen, P. Filopodia: molecular architecture and cellular functions. *Nat Rev Mol Cell Biol* 9, 446-454, (2008). Filopodia are finger-like plasma membrane protrusions that are formed upon remodeling of the actin cytoskeleton beneath the plasma membrane. They can be viewed as a sensory organ of the cells that are used to detect and assimilate signals as well as to explore and move into the surrounding microenvironment. avenport, R. W., Dou, P., Rehder, V. & Kater, S. B. A sensory role for neuronal growth cone filopodia. *Nature* 361, 721-724, doi:10.1038/361721a0 (1993); Bentley, D. & Toroian-Raymond, A. Disoriented pathfinding by pioneer neurone growth cones deprived of filopodia by cytochalasin treatment. *Nature* 323, 712-715, doi:10.1038/323712a0 (1986); Sanders, T. A., Llagostera, E. & Barna, M. Specialized filopodia direct long-range transport of SHH during vertebrate tissue patterning. *Nature* 497, 628-632, doi:10.1038/nature12157 (2013). They contain long actin filaments crosslinked into parallel bundles by the fascin protein. Metastatic tumor cells are rich in filopodia, and the numbers of filopodia correlate with their invasiveness. Filopodia-like protrusions have also been shown to be critical for metastatic tumor cells to interact with the metastatic microenvironment and to grow at the secondary tissues. ue, T., Brooks, M. W., Inan, M. F., Reinhardt, F. & Weinberg, R. A. The outgrowth of micrometastases is enabled by the formation of filopodium-like protrusions. *Cancer discovery* 2, 706-721 (2012).

Fascin is the main actin cross-linker in filopodia and shows no amino acid sequence homology with other actin-binding proteins. to, J. J., Kane, R. E. & Bryan, J. Formation of filopodia in coelomocytes: localization of fascin, a 58,000 dalton actin cross-linking protein. *Cell* 17, 285-293 (1979); Bryan, J. & Kane, R. E. Separation and interaction of the major components of sea urchin actin gel. *J Mol Biol* 125, 207-224 (1978); Yamashiro-Matsumura, S. & Matsumura, F. Purification and characterization of an F-actin-bundling 55-kilodalton protein from HeLa cells. *J Biol Chem* 260, 5087-5097 (1985); Vignjevic, D. et al. Formation of filopodia-like bundles in vitro from a dendritic network. *J Cell Biol* 160, 951-962 (2003); Vignjevic, D. et al. Role of fascin in filopodial protrusion. *J Cell Biol* 174, 863-875 (2006); Adams, J. C. Roles of fascin in cell adhesion and motility. *Curr Opin Cell Biol* 16, 590-596 (2004). It has a molecular mass of ~55 kDa and functions as a monomer. It fastens 10-30 parallel actin filaments together into straight, compact, and rigid bundles, to form filopodia (60-200 nm in diameter) and to impart distinct mechanical stiffness to actin bundles. Tilney, L. G., Connelly, P. S., Vranich, K. A., Shaw, M. K. & Guild, G. M. Why are two different cross-linkers necessary for actin bundle formation in vivo and what does each cross-link contribute? *J Cell Biol* 143, 121-133 (1998); Claessens, M. M., Bathe, M., Frey, E. & Bausch, A. R. Actin-binding proteins sensitively mediate F-actin bundle stiffness. *Nat Mater* 5, 748-753 (2006). When ectopically expressed in tumor cells, fascin promotes tumor cell migration, invasion and metastasis. himoto, Y., Kim, D. J. & Adams, J. C. The roles of fascins in health and disease. *The Journal of pathology* 224, 289-300 (2011). It has been suggested that up-regulation of fascin is part of the program of epithelial-to-mesenchymal transition that confers motility and invasion properties on tumor cells. Machesky, L. M. & Li, A. Fascin: Invasive filopodia promoting metastasis. *Commun Integr Biol* 3, 263-270 (2010).

Studies on samples from human cancer patients demonstrate that fascin is a biomarker of metastases and that fascin is a good therapeutic target. Darnel, A. D. et al. Fascin regulates prostate cancer cell invasion and is associated with metastasis and biochemical failure in prostate cancer. *Clin Cancer Res* 15, 1376-1383, doi:15/4/1376 [pii]10.1158/1078-0432.CCR-08-1789 (2009); Pelosi, G. et al. Independent value of fascin immunoreactivity for predicting lymph node metastases in typical and atypical pulmonary carcinoids. *Lung cancer* 42, 203-213 (2003); Hashimoto, Y., Shimada, Y., Kawamura, J., Yamasaki, S. & Imamura, M. The prognostic relevance of fascin expression in human gastric carcinoma. *Oncology* 67, 262-270 (2004); Cao, D., Ji, H. & Ronnett, B. M. Expression of mesothelin, fascin, and prostate stem cell antigen in primary ovarian mucinous tumors and their utility in differentiating primary ovarian mucinous tumors from metastatic pancreatic mucinous carcinomas in the ovary. *Int J Gynecol Pathol* 24, 67-72 (2005);

Rodriguez-Pinilla, S. M. et al. Prognostic significance of basal-like phenotype and fascin expression in node-negative invasive breast carcinomas. *Clin Cancer Res* 12, 1533-1539 (2006). Elevated levels of fascin have been found in many types of metastatic tumors and are correlated with clinically aggressive phenotypes, poor prognosis, and shorter survival. Tan, V. Y., Lewis, S. J., Adams, J. C. & Martin, R. M. Association of fascin-1 with mortality, disease progression and metastasis in carcinomas: a systematic review and meta-analysis. *BMC Med* 11, 52 (2013). Human fascin expression is low or absent in normal adult epithelial cells, but highly expressed in metastatic tumors. rothey, A., Hashizume, R., Sahin, A. A. & McCrea, P. D. Fascin, an actin-bundling protein associated with cell motility, is upregulated in hormone receptor negative breast cancer. *Br J Cancer* 83, 870-873 (2000); Hashimoto, Y., Skacel, M. & Adams, J. C. Roles of fascin in human carcinoma motility and signaling: prospects for a novel biomarker? *The international journal of biochemistry & cell biology* 37, 1787-1804 (2005). A systematic review and meta-analysis of 26 immunohistochemical studies (total ~9,000 cancer patients) revealed that high fascin levels are associated with increased risk of mortality, lymph node metastasis, distant metastasis, and disease progression, and may provide a novel biomarker for early identification of aggressive and metastatic tumors. Furthermore, another systematic review and meta-analysis of 73 immunohistochemical studies (total 5,000 cancer patients) uncovered several biomarkers, including fascin, prognostic of overall survival. Ruys, A. T. et al. Prognostic Biomarkers in Patients with Resected Cholangiocarcinoma: A Systematic Review and Meta-analysis. *Annals of surgical oncology* 21, 487-500, doi:10.1245/s10434-013-3286-x (2014). Moreover, studies from 122 pancreatic cancer patients showed that higher levels of fascin correlate with poor outcome, time to recurrence and decreased overall survival. Li, A. et al. Fascin is regulated by slug, promotes progression of pancreatic cancer in mice, and is associated with patient outcomes. *Gastroenterology* 146, 1386-1396 (2014). Taken together, these data from human cancer patients may suggest a role for fascin in cancer progression and metastasis.

Mouse genetic studies have shown that fascin gene-knockout mice are normal, likely due to the functional compensation of other actin-bundling proteins during embryonic development. Yamakita, Y., Matsumura, F. & Yamashiro, S. Fascin1 is dispensable for mouse development but is favorable for neonatal survival. *Cell Motil Cytoskeleton* 66, 524-534 (2009).

Cancer immunotherapy with checkpoint inhibitors has made a significant impact on the treatment of many types of cancer. Sharma, P. & Allison, J. P. The future of immune checkpoint therapy. *Science* 348, 56-61 (2015). When successful, immunotherapy (such as antibody inhibitors for cytotoxic T-lymphocyte antigen 4 (CTLA-4) or programmed cell death-1 (PD-1)) extends patient's lives for months or years longer than chemotherapy and radiotherapy. However, only ~25-30% of patients derive a benefit from immunotherapy, and immunotherapy is known to produce significant immune-related side-effects for some patients.

Thus, a need exists for new methods of treatment that improve upon current cancer treatment methods.

SUMMARY

Embodiments disclosed herein include a method of increasing a response to a chemotherapeutic agent or an immunotherapeutic agent in a patient in need thereof, comprising: administering to the patient a compound represented by formula (I):

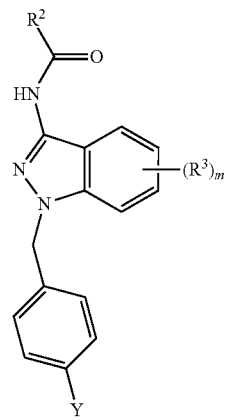

or tautomer thereof, and/or a pharmaceutically acceptable salt thereof; wherein $R^2$ is 6- to 10-membered aryl or 5- to 10-membered heteroaryl; wherein the 6- to 10-membered aryl or 5- to 10-membered heteroaryl is optionally substituted with 1 to 4 wherein each $R^4$ is independently selected from the group consisting of lower alkyl, lower haloalkyl, —OH, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^{10}$, —$NR^{10}CO_2R^{10}$, —$SOR^7$, —$SO_2R^7$, $SO_2NR^{10}R^{10}$, phenyl (optionally substituted with lower alkyl, halo or lower haloalkyl, or —OH), and —$NR^{10}SO_2R^7$; each $R^3$ is independently selected from the group consisting of lower alkyl, lower haloalkyl, —OH, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^{10}$, —$NR^{10}CO_2R^{10}$, —$SOR^7$, —$SO_2R^7$, $SO_2NR^{10}R^{10}$, and —$NR^{10}SO_2R^7$; m is 0, 1, 2 or 3; $R^7$ is lower alkyl; and each $R^{10}$ is independently hydrogen or lower alkyl, or two $R^{10}$ together with the atom(s) attached thereto form a 4- to 6-membered ring; Y is selected from the group consisting of $CF_3$, Cl, F and Me, wherein the patient is undergoing or about to undergo chemotherapy or immunotherapy.

In some embodiments, the patient is undergoing or about to undergo immunotherapy. In some embodiments, the immunotherapy is selected from an immune checkpoint inhibitors such as anti-PD-1 antibody or anti-CTLA-4 antibody. In some embodiments, the patient is undergoing or about to undergo chemotherapy. In some embodiments, the chemotherapy is selected from paclitaxel, cyclophosphamide, or doxorubicin. In some embodiments, the compound represented by formula (I) and a chemotherapeutic agent or an immunotherapeutic agent are administered within one year of one another, or up to 18 months. In some embodiments, the compound represented by formula (I) and a chemotherapeutic agent or an immunotherapeutic agent are administered within one month of one another. In some embodiments, the compound represented by formula (I) and a chemotherapeutic agent or an immunotherapeutic agent are co-administered. In some embodiments, the patient suffers from cancer. In some embodiments, the cancer is selected from group consisting of a carcinoma, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer. In some embodiments, in the compound of Formula I, $R^2$ is 5- or 6-membered heteroaryl optionally substituted with 1 to 4 $R^4$. In some embodiments, in the compound of Formula I, $R^2$ is optionally substituted with 1 to 4 $R^4$, and $R^2$ is selected from the group consisting of furan, benzofuran, pyridine, pyridazine, pyrimidine, pyrazine, thiophene, thiazole, isothiazole, oxazole, isoxazole, oxadiazole, imidazole, pyrrole, and pyrazole. In some embodiments, in the compound of Formula I, $R^2$ is selected from the group consisting of

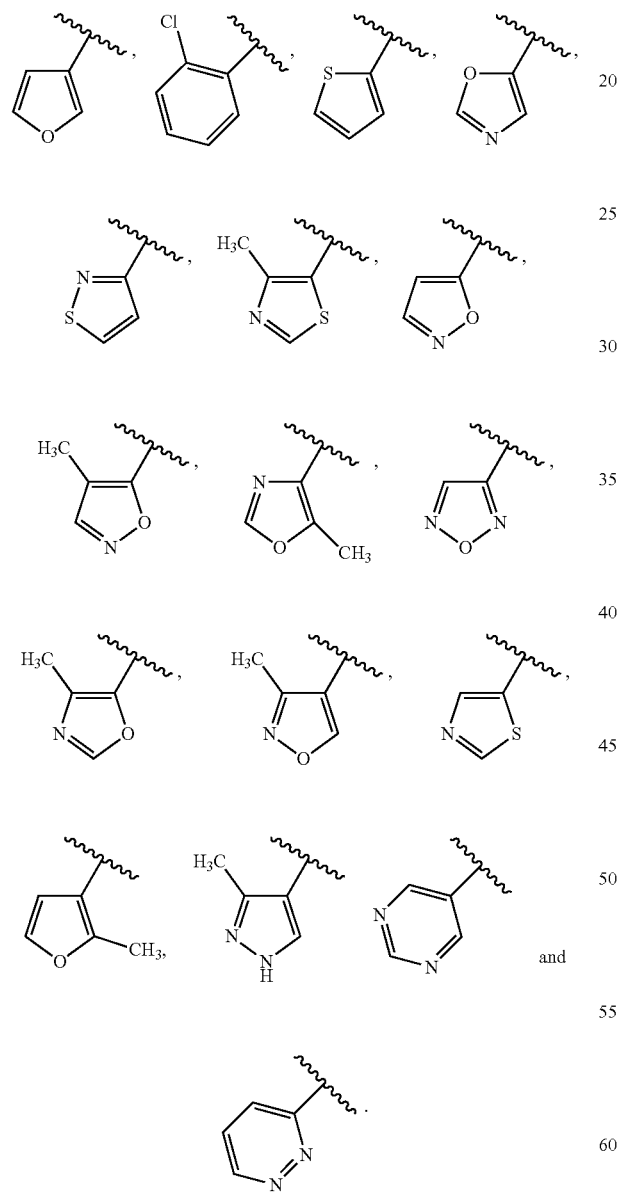

In some embodiments, in the compound of Formula I, $R^4$ is not optional and is selected from the group consisting of lower alkyl, halo, lower haloalkyl, —$OR^7$, cyano and phenyl optionally substituted methyl, and wherein $R^7$ is lower alkyl or lower haloalkyl. In some embodiments, in the compound of Formula I, m is 0. In some embodiments, the compound of Formula I is selected from:

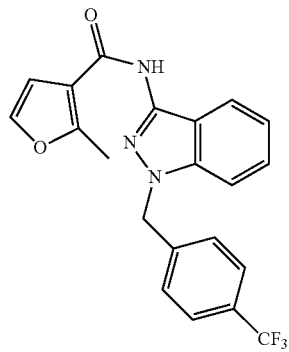 [SMILES: Cc1occc1C(=O)Nc1nn(Cc2ccc(C(F)(F)F)cc2)c2ccccc12]

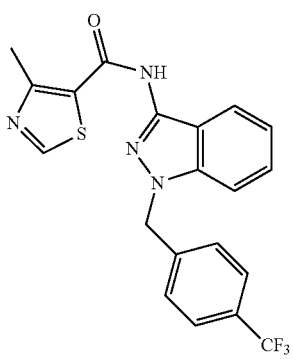

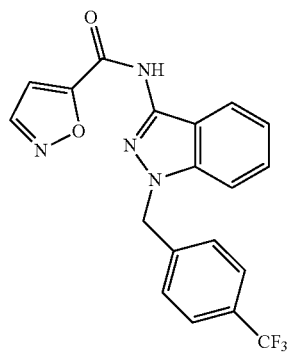

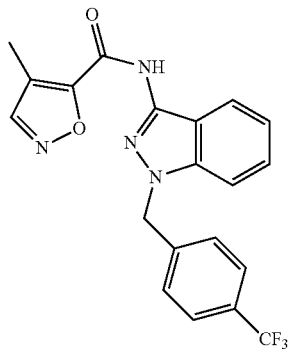

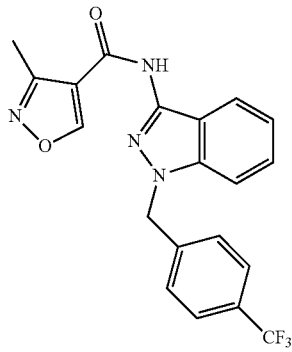

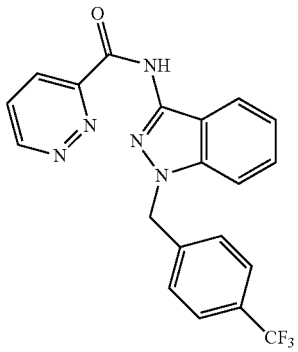

or tautomer thereof, and/or a pharmaceutically acceptable salt thereof. In some embodiments, the compound of formula I is

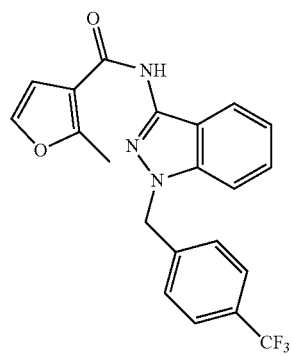 [SMILES: Cc1occc1C(=O)Nc1nn(Cc2ccc(C(F)(F)F)cc2)c2ccccc12]

or tautomer thereof, and/or a pharmaceutically acceptable salt thereof. In some embodiments, the method is a method of increasing a response to a chemotherapeutic agent. In some embodiments, the method is a method of increasing a response to an immunotherapeutic agent. In some embodiments, the patient is an adult human.

Other embodiments include a method of treating cancer in a patient in need thereof, comprising administering to the patient a chemotherapeutic agent or an immunotherapeutic agent and a compound represented by formula (I):

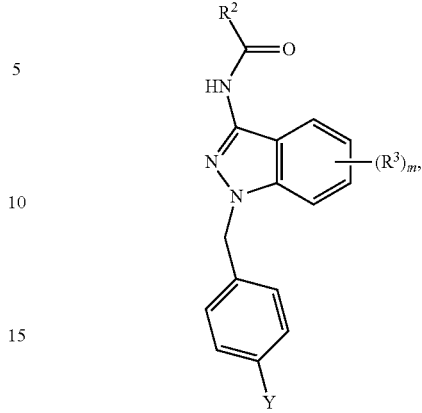

or tautomer thereof, and/or a pharmaceutically acceptable salt thereof; wherein $R^2$ is 6- to 10-membered aryl or 5- to 10-membered heteroaryl; wherein the 6- to 10-membered aryl or 5- to 10-membered heteroaryl is optionally substituted with 1 to 4 $R^4$, wherein each $R^4$ is independently selected from the group consisting of lower alkyl, lower haloalkyl, —OH, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, SO$_2$NR$^{10}$R$^{10}$, phenyl (optionally substituted with lower alkyl, halo or lower haloalkyl, or —OH), and —NR$^{10}$SO$_2$R$^7$; each $R^3$ is independently selected from the group consisting of lower alkyl, lower haloalkyl, —OH, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$, —SOR$^7$, —SO$_2$R$^7$, SO$_2$NR$^{10}$R$^{10}$, and —NR$^{10}$SO$_2$R$^7$; m is 0, 1, 2 or 3; $R^7$ is lower alkyl; and each $R^{10}$ is independently hydrogen or lower alkyl, or two $R^{10}$ together with the atom(s) attached thereto form a 4- to 6-membered ring; Y is selected from the group consisting of CF$_3$, Cl, F and Me.

In some embodiments, the patient is undergoing or about to undergo immunotherapy. In some embodiments, the immunotherapy is selected from an immune checkpoint inhibitors such as anti-PD-1 antibody or anti-CTLA-4 antibody. In some embodiments, the patient is undergoing or about to undergo chemotherapy. In some embodiments, the chemotherapy is selected from paclitaxel, cyclophosphamide, or doxorubicin. In some embodiments, the compound represented by formula (I) and a chemotherapeutic agent or an immunotherapeutic agent are administered within one year, or up to 18 months, of one another. In some embodiments, the compound represented by formula (I) and a chemotherapeutic agent or an immunotherapeutic agent are administered within one month of one another. In some embodiments, the compound represented by formula (I) and a chemotherapeutic agent or an immunotherapeutic agent are co-administered. In some embodiments, the cancer is selected from group consisting of a carcinoma, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer. In some embodiments, the cancer is selected from group consisting of neuroendocrine prostate cancer, activated B-cell subtype of diffuse large B-cell lymphoma, and triple-negative breast cancer. In some embodiments, in the compound of Formula I, $R^2$ is 5- or 6-membered heteroaryl optionally substituted with 1 to 4 $R^4$. In some embodiments, in the compound of Formula I, $R^2$ is optionally substituted with 1 to 4 $R^4$, and $R^2$ is selected from the group consisting of furan, benzofuran, pyridine, pyridazine, pyrimidine, pyrazine, thiophene, thiazole, isothiazole, oxazole, isoxazole, oxadiazole, imidazole, pyrrole, and pyrazole. In some embodiments, in the compound of Formula I, $R^2$ is selected from the group consisting of

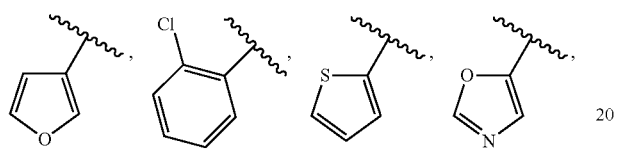

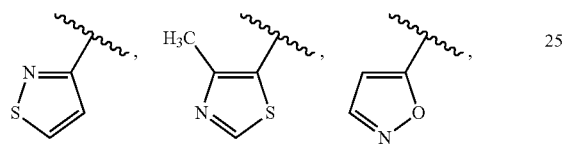

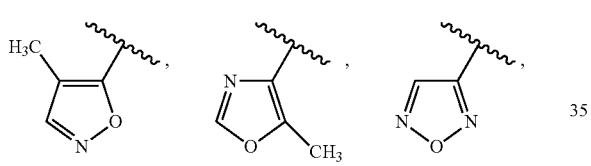

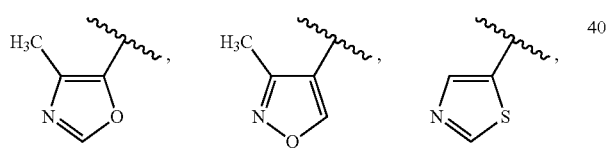

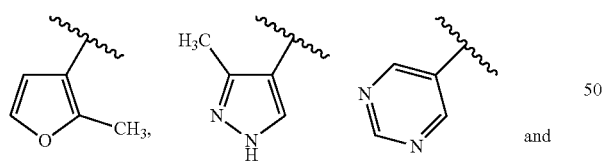

In some embodiments, in the compound of Formula I, $R^4$ is not optional and is selected from the group consisting of lower alkyl, halo, lower haloalkyl, —OH, —$OR^7$, cyano and phenyl optionally substituted methyl, and wherein $R^7$ is lower alkyl or lower haloalkyl. In some embodiments, in the compound of Formula I, m is 0. In some embodiments, the compound of Formula I is selected from:

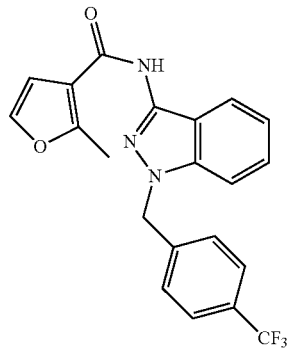

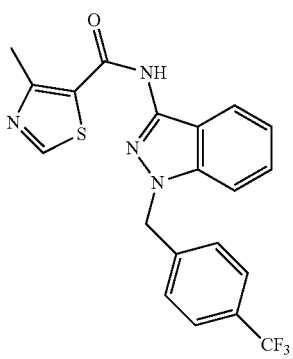

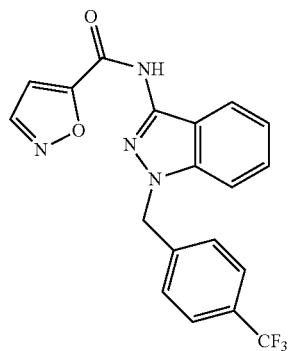

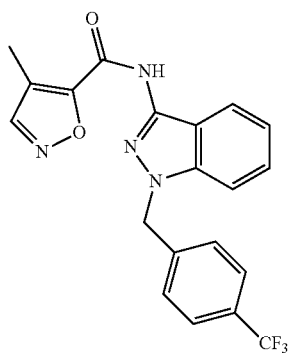

-continued

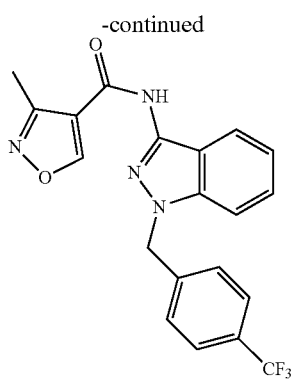

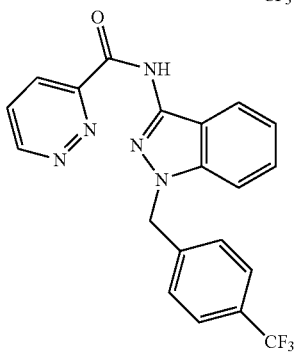

or tautomer thereof, and/or a pharmaceutically acceptable salt thereof. In some embodiments, the compound of formula I is

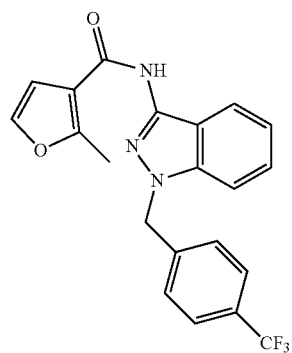

or tautomer thereof, and/or a pharmaceutically acceptable salt thereof. In some embodiments, the method comprises administering to the patient a chemotherapeutic agent. In some embodiments, the method comprises administering to the patient an immunotherapeutic agent. In some embodiments, the patient is an adult human.

DETAILED DESCRIPTION

Figure 1:
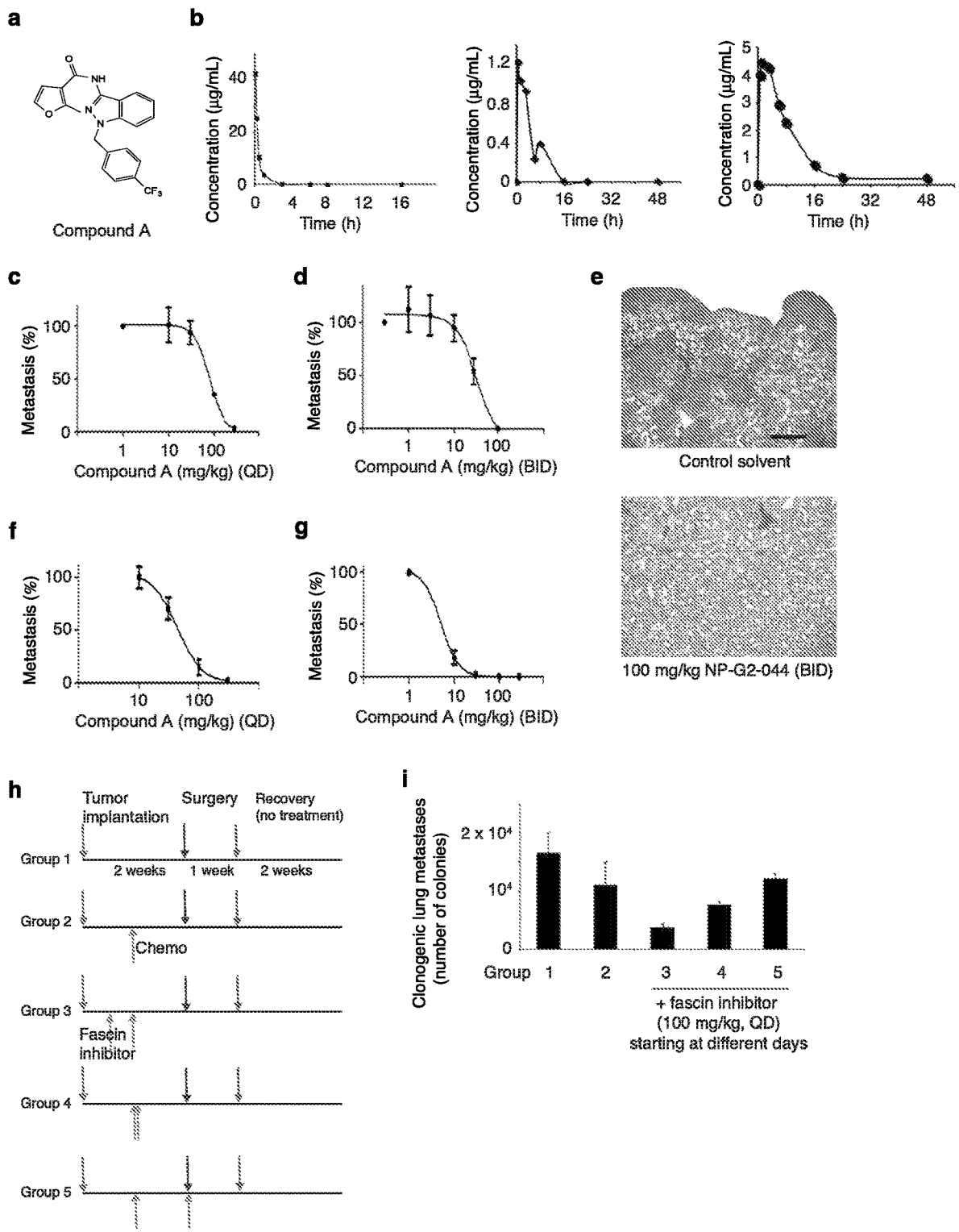
FIG. 1. Pharmacokinetic (PK) and pharmacodynamic (PD) studies of the fascin inhibitor NP-G2-044 in mice. (a) The chemical structure of NP-G2-044. (b) PK profiles of NP-G2-044 in mice. NP-G2-044 was intravenously (at 20 mg/kg, left panel) or orally (at 20 mg/kg, middle panel; at 50 mg/kg, right panel) administered into mice. Blood samples were collected at different time points. The plasma samples were then extracted and the concentrations of NP-G2-044 were determined by LC-MS/MS. The concentration-time curves are shown. (c-f) NP-G2-044 blocks tumor metastasis as a single agent. (c and d) MDA-MB-231 human breast tumor cells were implanted into the mammary fat pad and the metastasis to the lung was quantified. QD: once a day. BID: twice a day treatment with different concentrations of NP-G2-044. Each group had 3 to 4 mice. Data are shown as mean±SEM. (e) Representative images of hematoxylin & eosin staining show lung tissue sections from mice injected with MDA-MB-231 cells treated with control solvent or treated with 100 mg/kg NP-G2-044 after the mice were sacrificed. (f and g) 4T1 mouse breast tumor cells were implanted into the mammary fat pad and the metastasis to the lung was quantified. Each group had 3 to 4 mice. Data are shown as mean±SEM. (h and i) Effect of NP-G2-044 on tumor metastasis when administered at different time points. 4T1 breast tumor cells were implanted into the fat pad. Chemotherapy with Paclitaxel (20 mg/kg, twice weekly) was given on Day 8. Primary tumors were surgically removed on Day 15. Metastatic tumors in the lung were quantified on Day 32. 100 mg/kg of NP-G2-044 was given once daily to mice starting on Day 4, 8 or 15. Each group had 2 to 4 mice. Data are shown as mean±SEM.
Figure 2:
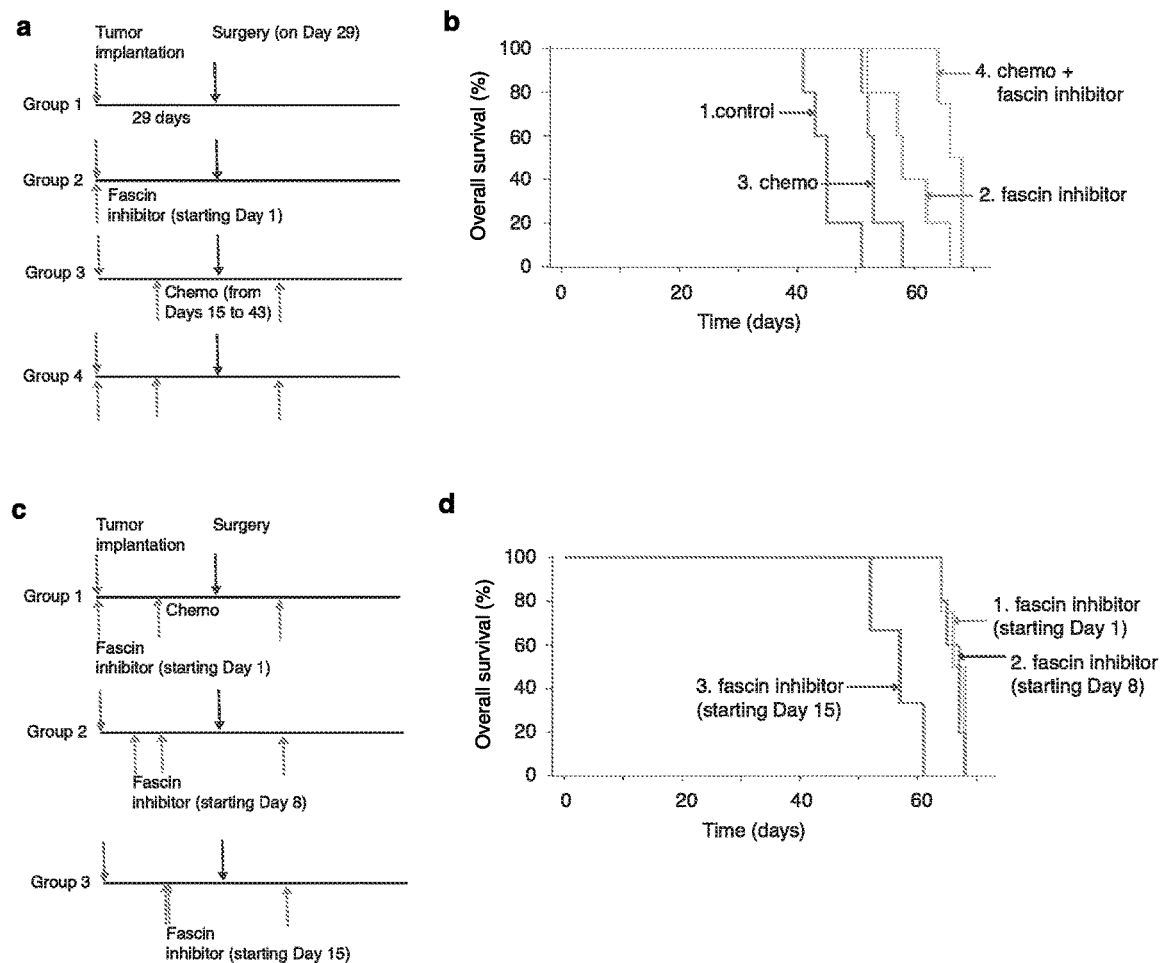
FIG. 2. Fascin inhibitor NP-G2-044 increases overall survival of tumor-bearing mice. NSG mice implanted with MDA-MB-231 tumor cells were treated with fascin inhibitor, chemotherapy, or a combination of fascin inhibitor+chemotherapy. Primary tumors were surgically removed on Day 29. Chemotherapy treatment was for 4 weeks (as marked). NP-G2-044 started on Day 1. (a and b) Fascin inhibitor, chemotherapy and the combination all increased the overall survival of tumor-bearing mice. (a) Experimental schemes for the data shown in (b). (b) The overall survival curves of mice from the four groups of mice. (c and d) In the combination therapies, earlier treatments with NP-G2-044 (starting on day 1 or 8) had better effect than late treatment starting on day 15). (c) Experimental schemes for the data shown in (d). (d) The overall survival curves of mice from the three different groups. The group with starting day 1 was the same one as the fourth group in (b). Death was used as the endpoint. Each group had 3 to 5 mice.
Figure 3:
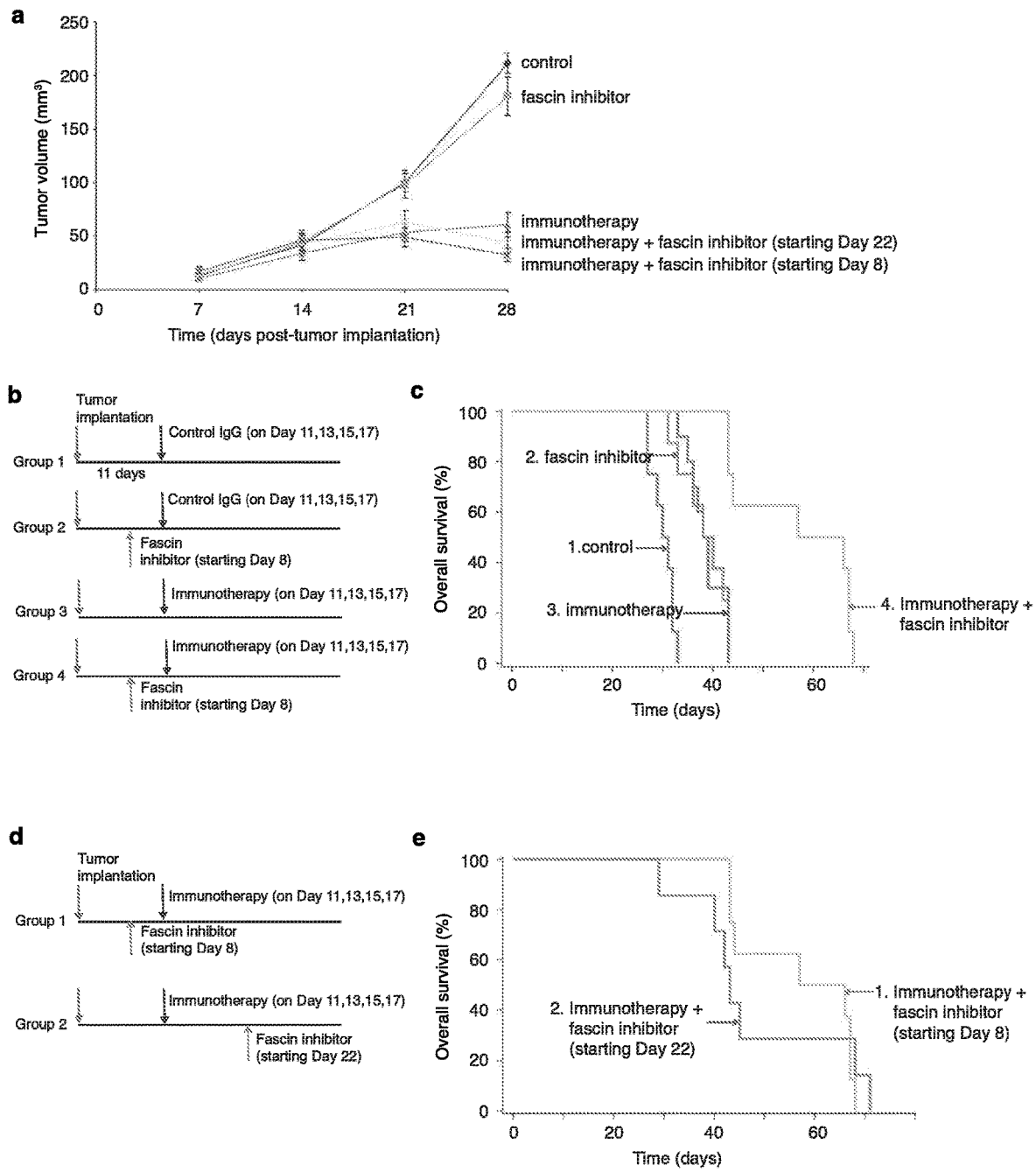
FIG. 3. Fascin inhibitor boosts the immunotherapy response. (a) Effect on the primary tumor growth. The primary tumor volumes were measured weekly until all the mice in the control group died. Data are shown as mean±SEM. (b and c) Fascin inhibitor, immunotherapy (anti-PD-1 and anti-CTLA-4 antibodies), and the combination all increased the overall survival of tumor-bearing mice. (b) Experimental schemes for the data shown in (c). (c) The overall survival curves of mice from the four groups of mice. (d and e) In the combination therapies, both early treatment with NP-G2-044 (starting on day 8) and late treatment (starting on day 22) boosted the immunotherapy response. (d) Experimental schemes for the data shown in (e). (e) The overall survival curves of mice from the two different groups. The group with starting day 8 was the same one as the fourth group in (c). Death was used as the endpoint. Each group had 7 to 10 mice.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Definitions

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, C$_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to an alkyl group having 1 to 4 carbons.

"Alkenyl" refers to straight or branched hydrocarbyl groups having the indicated number of carbon atoms, usually from 1 to 8 carbon atoms, for example 2 to 4 carbon atoms, and at least 1 and preferably from 1 to 2 sites of vinyl (>C═C<) unsaturation. Such groups are exemplified, for example, by vinyl, allyl, and but-3-en-1-yl. Included within this term are the cis and trans isomers or mixtures of these isomers. "Lower alkenyl" refers to an alkenyl group having 1 to 4 carbons, which can be indicated by $C_2$-$C_4$ alkenyl.

"Cycloalkyl" indicates a non-aromatic partially saturated, or fully saturated carbocyclic ring having the indicated number of carbon ring atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Aryl" indicates an aromatic carbon ring having the indicated number of carbon atoms, for example, 6 to 12 or 6 to 10 carbon atoms, in the ring. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Carboxy" or "carboxyl" refers to —COOH or a salt thereof.

"Heteroaryl" indicates an aromatic ring containing the indicated number of ring atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. 5-Membered heteroaryl is a heteroaryl having 5 ring atoms. 6-Membered heteroaryl is a heteroaryl having 6 ring atoms. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., S$^+$—O$^-$ or SO$_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic partially saturated, or fully saturated ring having the indicated number of ring atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. 5-Membered heterocycloalkyl is a heterocycloalkyl having 5 ring atoms. 6-Membered heterocycloalkyl is a heterocycloalkyl having 6 ring atoms. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. When nitrogen is present in a heterocycloalkyl ring, it may, where the nature of the adjacent atoms and groups permits, exist in an oxidized state (i.e., N$^+$—O$^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., S$^+$—O$^-$ or —SO$_2$—). Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. An alkoxy group is further meant to encompass a cycloalkyl group, as defined above, that is likewise attached through an oxygen bridge. Alkoxy groups will usually have from 1 to 6 carbon atoms attached through the oxygen bridge. "Lower alkoxy" refers to an alkoxy group having 1 to 4 carbons.

The term "halo" includes fluoro, chloro, bromo, and iodo, and the term "halogen" includes fluorine, chlorine, bromine, and iodine.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

"Haloalkyl" refers to alkyl groups substituted with 1 to 5, 1 to 3, or 1 to 2 halo groups, wherein alkyl and halo are as defined herein. Lower haloalkyl refers to a C$_1$-C$_4$ alkyl substituted with 1 to 5, 1 to 3, or 1 to 2 halo groups.

"Lower alkylphenyl" refers to C$_1$-C$_4$ alkyl-phenyl.

"Isomers" are different compounds that have the same molecular formula. "Stereoisomers" are isomers that differ only in the way the atoms are arranged in space. "Enantiomers" are stereoisomers that are non-superimposable mirror images of each other. A 1:1 mixture of a pair of enantiomers is a "racemic" mixture. The symbol "(±)" may be used to designate a racemic mixture where appropriate.

"Diasteroisomers" are stereoisomers that have at least two asymmetric atoms, but which are not mirror-images of each other. A "meso compound" or "meso isomer" is a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds disclosed and/or described herein contain one or more asymmetric centers and can thus give rise to enantiomers, diastereomers, meso isomers and other stereoisomeric forms. Unless otherwise indicated, compounds disclosed and/or described herein include all such possible enantiomers, diastereomers, meso isomers and other stereoisomeric forms, including racemic mixtures, optically pure forms and intermediate mixtures. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers.

"Tautomers" are structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. When the compounds described herein contain moieties capable of tautomerization, and unless specified otherwise, it is intended that the compounds include all possible tautomers.

Pharmaceutically acceptable forms of the compounds recited herein include pharmaceutically acceptable salts, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The compounds disclosed and/or described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

As used herein the terms "group", "radical" or "fragment" are synonymous and are intended to indicate functional groups or fragments of molecules attachable to a bond or other fragments of molecules.

The term "active agent" is used to indicate a substance which has biological activity. In some embodiments, an "active agent" is a substance having pharmaceutical utility. For example an active agent may be an anti-metastasis therapeutic.

The term "therapeutically effective amount" or "effective amount" means an amount effective, when administered to a human or non-human subject, to provide a therapeutic benefit such as amelioration of symptoms, slowing of disease progression, or prevention of disease, or to inhibit fascin activity in vitro or in vivo, e.g., a therapeutically effective amount may be an amount sufficient to decrease the symptoms of a disease responsive to inhibition of fascin activity.

"Inhibition of fascin activity" refers to a decrease in fascin activity as a direct or indirect response to the presence of at least one compound, or pharmaceutically acceptable salt thereof, described herein, relative to the activity of fascin in the absence of the at least one compound, or pharmaceutically acceptable salt thereof, described herein. The decrease in activity may be due to the direct interaction of the at least one compound, or pharmaceutically acceptable salt thereof, described herein with fascin or with one or more other factors that in turn affect fascin activity.

In some embodiments, the compound, or pharmaceutically acceptable salt thereof, described herein has an $IC_{50}$ (the concentration that inhibits 50% of fascin activity) value of about 500 micromolar, about 100 micromolar, about 10 micromolar, about 1 micromolar, about 500 nanomolar, about 400 nanomolar, about 300 nanomolar, about 200 nanomolar, about 100 nanomolar, about 50 nanomolar, about 10 nanomolar, of less than about 10 nanomolar, or a range between and including any two of these values.

A "disease responsive to inhibition of fascin activity" is a disease in which inhibiting fascin provides a therapeutic benefit such as an amelioration of symptoms, decrease in disease progression, prevention or delay of disease onset, prevention or amelioration of an inflammatory response, or inhibition of aberrant activity and/or death of certain cell-types (such as cancer cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

As used herein, the term "cancer" includes solid mammalian tumors as well as hematological malignancies. The terms "tumor cell(s)" and "cancer cell(s)" are used interchangeably herein.

"Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system; sarcomas of the soft tissue and bone; and melanoma of cutaneous and intraocular origin.

The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS.

Also, in these examples and elsewhere, abbreviations have the following meanings:
° C.=degree Celsius
μL=microliter
μM=micromolar
DDT=dithiothreitol
DMSO=dimethyl sulfoxide
g=gram
kg=kilogram
hr or h=hour
L=liter
M=molar
nM=nanomolar
mg=milligram
MHz=mega Hertz
min=minute
mL=milliliter
mm=millimeter
mM=millimolar
mmol=millimole
mol=mole
PMSF=phenylmethylsulfonyl fluoride
N=normal
EDTA=ethylenediaminetetraacetic acid
μm=micrometer
r.p.m=round per minute
S.D.=standard deviation
v/v=volume/volume
wt=weight Metastasis Inhibitor Compounds The present technology provides compounds for use in co-therapies that include metastasis inhibitors such as the fascin inhibitors described in U.S. patent application Ser. Nos. 13/972,649 and 14/626,791 along with U.S. Pat. No. 9,573,946, each of which is incorporated by reference in its entirety.

In some embodiments, the metastasis inhibitor is a compound selected from Formula I, Ia or Ib:

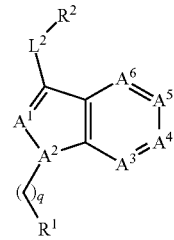

Formula I

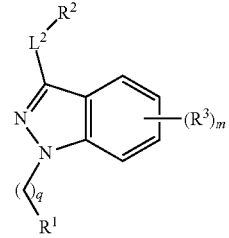

Formula Ia

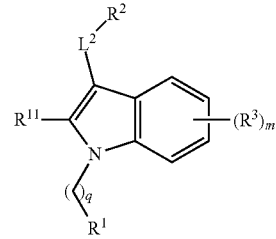

Formula Ib or tautomer thereof, and/or a pharmaceutically acceptable salt thereof;
wherein
$A^1$, $A^2$, $A^3$, $A^4$, $A^5$ and $A^6$ are independently CH, $CR^3$ or N, provided that no more than four of $A^1$, $A^2$, $A^3$, $A^4$, $A^5$ and $A^6$ are N;
$R^1$ is phenyl, 5-membered heteroaryl or 6-membered heteroaryl, wherein the phenyl, 5-membered heteroaryl or 6-membered heteroaryl is optionally substituted with 1 to 3 $R^6$;
$L^2$ is selected from the group consisting of $-NR^8-$, $-C(O)NR^8-$, $-NR^8C(O)-$, $-C(O)CR^8_2-$, $-CR^8_2C(O)-$, $-NR^8CR^8_2-$, and $-CR^8_2NR^8-$;
$R^2$ is hydrogen, lower alkyl, 6- to 10-membered aryl or 5- to 10-membered heteroaryl; wherein the 6- to 10-membered aryl or 5- to 10-membered heteroaryl is optionally substituted with 1 to 4 $R^4$, wherein each $R^4$ is independently selected from the group consisting of lower alkyl, lower haloalkyl, phenyl (optionally substituted with lower alkyl, halo, lower haloalkyl, or $-OH$), $-OH$, $-SH$, $-NR^{10}R^{10}$, halo, cyano, nitro, $-COH$, $-COR^7$, $-CO_2H$, $-CO_2R^7$, $-CONR^{10}R^{10}$, $-OCOR^7$, $-OCO_2R^7$, $-OCONR^{10}R^{10}$, $-NR^{10}CO_2R^7$, $-NR^{10}CO_2R^7$, $-SOR^7$, $-SO_2R^7$, $-SO_2NR^{10}R^{10}$, and $-NR^{10}SO_2R^7$;
each $R^3$ is independently selected from the group consisting of lower alkyl, lower haloalkyl, $-OH$, $-SH$, $-NR^{10}R^{10}$, halo, cyano, nitro, $-COH$, $-COR^7$, $-CO_2H$, $-CO_2R^7$, $-CONR^{10}R^{10}$, $-OCOR^7$, $-OCO_2R^7$, $-OCONR^{10}R^{10}$, —NR¹⁰CO₂R⁷, —NR¹⁰CO₂R⁷, —SOR⁷, —SO₂R⁷, —SO₂NR¹⁰R¹⁰, and —NR¹⁰SO₂R⁷;

m is 0, 1, 2 or 3;

q is 1, 2 or 3;

each $R^6$ is independently selected from the group consisting of cyano, halo, lower alkyl (such as methyl or ethyl), lower haloalkyl, and —CH₂OH;

$R^7$ is lower alkyl (such as methyl or ethyl) or lower haloalkyl;

$R^8$ is hydrogen or lower alkyl (such as methyl or ethyl);

each $R^{10}$ is independently hydrogen or lower alkyl (such as methyl or ethyl), or two $R^{10}$ together with the atom(s) attached thereto form a 4- to 6-membered ring; and $R^{11}$ is hydrogen or $R^3$;

provided that the compound is not N-(1-(4-(trifluoromethyl)benzyl)-1H-indazol-3-yl)furan-2-carboxamide.

In some embodiments, the metastasis inhibitor is a compound selected from a compound of Formula II

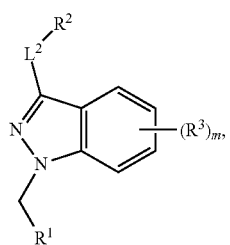

Formula II or tautomer thereof, and/or a pharmaceutically acceptable salt thereof;

wherein $R^1$ is phenyl, 5-membered heteroaryl or 6-membered heteroaryl, wherein the phenyl, 5-membered heteroaryl or 6-membered heteroaryl is optionally substituted with 1 to 3 $R^6$; $L^2$ is selected from the group consisting of —C(O)NH—, —NHC(O)—, —C(O)CH₂—, —CH₂C(O)—, —NHCH₂—, and —CH₂NH—;

$R^2$ is 6- to 10-membered aryl or 5- to 10-membered heteroaryl; wherein the 6- to 10-membered aryl or 5- to 10-membered heteroaryl is optionally substituted with 1 to 4 wherein each $R^4$ is independently selected from the group consisting of lower alkyl, lower haloalkyl, phenyl (optionally substituted with lower alkyl, halo or lower haloalkyl, or —OH), —OH, —SH, —SR⁷, —NR¹⁰R¹⁰, halo, cyano, nitro, —COH, —COR⁷, —CO₂H, —CO₂R⁷, —CONR¹⁰R¹⁰, —OCOR⁷, —OCO₂R⁷, —OCONR¹⁰R¹⁰, —NR¹⁰CO₂R⁷, —NR¹⁰CO₂R⁷, —SOR⁷, —SO₂R⁷, —SO₂NR¹⁰R¹⁰, and —NR¹⁰SO₂R⁷;

each $R^3$ is independently selected from the group consisting of lower alkyl, lower haloalkyl, —OH, —SH, —SR⁷, —NR¹⁰R¹⁰, halo, cyano, nitro, —COH, —COR⁷, —CO₂H, —CO₂R⁷, —CONR¹⁰R¹⁰, —OCOR⁷, —OCO₂R⁷, —OCONR¹⁰R¹⁰, —NR¹⁰COR¹⁰, —NR¹⁰CO₂R¹⁰, —SOR⁷, —SO₂R⁷, —SO₂NR¹⁰R¹⁰, and —NR¹⁰SO₂R⁷;

m is 0, 1, 2 or 3;

n is 0, 1, 2 or 3;

q is 1, 2 or 3;

each $R^6$ is independently selected from the group consisting of halo, cyano, lower alkyl (preferably methyl or ethyl) and lower haloalkyl;

$R^7$ is lower alkyl (preferably methyl or ethyl) or lower haloalkyl; and each $R^{10}$ is independently hydrogen or lower alkyl (preferably methyl or ethyl), or two $R^{10}$ together with the atom(s) attached thereto form a 4- to 6-membered ring;

provided that the compound is not N-(1-(4-(trifluoromethyl)benzyl)-1H-indazol-3-yl)furan-2-carboxamide.

In some embodiments, the metastasis inhibitor is a compound selected from a compound of Formula IIIa, IIIb, IIIc or IIId

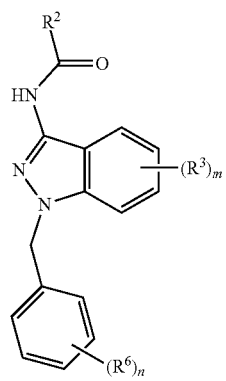

Formula IIIa

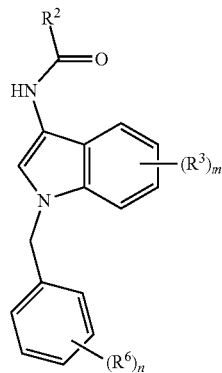

Formula IIIb

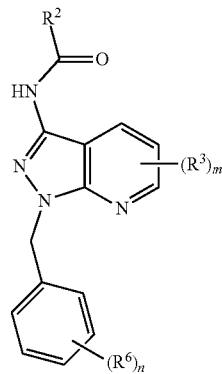

Formula IIIc

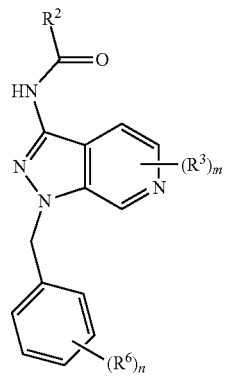

Formula IIId or tautomer thereof, and/or a pharmaceutically acceptable salt thereof;

wherein $R^2$ is 6- to 10-membered aryl or 5- to 10-membered heteroaryl; wherein the 6- to 10-membered aryl or 5- to 10-membered heteroaryl is optionally substituted with 1 to 4 $R^4$, wherein each $R^4$ is independently selected from the group consisting of lower alkyl, lower haloalkyl, phenyl (optionally substituted with lower alkyl, halo or lower haloalkyl, or —OH), —OH, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^7$, —NR$^{10}$CO$_2$R$^7$, —SOR$^7$, —SO$_2$R$^7$, —SO$_2$NR$^{10}$R$^{10}$, and —NR$^{10}$SO$_2$R$^7$;

each $R^3$ is independently selected from the group consisting of lower alkyl, lower haloalkyl, —OH, —OR$^{10}$, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^7$, —NR$^{10}$CO$_2$R$^7$, —SOR$^7$, —SO$_2$R$^7$, —SO$_2$NR$^{10}$R$^{10}$, and —NR$^{10}$SO$_2$R$^7$;

m is 0, 1, 2 or 3;

n is 0, 1, 2 or 3;

each $R^6$ is independently selected from the group consisting of halo, cyano, lower alkyl (preferably methyl or ethyl) and lower haloalkyl;

$R^7$ is lower alkyl (preferably methyl or ethyl); and each $R^{10}$ is independently hydrogen or lower alkyl (preferably methyl or ethyl), or two $R^{10}$ together with the atom(s) attached thereto form a 4- to 6-membered ring;

provided that the compound is not N-(1-(4-(trifluoromethyl) benzyl)-1H-indazol-3-yl)furan-2-carboxamide.

In some embodiments, the metastasis inhibitor is a compound selected from a compound of Formula IVa, IVb, IVc, IVd, IVe, IVf, IVg, IVh:

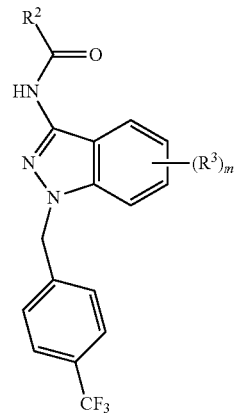

Formula IVa

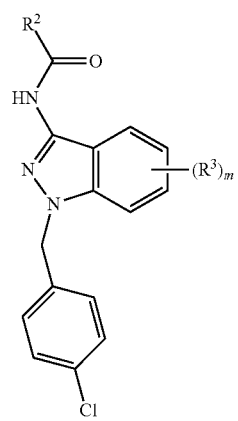

Formula IVb

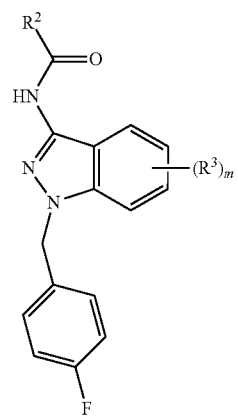

Formula IVc

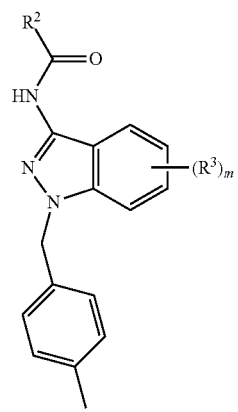

Formula IVd

-continued

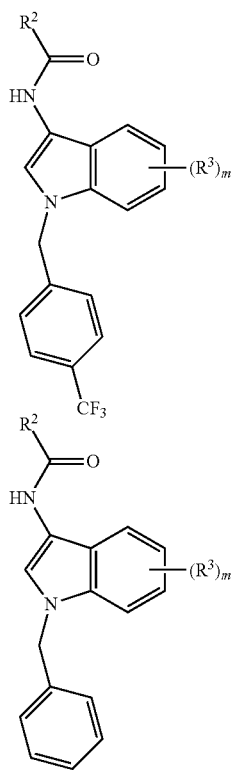

Formula IVe

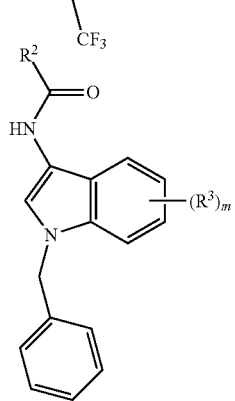

Formula IVf

Formula IVg

Formula IVh or tautomer thereof, and/or a pharmaceutically acceptable salt thereof;

wherein

R² is 6- to 10-membered aryl or 5- to 10-membered heteroaryl; wherein the 6- to 10-membered aryl or 5- to 10-membered heteroaryl is optionally substituted with 1 to 4 wherein each R⁴ is independently selected from the group consisting of lower alkyl, lower haloalkyl, —OH, —SH, —SR⁷, —NR¹⁰R¹⁰, halo, cyano, nitro, —COH, —COR⁷, —CO₂H, —CO₂R⁷, —CONR¹⁰R¹⁰, —OCOR⁷, —OCO₂R⁷, —OCONR¹⁰R¹⁰, —NR¹⁰CO₂R¹⁰, —NR¹⁰CO₂R¹⁰, —SOR⁷, —SO₂R⁷, —SO₂NR¹⁰R¹⁰, phenyl (optionally substituted with lower alkyl, halo or lower haloalkyl, or —OH), and —NR¹⁰SO₂R⁷;

each R³ is independently selected from the group consisting of lower alkyl, lower haloalkyl, —OH, —OR¹⁰, —SH, —SR⁷, —NR¹⁰R¹⁰, halo, cyano, nitro, —COH, —COR⁷, —CO₂H, —CO₂R⁷, —CONR¹⁰R¹⁰, —OCOR⁷, —OCO₂R⁷, —OCONR¹⁰R¹⁰, —NR¹⁰COR¹⁰, —NR¹⁰CO₂R¹⁰, —SOR⁷, —SO₂R⁷, —SO₂NR¹⁰R¹⁰, and —NR¹⁰SO₂R⁷;

m is 0, 1, 2 or 3;

R⁷ is lower alkyl (preferably methyl or ethyl); and each R¹⁰ is independently hydrogen or lower alkyl (preferably methyl or ethyl), or two R¹⁰ together with the atom(s) attached thereto form a 4- to 6-membered ring;

provided that the compound is not N-(1-(4-(trifluoromethyl)benzyl)-1H-indazol-3-yl)furan-2-carboxamide.

In some embodiments, the metastasis inhibitor is a compound of Formula VIII, VIIIa or VIIIb:

Formula VIIIa

Formula VIIIb

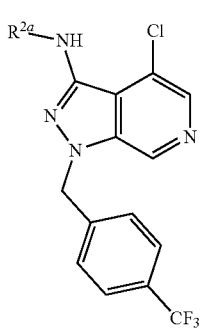

Formula VIIIc or tautomer thereof, and/or a pharmaceutically acceptable salt thereof;
wherein
$L^2$ is selected from the group consisting of —$NR^8$—, —$C(O)NR^8$—, —$NR^8C(O)$—, —$C(O)CR^8{}_2$—, —$CR^8{}_2C(O)$—, —$NR^8CR^8{}_2$—, and —$CR^8{}_2NR^8$—;
$R^{2a}$ is hydrogen, or —$NHC(O)R^2$, wherein $R^2$ is lower alkyl, 6-membered aryl or 5- to 10-membered heteroaryl; wherein the 6- to 10-membered aryl or 5- to 10-membered heteroaryl is optionally substituted with 1 to 4 $R^4$, wherein each $R^4$ is independently selected from the group consisting of lower alkyl, lower haloalkyl, phenyl (optionally substituted with lower alkyl, halo, lower haloalkyl, or —OH), —OH, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^7$, —$NR^{10}CO_2R^7$, —$SOR^7$, —$SO_2R^7$, —$SO_2NR^{10}R^{10}$, and —$NR^{10}SO_2R^7$; and each $R^3$ is independently selected from the group consisting of lower alkyl, lower haloalkyl, —OH, —SH, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^7$, —$NR^{10}CO_2R^7$, —$SOR^7$, —$SO_2R^7$, —$SO_2NR^{10}R^{10}$, and —$NR^{10}SO_2R^7$.

In some embodiments, $L^2$ is —$C(O)NH$—, —$C(O)CH_2$—, or —$CH_2NH$—.

In some embodiments, $A^1$ is N and $A^2$, $A^3$, $A^4$, $A^5$ and $A^6$ are independently CH or $CR^3$. In some embodiments, $A^2$ is N and $A^1$, $A^3$, $A^4$, $A^5$ and $A^6$ are independently CH or $CR^3$. In some embodiments, $A^3$ is N and $A^1$, $A^2$, $A^4$, $A^5$ and $A^6$ are independently CH or $CR^3$. In some embodiments, $A^4$ is N and $A^1$, $A^2$, $A^3$, $A^5$ and $A^6$ are independently CH or $CR^3$. In some embodiments, $A^5$ is N and $A^1$, $A^2$, $A^3$, $A^4$, and $A^6$ are independently CH or $CR^3$. In some embodiments, $A^6$ is N and $A^1$, $A^2$, $A^3$, $A^4$, and $A^5$ are independently CH or $CR^3$.

In some embodiments, $A^1$ and $A^2$ are N. In some embodiments, $A^3$, $A^4$, $A^5$ and $A^6$ are independently CH or $CR^3$. In some embodiments, $A^3$ is N, and $A^4$, $A^5$ and $A^6$ are independently CH or $CR^3$. In some embodiments, $A^4$ is N and $A^3$, $A^5$ and $A^6$ are independently CH or $CR^3$. In some embodiments, $A^5$ is N, and $A^3$, $A^4$ and $A^6$ are independently CH or $CR^3$. In some embodiments, $A^6$ is N, and $A^3$, $A^4$, and $A^5$ are independently CH or $CR^3$. In some embodiments, $A^3$ and $A^4$ are N, and $A^5$ and $A^6$ are independently CH or $CR^3$. In some embodiments, $A^3$ and $A^5$ are N, and $A^4$ and $A^6$ are independently CH or $CR^3$. In some embodiments, $A^3$ and $A^6$ are N, and $A^4$ and $A^5$ are independently CH or $CR^3$. In some embodiments, $A^4$ and $A^5$ are N, and $A^3$ and $A^6$ are independently CH or $CR^3$. In some embodiments, $A^4$ and $A^6$ are N, and $A^3$ and $A^5$ are independently CH or $CR^3$. In some embodiments, $A^5$ and $A^6$ are N, and $A^3$ and $A^4$ are independently CH or $CR^3$.

In some embodiments, $A^1$ and $A^3$ are N. In some embodiments, $A^2$, $A^4$, $A^5$ and $A^6$ are independently CH or $CR^3$. In some embodiments, $A^4$ is N, and $A^2$, $A^5$ and $A^6$ are independently CH or $CR^3$. In some embodiments, $A^5$ is N and $A^2$, $A^4$ and $A^6$ are independently CH or $CR^3$. In some embodiments, $A^6$ is N, and $A^2$, $A^4$ and $A^5$ are independently CH or $CR^3$. In some embodiments, $A^2$ and $A^4$ are N, and $A^5$ and $A^6$ are independently CH or $CR^3$. In some embodiments, $A^2$ and $A^5$ are N, and $A^4$ and $A^6$ are independently CH or $CR^3$. In some embodiments, $A^2$ and $A^6$ are N, and $A^4$ and $A^5$ are independently CH or $CR^3$. In some embodiments, $A^4$ and $A^5$ are N, and $A^2$ and $A^6$ are independently CH or $CR^3$. In some embodiments, $A^4$ and $A^6$ are N, and $A^2$ and $A^5$ are independently CH or $CR^3$. In some embodiments, $A^5$ and $A^6$ are N, and $A^2$ and $A^4$ are independently CH or $CR^3$.

In some embodiments, $A^1$ and $A^4$ are N. In some embodiments, $A^2$, $A^3$, $A^5$ and $A^6$ are independently CH or $CR^3$. In some embodiments, $A^3$ is N, and $A^2$, $A^5$ and $A^6$ are independently CH or $CR^3$. In some embodiments, $A^5$ is N and $A^2$, $A^3$ and $A^6$ are independently CH or $CR^3$. In some embodiments, $A^6$ is N, and $A^2$, $A^3$ and $A^5$ are independently CH or $CR^3$. In some embodiments, $A^2$ and $A^3$ are N, and $A^5$ and $A^6$ are independently CH or $CR^3$. In some embodiments, $A^2$ and $A^5$ are N, and $A^3$ and $A^6$ are independently CH or $CR^3$. In some embodiments, $A^2$ and $A^6$ are N, and $A^3$ and $A^5$ are independently CH or $CR^3$. In some embodiments, $A^3$ and $A^5$ are N, and $A^2$ and $A^6$ are independently CH or $CR^3$. In some embodiments, $A^3$ and $A^6$ are N, and $A^2$ and $A^5$ are independently CH or $CR^3$. In some embodiments, $A^5$ and $A^6$ are N, and $A^2$ and $A^3$ are independently CH or $CR^3$.

In some embodiments, $A^1$ and $A^5$ are N. In some embodiments, $A^2$, $A^4$, $A^3$ and $A^6$ are independently CH or $CR^3$. In some embodiments, $A^4$ is N, and $A^2$, $A^3$ and $A^6$ are independently CH or $CR^3$. In some embodiments, $A^3$ is N and $A^2$, $A^4$ and $A^6$ are independently CH or $CR^3$. In some embodiments, $A^6$ is N, and $A^2$, $A^4$ and $A^3$ are independently CH or $CR^3$. In some embodiments, $A^2$ and $A^4$ are N, and $A^3$ and $A^6$ are independently CH or $CR^3$. In some embodiments, $A^2$ and $A^3$ are N, and $A^4$ and $A^6$ are independently CH or $CR^3$. In some embodiments, $A^2$ and $A^6$ are N, and $A^4$ and $A^3$ are independently CH or $CR^3$. In some embodiments, $A^4$ and $A^3$ are N, and $A^2$ and $A^6$ are independently CH or $CR^3$. In some embodiments, $A^4$ and $A^6$ are N, and $A^2$ and $A^3$ are independently CH or $CR^3$. In some embodiments, $A^3$ and $A^6$ are N, and $A^2$ and $A^4$ are independently CH or $CR^3$.

In some embodiments, $A^1$ and $A^6$ are N. In some embodiments, $A^2$, $A^4$, $A^5$ and $A^3$ are independently CH or $CR^3$. In some embodiments, $A^4$ is N, and $A^2$, $A^5$ and $A^3$ are independently CH or $CR^3$. In some embodiments, $A^5$ is N and $A^2$, $A^4$ and $A^3$ are independently CH or $CR^3$. In some embodiments, $A^3$ is N, and $A^2$, $A^4$ and $A^5$ are independently CH or $CR^3$. In some embodiments, $A^2$ and $A^4$ are N, and $A^5$ and $A^3$ are independently CH or $CR^3$. In some embodiments, $A^2$ and $A^5$ are N, and $A^4$ and $A^3$ are independently CH or $CR^3$. In some embodiments, $A^2$ and $A^3$ are N, and $A^4$ and $A^5$ are independently CH or $CR^3$. In some embodiments, $A^4$ and $A^5$ are N, and $A^2$ and $A^3$ are independently CH or $CR^3$. In some embodiments, $A^4$ and $A^3$ are N, and $A^2$ and $A^5$ are independently CH or $CR^3$. In some embodiments, $A^5$ and $A^3$ are N, and $A^2$ and $A^4$ are independently CH or $CR^3$.

In some embodiments, $A^2$ is N. In some embodiments, $A^1$ is CH or $CR^3$. In some embodiments, $A^3$, $A^4$, $A^5$ and $A^6$ are independently CH or $CR^3$. In some embodiments, $A^3$ is N, and $A^4$, $A^5$ and $A^6$ are independently CH or $CR^3$. In some embodiments, $A^4$ is N and $A^3$, $A^5$ and $A^6$ are independently CH or $CR^3$. In some embodiments, $A^5$ is N, and $A^3$, $A^4$ and $A^6$ are independently CH or $CR^3$. In some embodiments, $A^6$ is N, and $A^3$, $A^4$, and $A^5$ are independently CH or $CR^3$. In some embodiments, $A^3$ and $A^4$ are N, and $A^5$ and $A^6$ are independently CH or $CR^3$. In some embodiments, $A^3$ and $A^5$ are N, and $A^4$ and $A^6$ are independently CH or $CR^3$. In some embodiments, $A^3$ and $A^6$ are N, and $A^4$ and $A^5$ are independently CH or $CR^3$. In some embodiments, $A^4$ and $A^5$ are N, and $A^3$ and $A^6$ are independently CH or $CR^3$. In some embodiments, $A^4$ and $A^6$ are N, and $A^3$ and $A^5$ are independently CH or $CR^3$. In some embodiments, $A^5$ and $A^6$ are N, and $A^3$ and $A^4$ are independently CH or $CR^3$.

In some embodiments, $R^1$ is phenyl. In some embodiments, $R^1$ is trifluoromethylphenyl. In some embodiments, $R^1$ is 4-trifluoromethylphenyl. In some embodiments, $R^1$ is 4-fluorophenyl. In some embodiments, $R^1$ is 4-chlorophenyl. In some embodiments, $R^1$ is 4-methylphenyl. In some embodiments, $R^1$ is pyridyl optionally substituted with 1 to 3 $R^6$.

In some embodiments, $R^2$ is phenyl optionally substituted with 1 to 4 $R^4$. In some embodiments, $R^2$ is 5-membered heteroaryl optionally substituted with 1 to 4 $R^4$. In some embodiments, $R^2$ is 6-membered heteroaryl optionally substituted with 1 to 4 $R^4$. In some embodiments, $R^2$ is phenyl substituted with 2 $R^4$. In some embodiments, $R^2$ is 5-membered heteroaryl substituted with 2 $R^4$. In some embodiments, $R^2$ is 6-membered heteroaryl substituted with 2 $R^4$. In some embodiments, $R^2$ is phenyl substituted with 1 $R^4$. In some embodiments, $R^2$ is 5-membered heteroaryl substituted with 1 $R^4$. In some embodiments, $R^2$ is 6-membered heteroaryl substituted with 1 $R^4$.

In some embodiments, $R^2$ is phenyl, chlorophenyl, methyl furan, In some embodiments, $R^2$ is selected from the group consisting of thiophene, thiazole, isoxazole, oxazole, 1,2,5-oxadiazole, pyrazole, pyrimidine and pyridazine, which are optionally substituted with methyl. In some embodiments, $R^2$ is pyridazine, isoxazole or oxazole.

In some embodiments, $R^2$ is 5- or 6-membered heteroaryl optionally substituted with 1 to 4 $R^4$, wherein the heteroaryl comprises two heteroatoms selected from N, O and S. In some embodiments, $R^2$ is 5- or 6-membered heteroaryl optionally substituted with 1 to 4 $R^4$, wherein the heteroaryl comprises two heteroatoms selected from N and S.

In some embodiments, $R^2$ is phenyl.

In some embodiments, $R^2$ is selected from the group consisting of:

In some embodiments, $R^2$ is

In some embodiments, $R^2$ is

In some embodiments, $R^2$ is

In some embodiments of Formula VIIIa, VIIIb or VIIIc, $R^2$ is ethyl or isopropyl. In some embodiments of Formula VIIIa, VIIIb or VIIIc, $R^2$ is In some embodiments, $R^2$ is $R^5$ optionally substituted with 1 to 4 $R^4$, wherein $R^5$ is selected from the group consisting of furan, benzofuran, pyridine, pyridazine, pyrimidine, pyrazine, thiophene, thiazole, isothiazole, oxazole, isoxazole, oxadiazole, imidazole, pyrrole, and pyrazole. In some embodiments, $R^2$ is $R^5$ substituted with 1 $R^4$. In some embodiments, $R^2$ is $R^5$ substituted with 2 $R^4$. In some embodiments, $R^2$ is $R^5$ substituted with 3 $R^4$. In some embodiments, $R^2$ is $R^5$ substituted with 4 $R^4$.

In some embodiments, $R^4$ is selected from the group consisting of lower alkyl (such as methyl), halo, lower haloalkyl, —OH, —OR¹⁰, cyano and phenyl optionally substituted methyl, wherein $R^7$ is lower alkyl or lower haloalkyl.

In some embodiments, m is 0. In some embodiments, m is 1. In some embodiments, $R^3$ is halo. In some embodiments, $R^3$ is lower alkyl.

In some embodiments, n is 1.

In some embodiments, $R^6$ is trifluoromethyl. In some embodiments, $R^6$ is fluoro. In some embodiments, $R^6$ is chloro. In some embodiments, $R^6$ is methyl. In some embodiments, $R^6$ is cyano. In some embodiments, $R^6$ is 4-trifluoromethyl. In some embodiments, $R^6$ is 4-fluoro. In some embodiments, $R^6$ is 4-chloro. In some embodiments, $R^6$ is 4-methyl. In some embodiments, $R^6$ is 4-cyano.

In some embodiments, the metastasis inhibitor is a compound is selected from

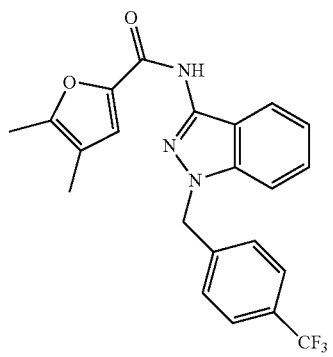

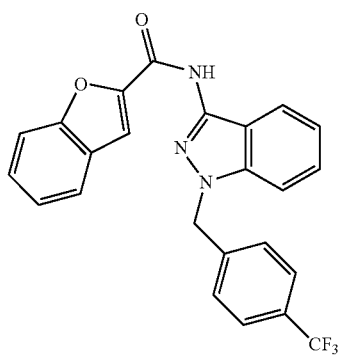

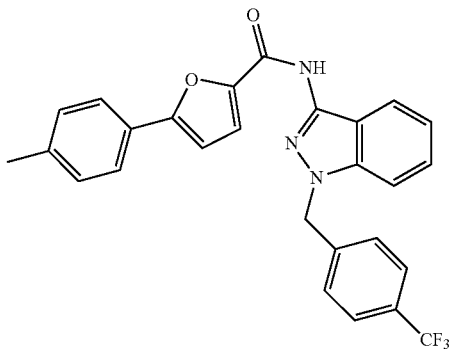

-continued

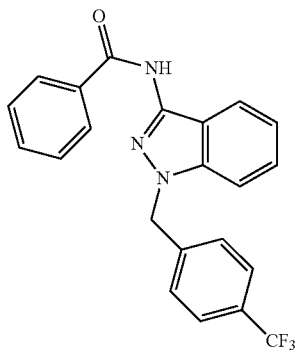

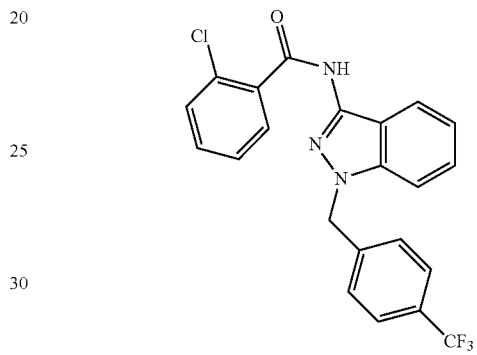

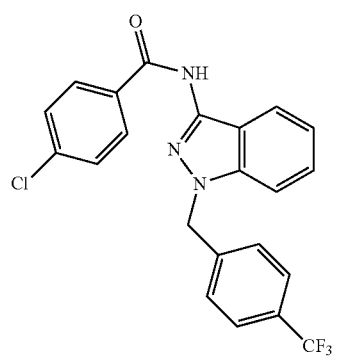

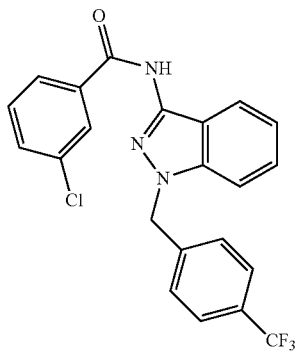

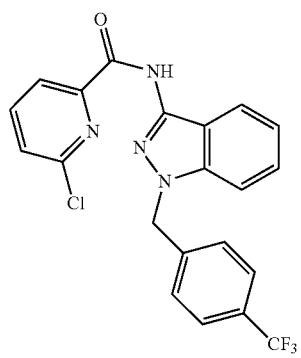
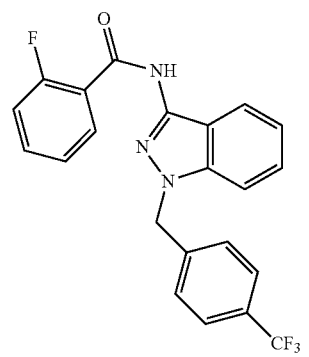
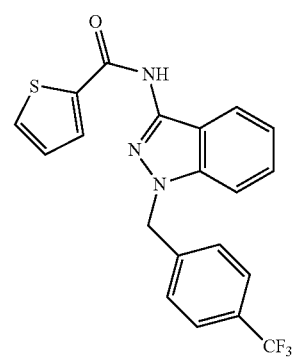
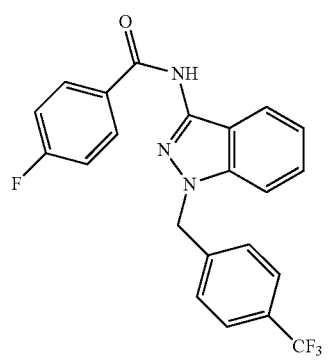
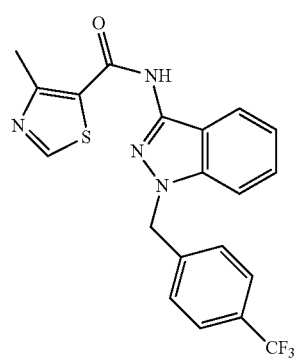
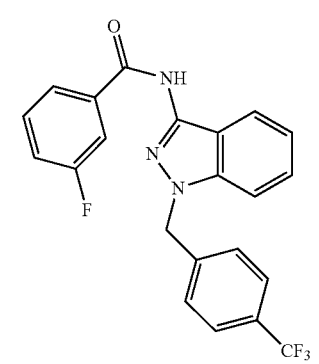
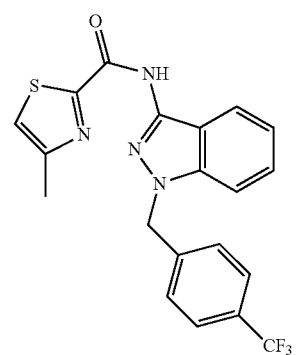
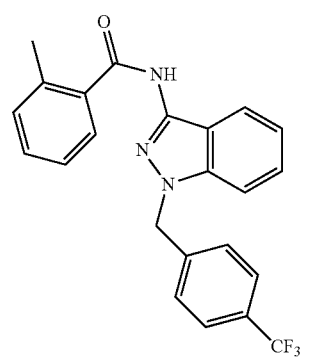

-continued
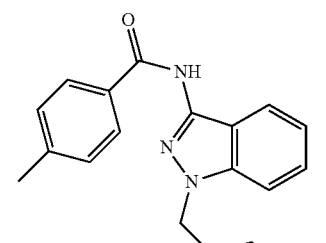
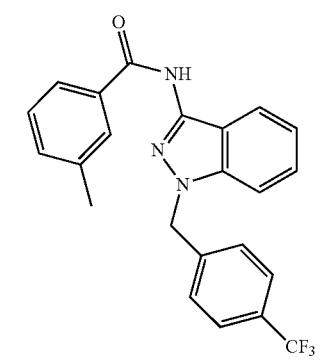
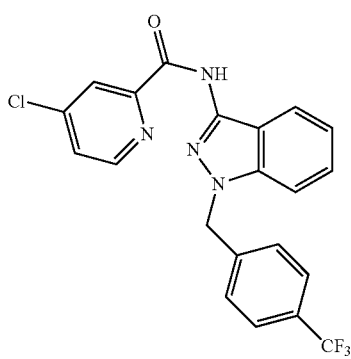
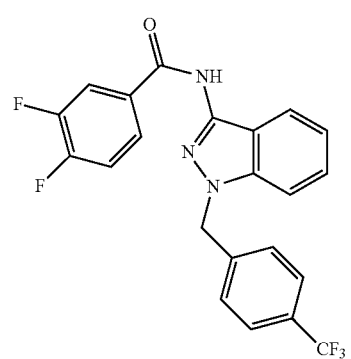
-continued
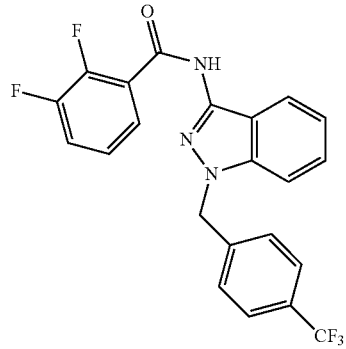
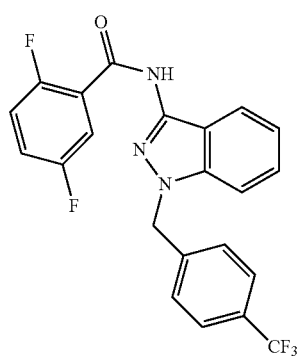
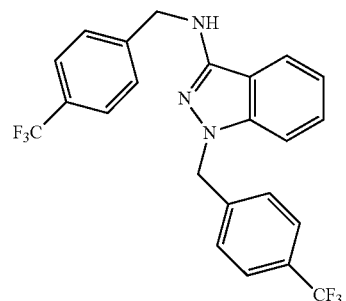
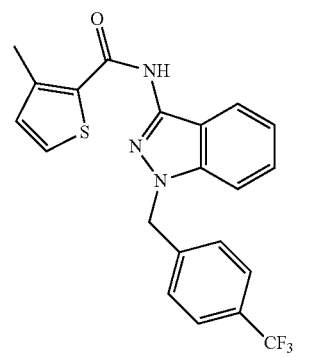
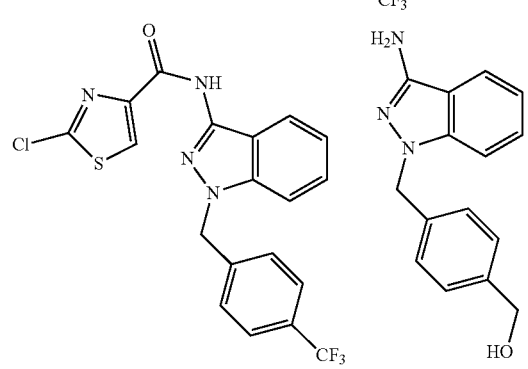

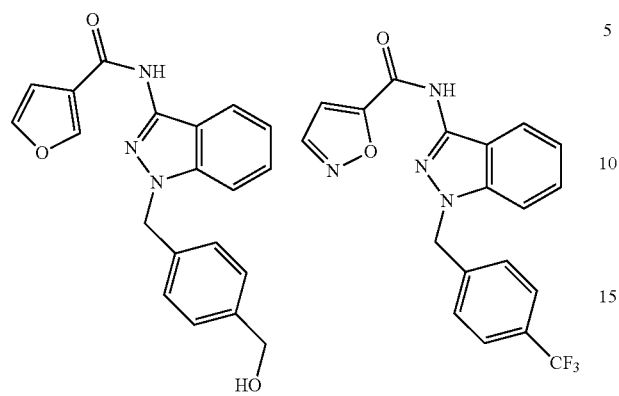
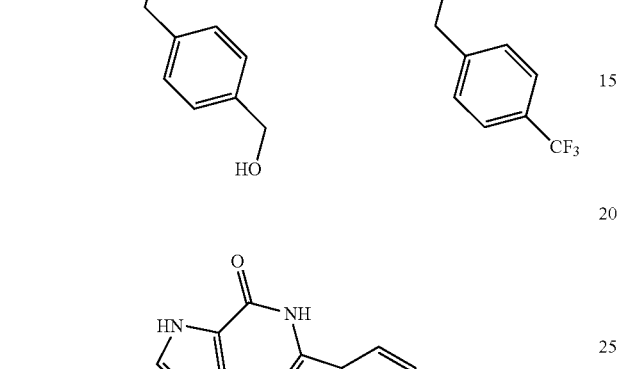
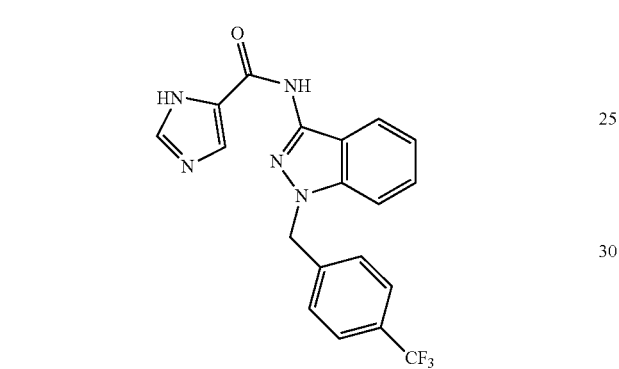
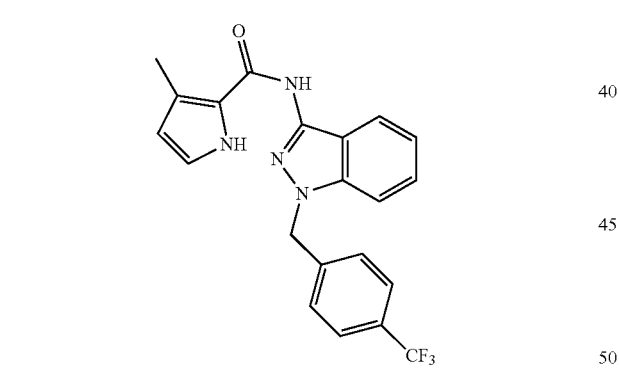
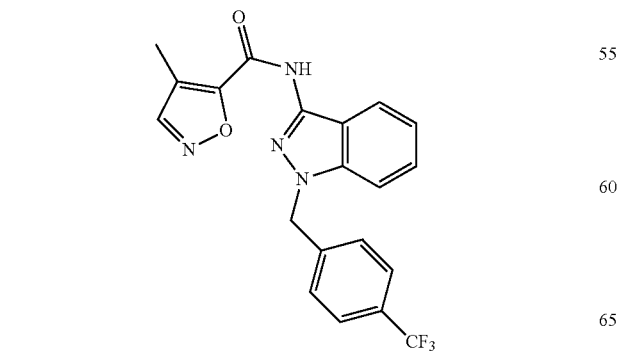

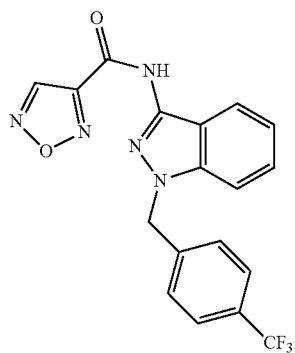
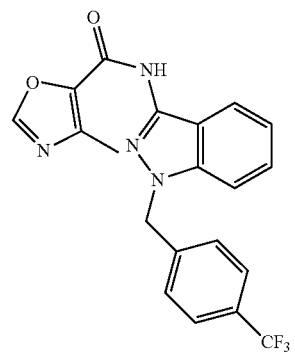
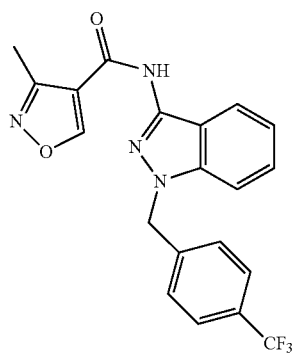
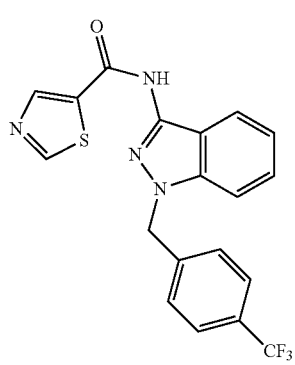
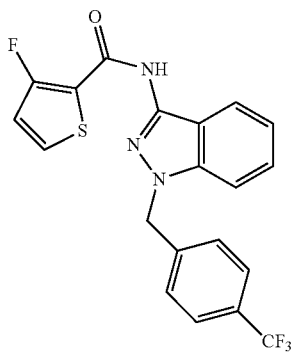
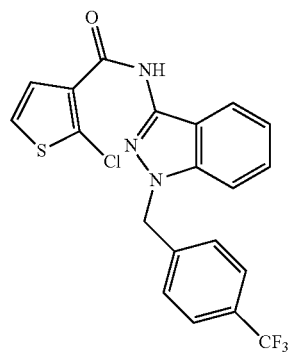
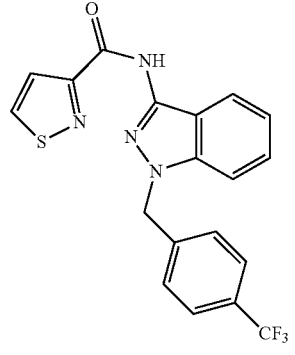
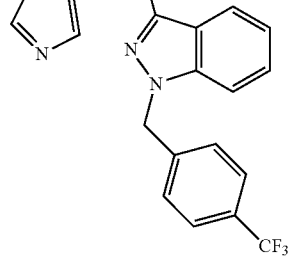

-continued
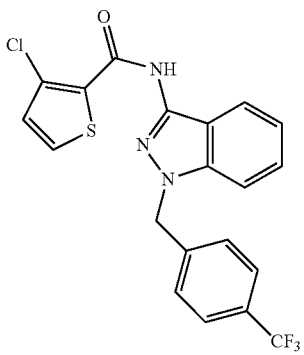
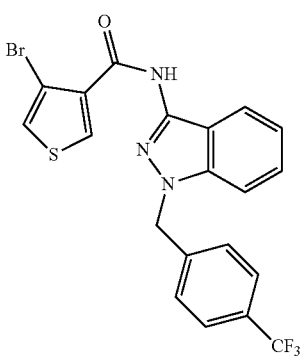
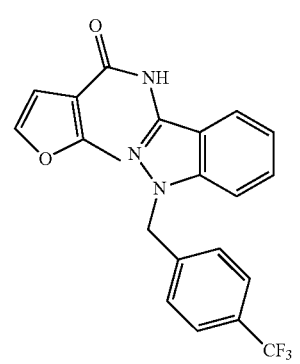
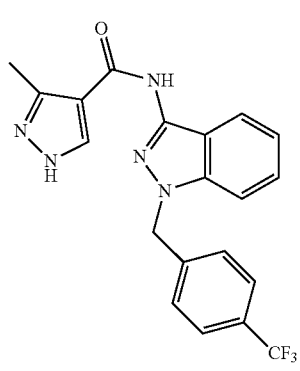
-continued
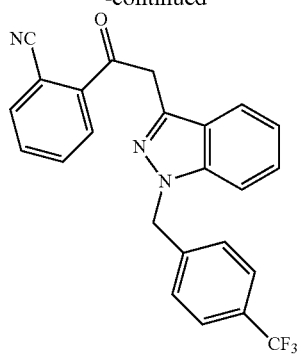
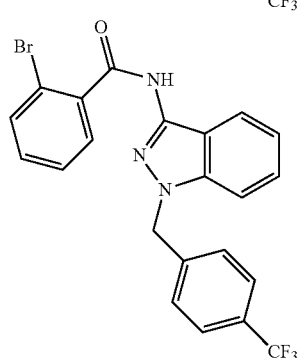
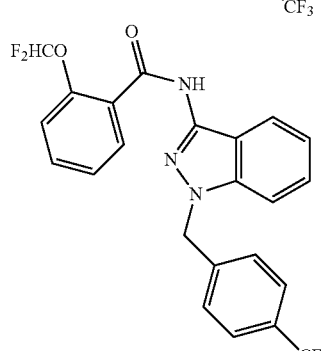
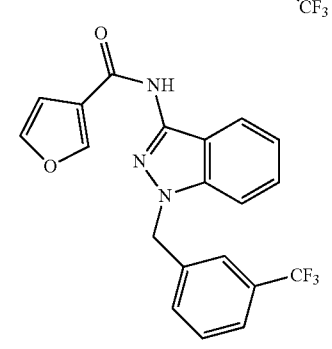
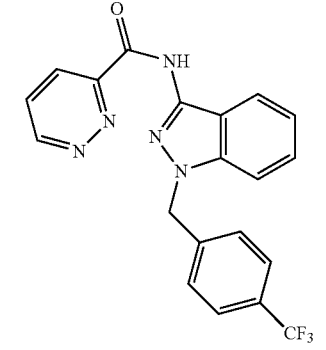

-continued
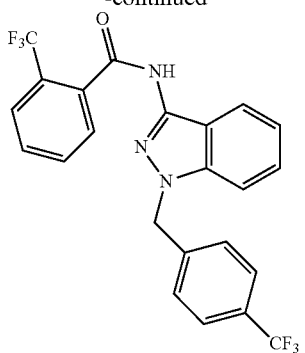
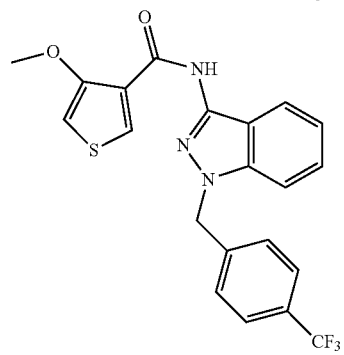
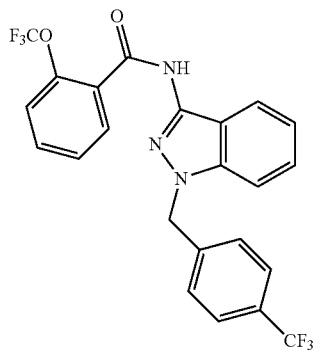
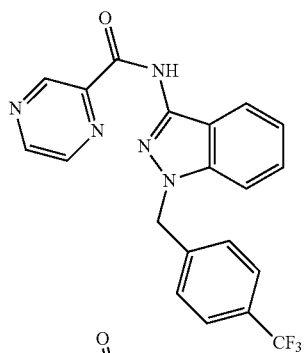
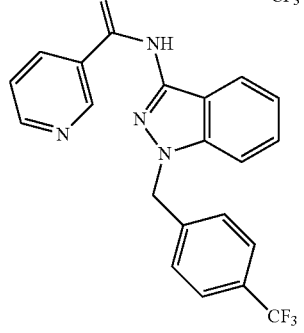
-continued
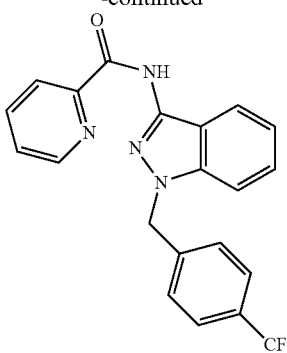
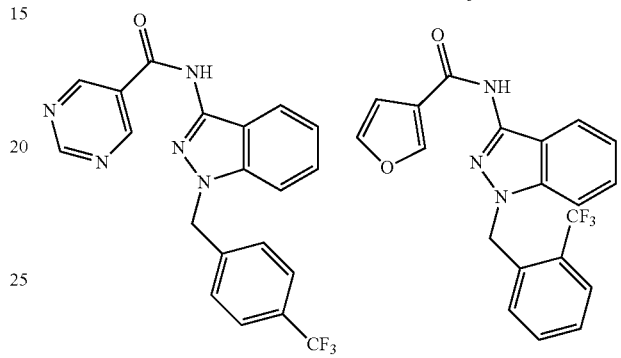
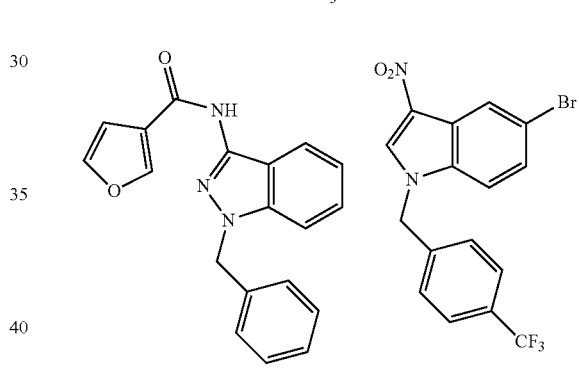
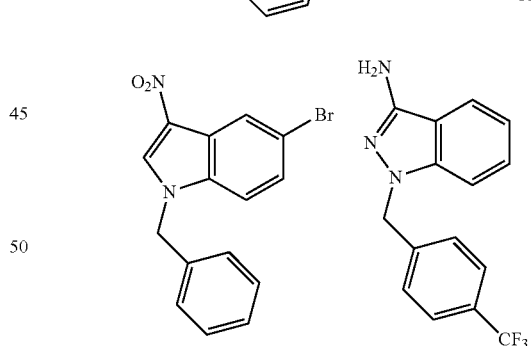
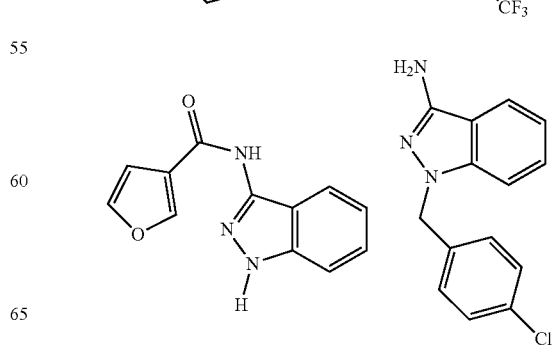

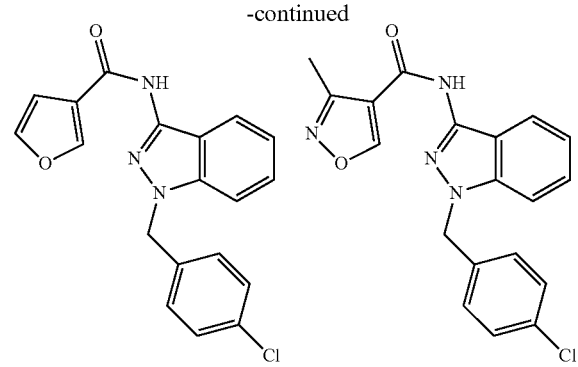
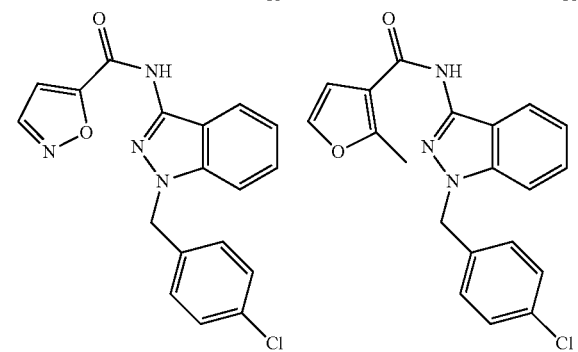
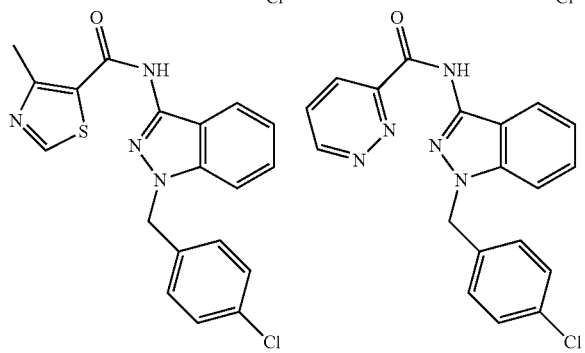
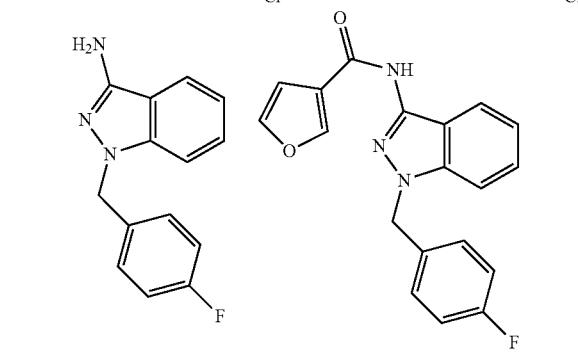
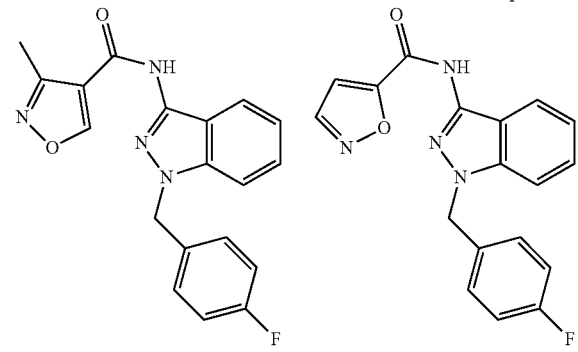
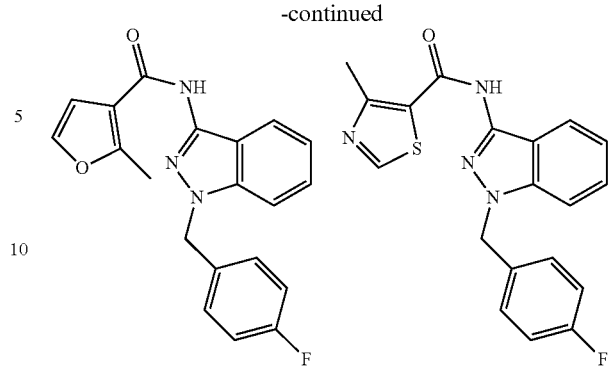
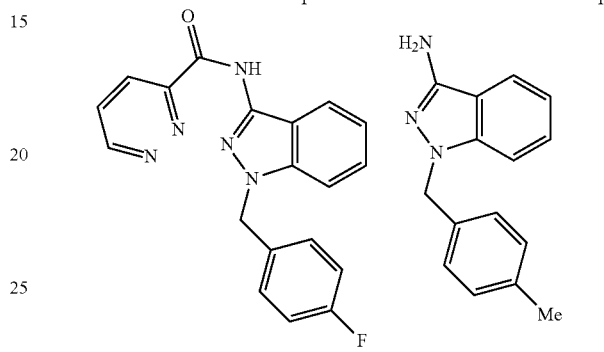
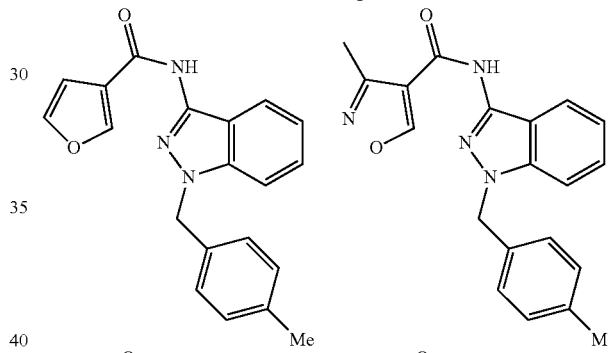
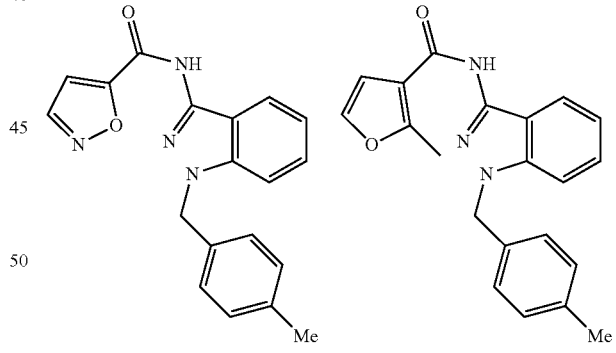
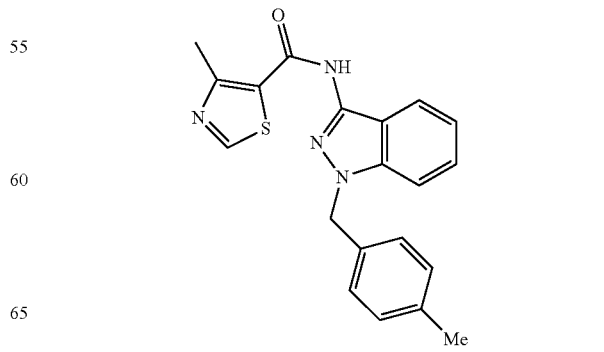

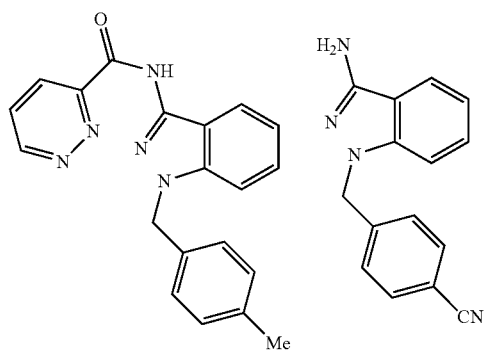
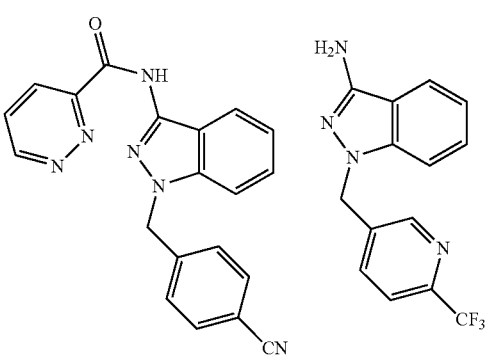
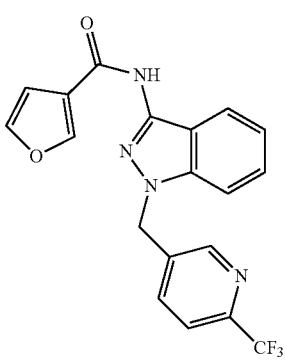
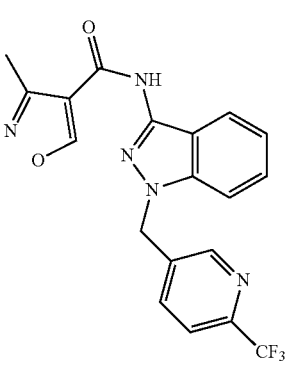
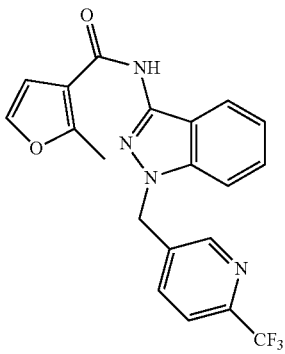

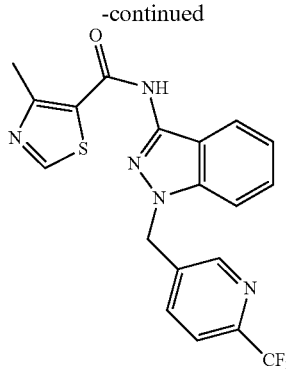
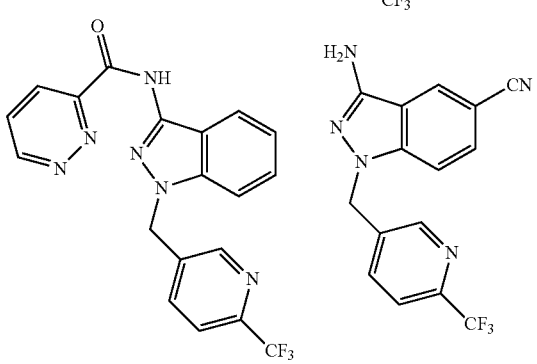
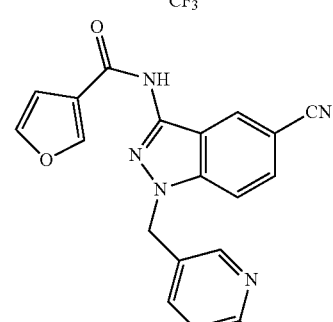
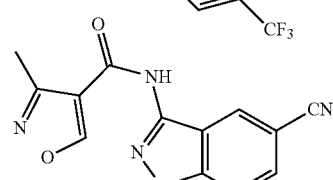
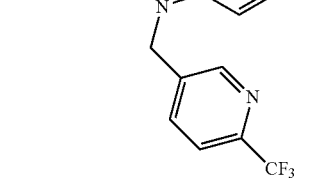
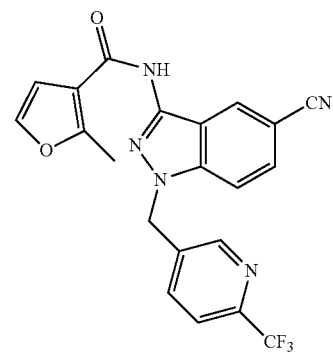
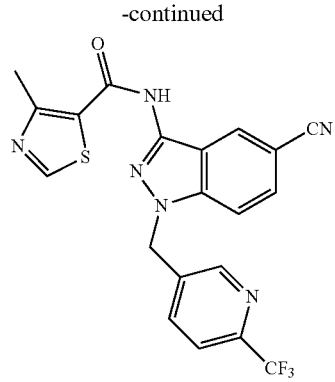
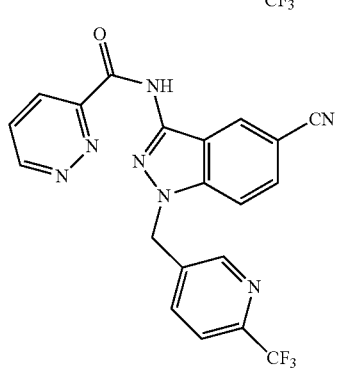
or a tautomer, and/or pharmaceutically acceptable salt thereof.
In some embodiments, the group
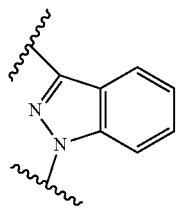 [SMILES: *c1nn(*)c2ccccc12]
in any of the above compounds is replaced with
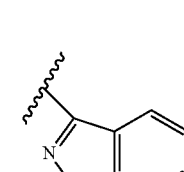
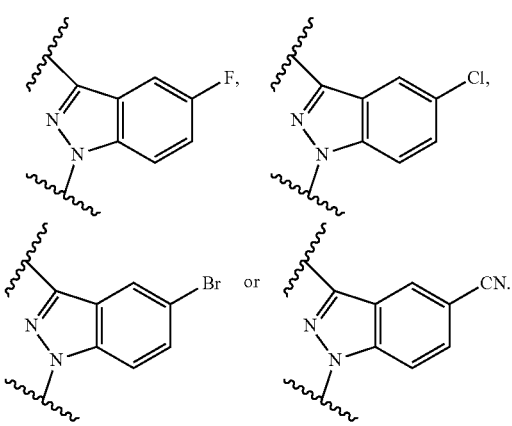
In some embodiments, the metastasis inhibitor is a compound is selected from 51
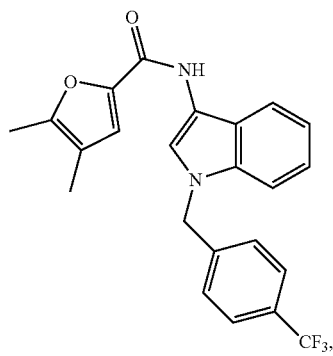
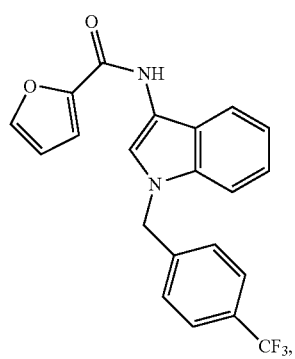
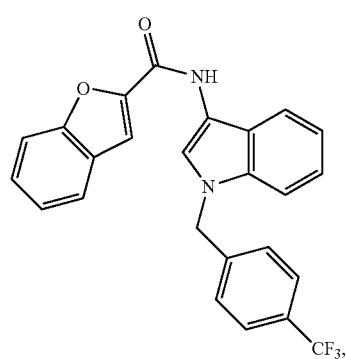
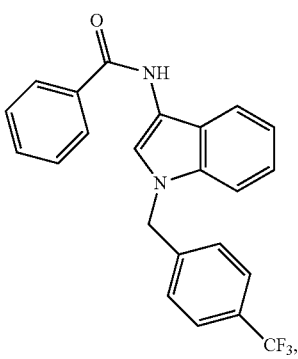
52
-continued
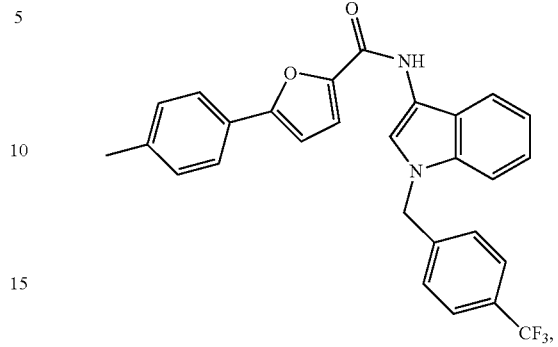
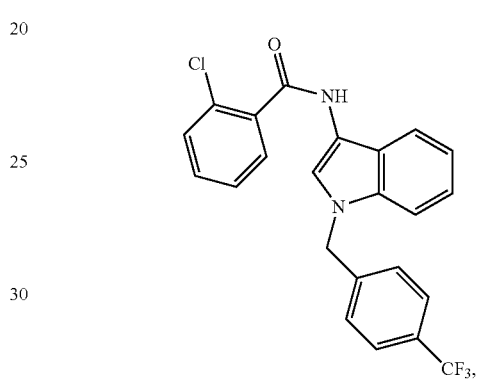
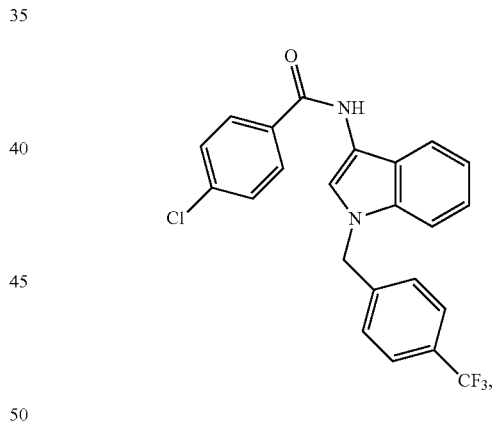
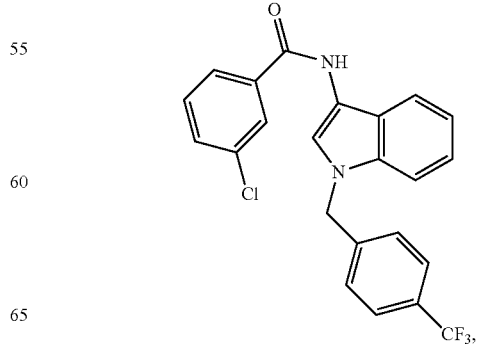

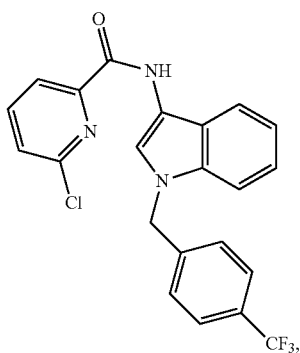
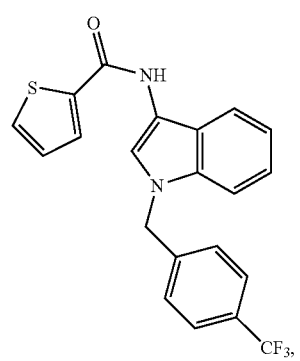
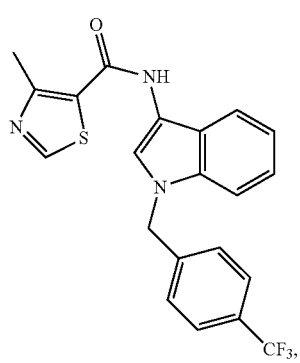
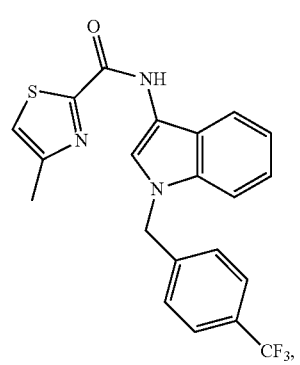
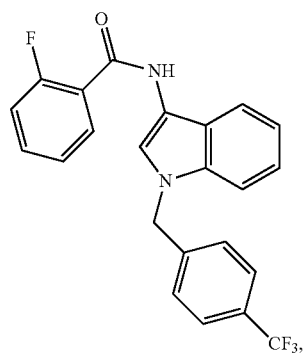
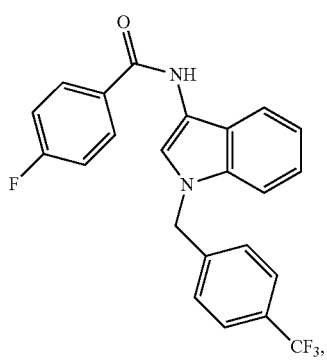
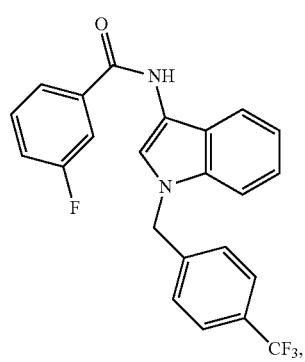
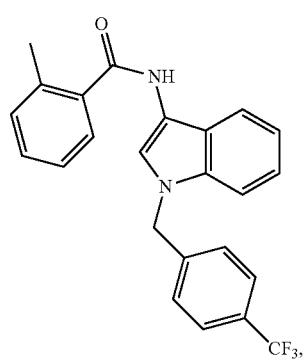

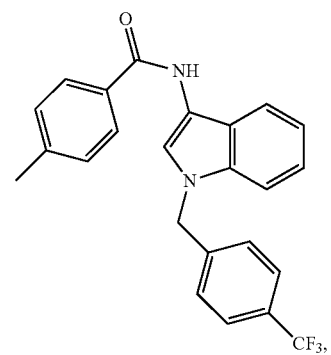
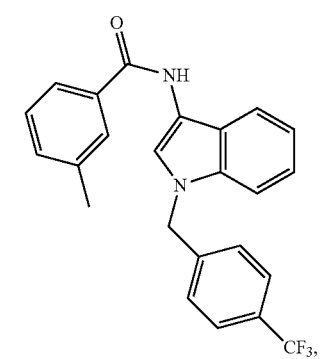
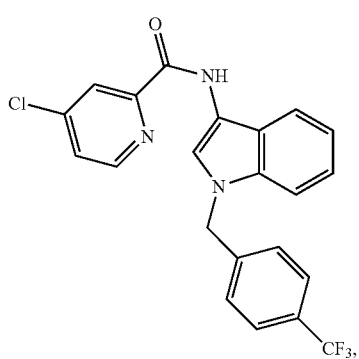
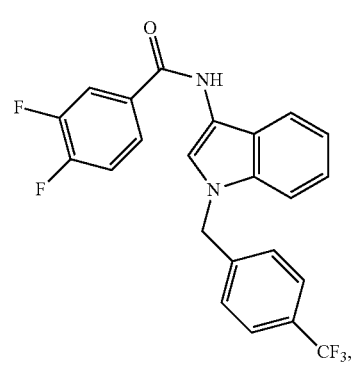
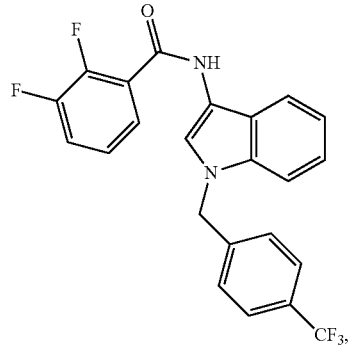
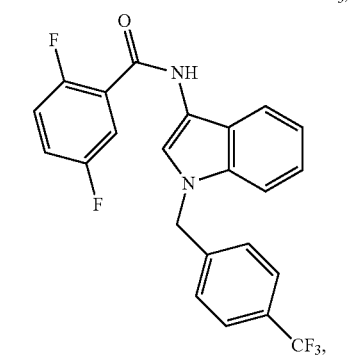
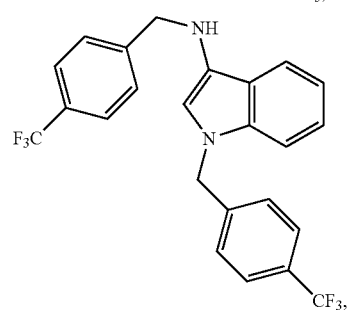
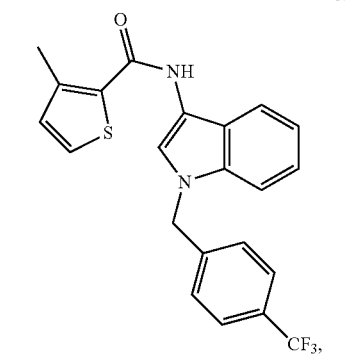
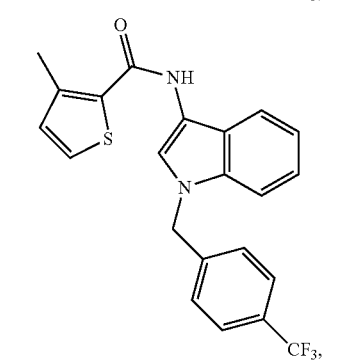

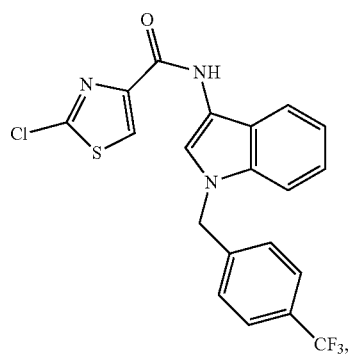
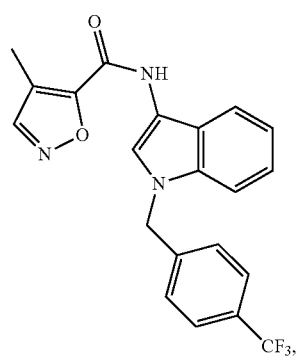
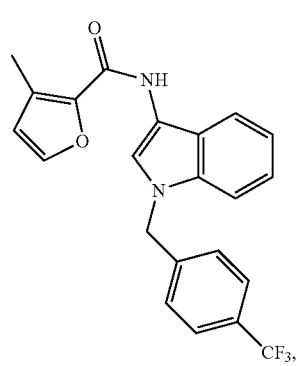
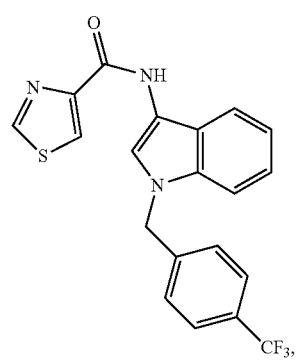
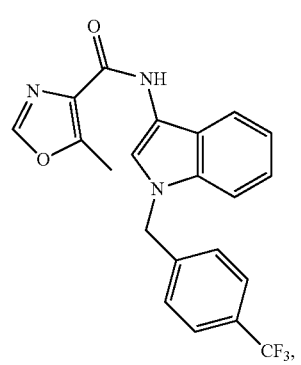

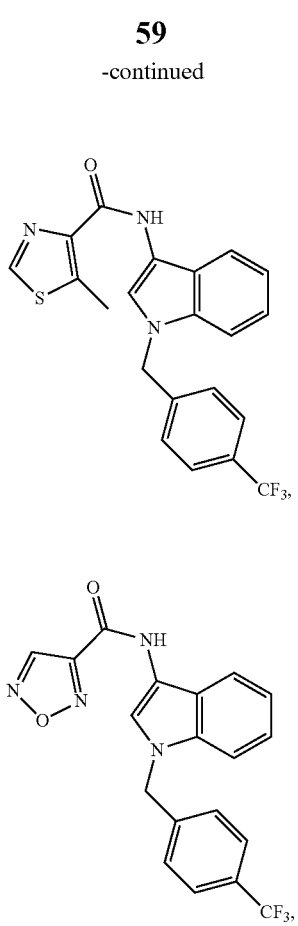
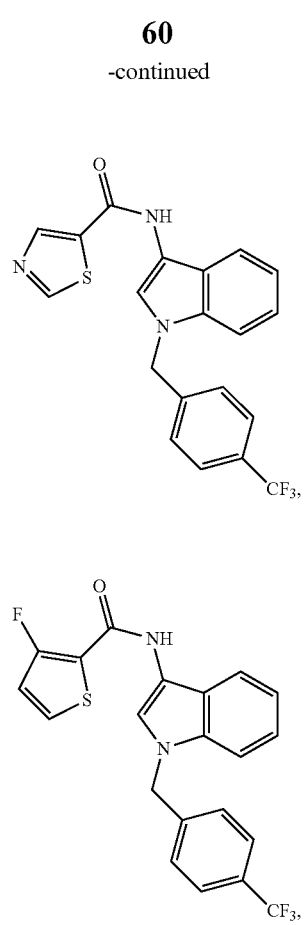

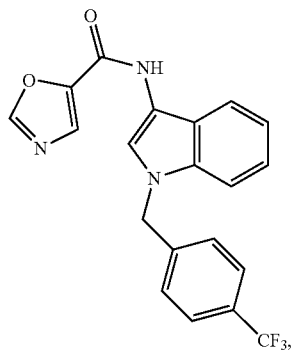
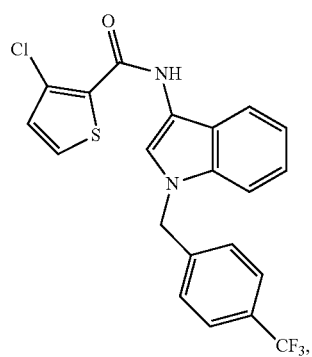
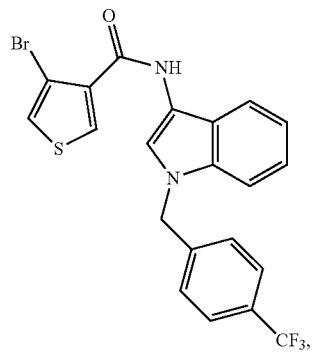
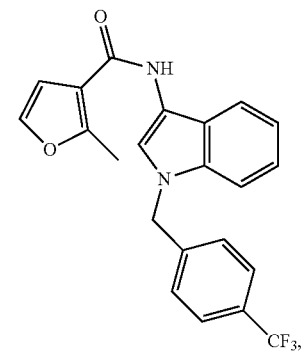
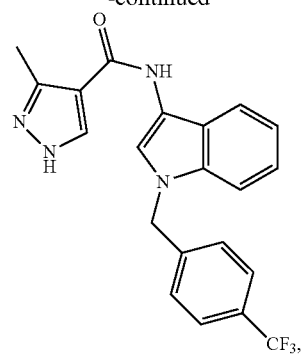
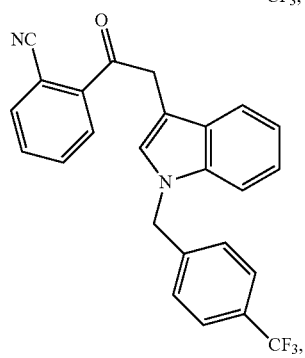
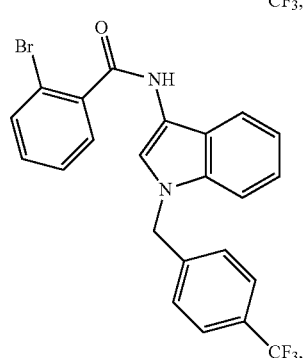
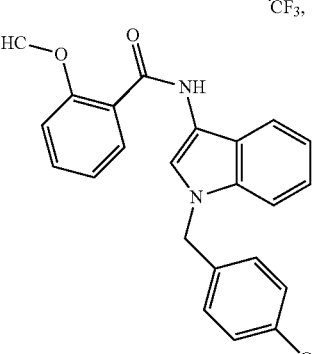
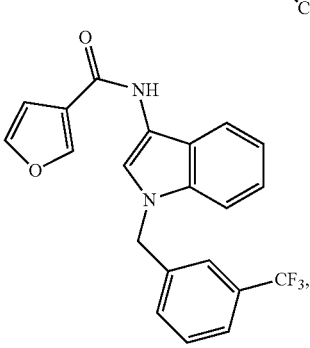

-continued
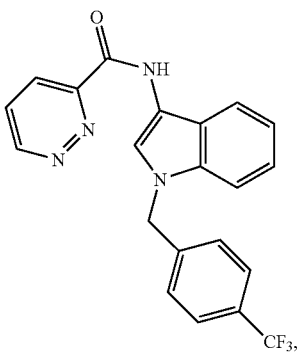
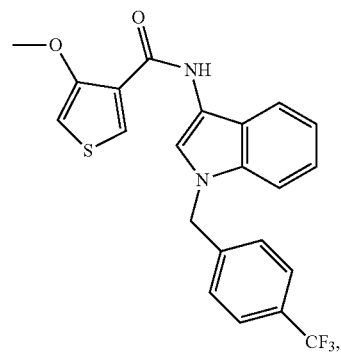
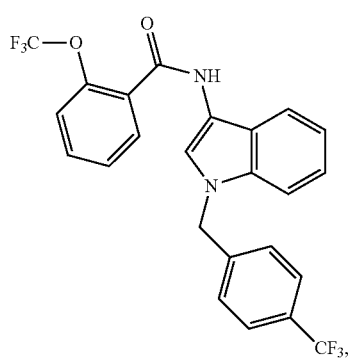
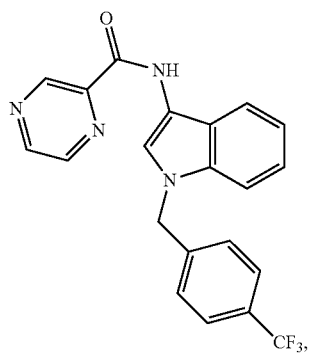
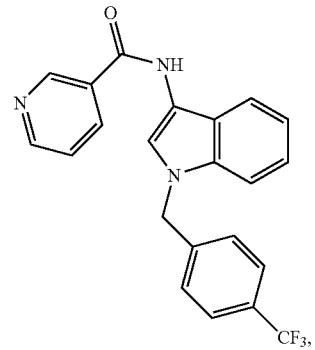
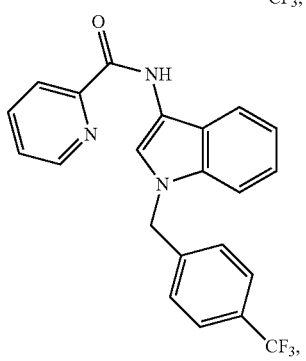
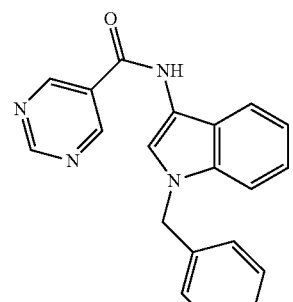
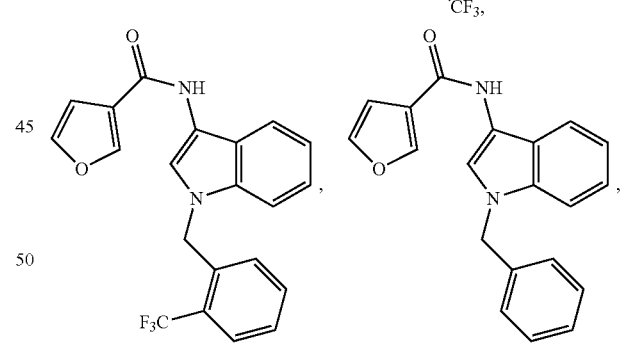
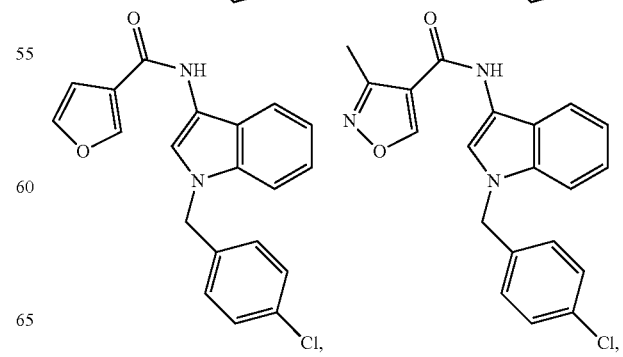

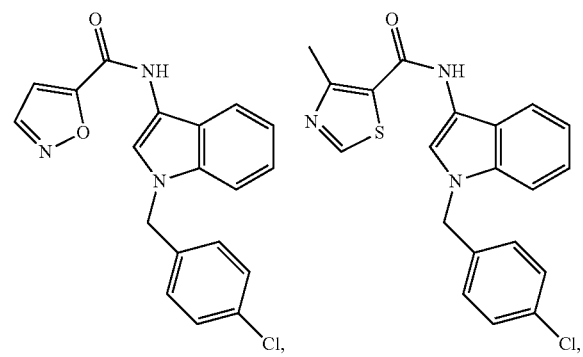
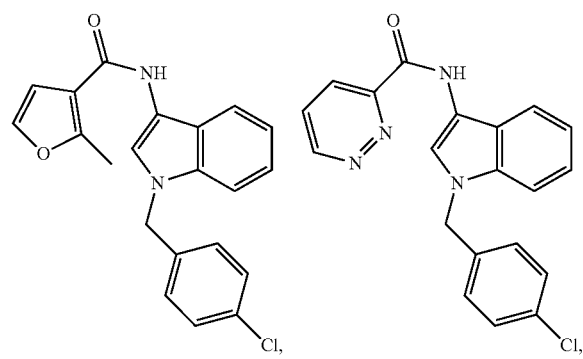
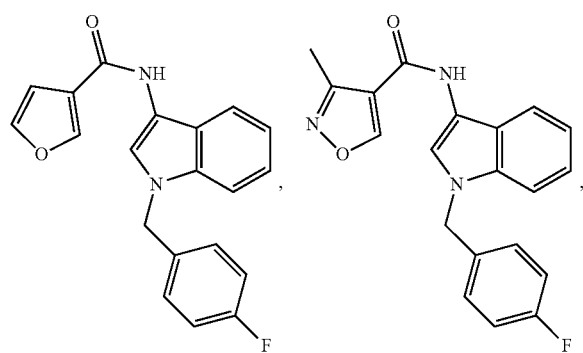
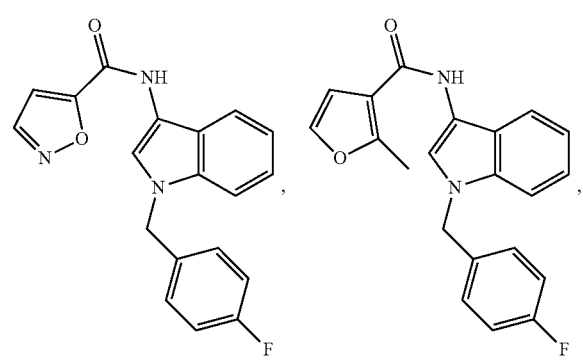
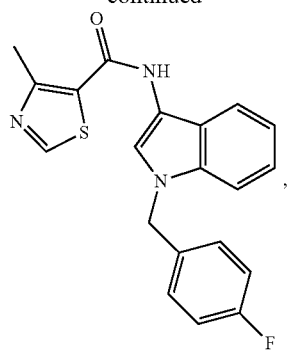
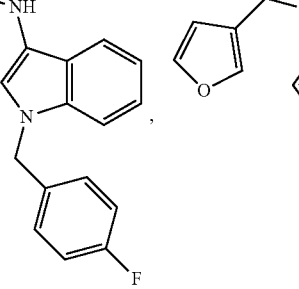
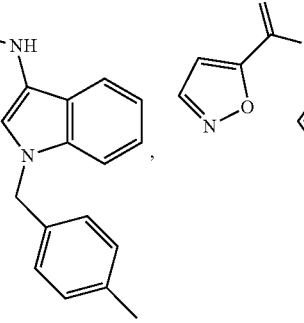
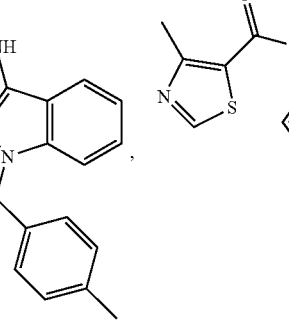
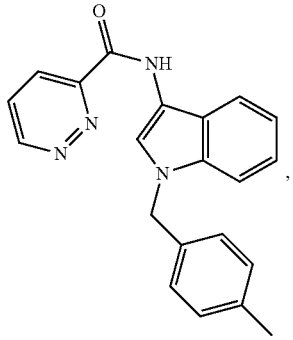

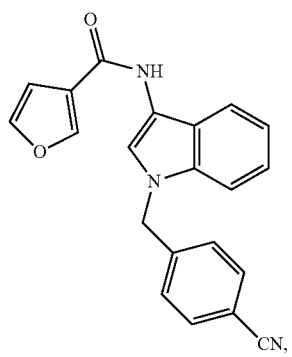
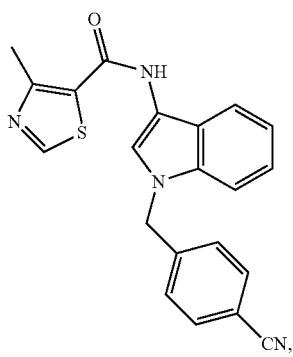
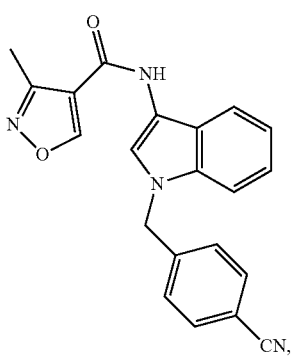
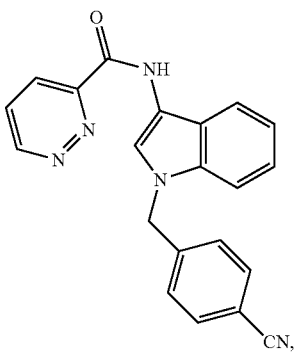
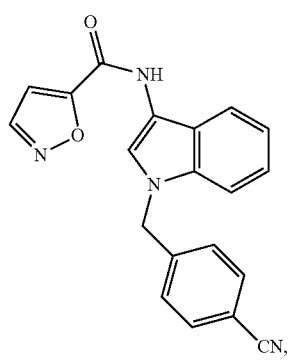
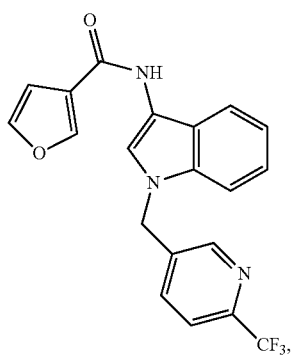
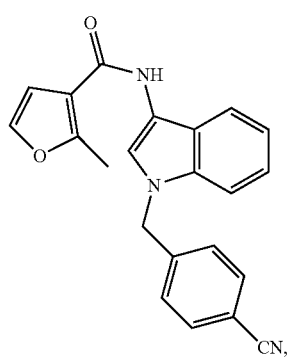
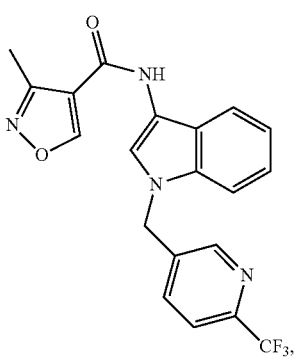

69
-continued
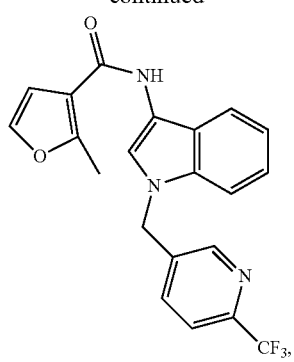
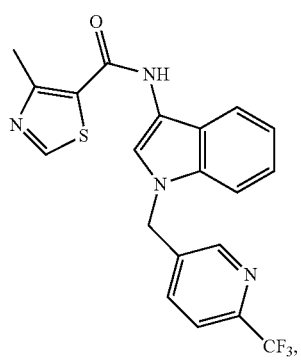
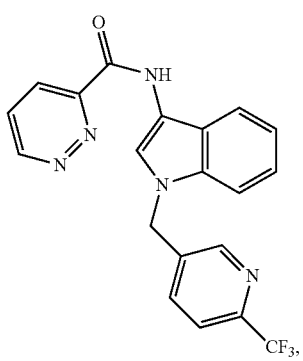
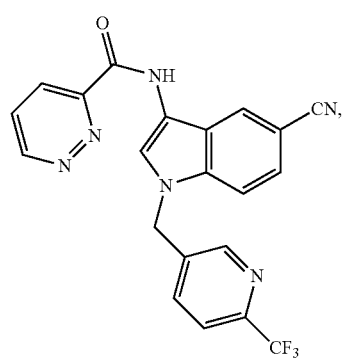
70
-continued
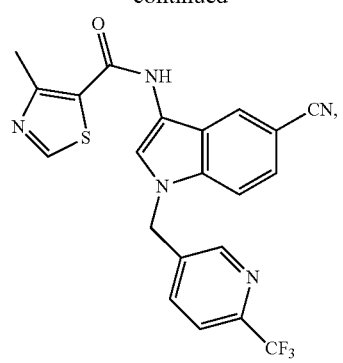
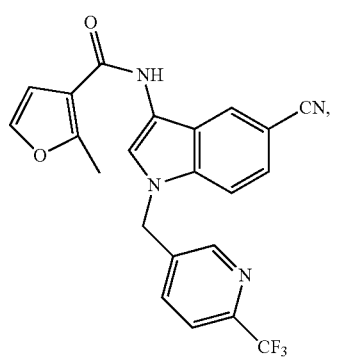
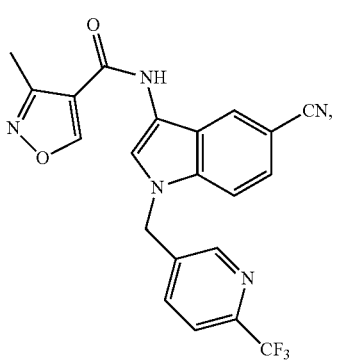
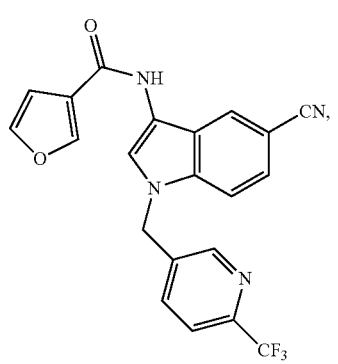

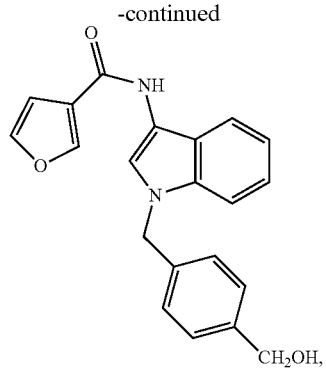

or a tautomer, and/or pharmaceutically acceptable salt thereof.

In some embodiments, the group

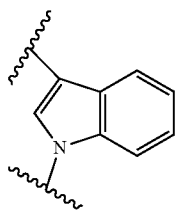 [SMILES: *c1cn(*)c2ccccc12]

in any of the above compounds is replaced with

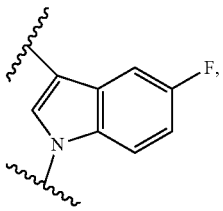 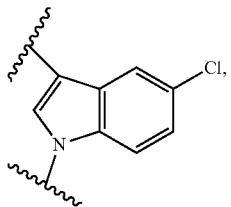

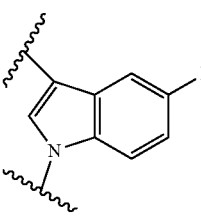 or 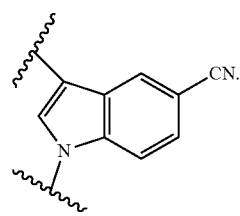

In some embodiments, the metastasis inhibitor is a compound selected from Table 2 or a tautomer, and/or pharmaceutically acceptable salt thereof:

TABLE 2

| Compound | Structure | Name |
|---|---|---|
| 4 | 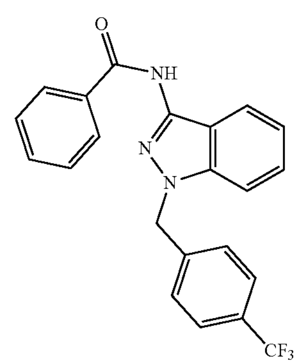 [SMILES: O=C(Nc1nn(Cc2ccc(C(F)(F)F)cc2)c2ccccc12)c1ccccc1] | N-(1-(4-(trifluoromethyl)benzyl)-1H-indazol-3-yl)benzamide |
| 5 | 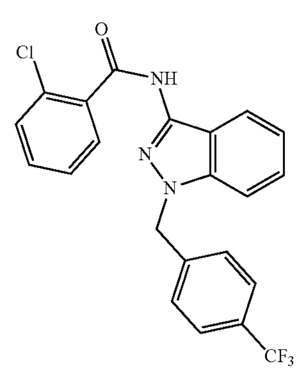 [SMILES: O=C(Nc1nn(Cc2ccc(C(F)(F)F)cc2)c2ccccc12)c1ccccc1Cl] | 2-chloro-N-(1-(4-(trifluoromethyl)benzyl)-1H-indazol-3-yl)benzamide |

TABLE 2-continued

| Compound | Structure | Name |
|---|---|---|
| 9 | 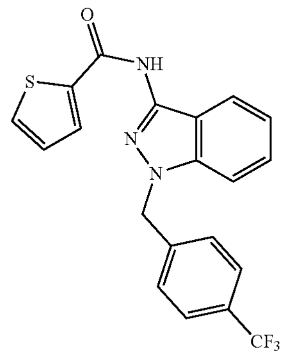 [SMILES: O=C(Nc1nn(Cc2ccc(C(F)(F)F)cc2)c2ccccc12)c1cccs1] | N-(1-(4-(trifluoromethyl)benzyl)-1H-indazol-3-yl)thiophene-2-carboxamide |
| 10 | 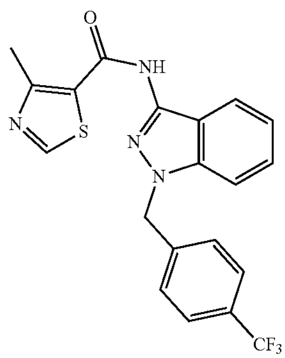 [SMILES: Cc1ncsc1C(=O)Nc1nn(Cc2ccc(C(F)(F)F)cc2)c2ccccc12] | 4-methyl-N-(1-(4-(trifluoromethyl)benzyl)-1H-indazol-3-yl)thiazole-5-carboxamide |
| 25 | 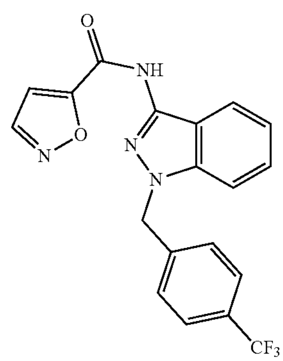 [SMILES: O=C(Nc1nn(Cc2ccc(C(F)(F)F)cc2)c2ccccc12)c1ccno1] | N-(1-(4-(trifluoromethyl)benzyl)-1H-indazol-3-yl)isoxazole-5-carboxamide |
| 28 | 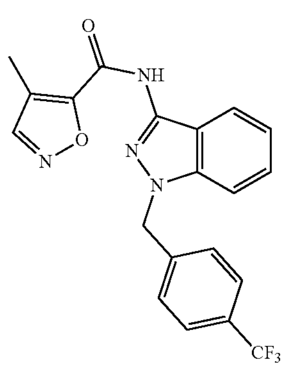 [SMILES: Cc1cnoc1C(=O)Nc1nn(Cc2ccc(C(F)(F)F)cc2)c2ccccc12] | 4-methyl-N-(1-(4-(trifluoromethyl)benzyl)-1H-indazol-3-yl)isoxazole-5-carboxamide |

TABLE 2-continued

| Compound | Structure | Name |
|---|---|---|
| 31 | 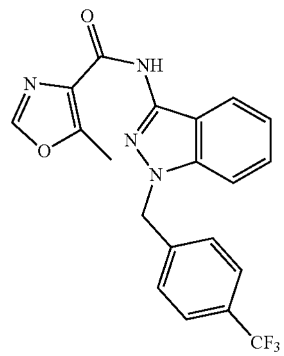 [SMILES: Cc1ocnc1C(=O)Nc1nn(Cc2ccc(C(F)(F)F)cc2)c2ccccc12] | 5-methyl-N-(1-(4-(trifluoromethyl)benzyl)-1H-indazol-3-yl)oxazole-4-carboxamide |
| 33 | 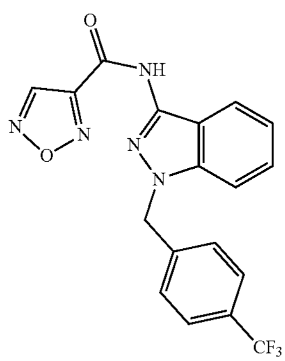 [SMILES: O=C(Nc1nn(Cc2ccc(C(F)(F)F)cc2)c2ccccc12)c1cnon1] | N-(1-(4-(trifluoromethyl)benzyl)-1H-indazol-3-yl)-1,2,5-oxadiazole-3-carboxamide |
| 34 | 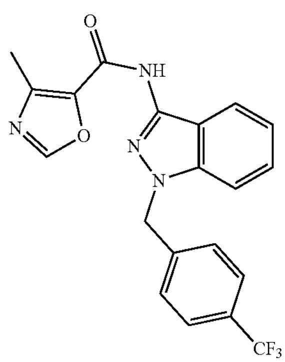 [SMILES: Cc1ncoc1C(=O)Nc1nn(Cc2ccc(C(F)(F)F)cc2)c2ccccc12] | 4-methyl-N-(1-(4-(trifluoromethyl)benzyl)-1H-indazol-3-yl)oxazole-5-carboxamide |
| 35 | 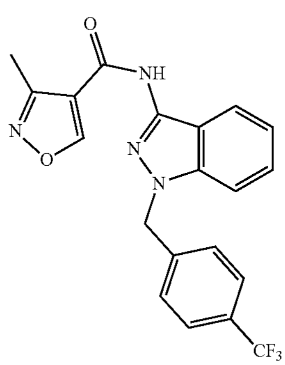 [SMILES: Cc1nocc1C(=O)Nc1nn(Cc2ccc(C(F)(F)F)cc2)c2ccccc12] | 3-methyl-N-(1-(4-(trifluoromethyl)benzyl)-1H-indazol-3-yl)isoxazole-4-carboxamide |

TABLE 2-continued

| Compound | Structure | Name |
| --- | --- | --- |
| 36 | 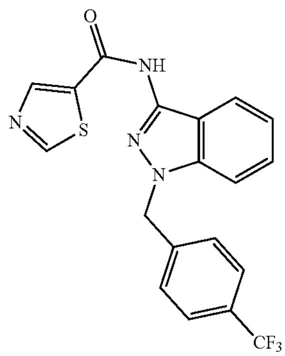 [SMILES: O=C(Nc1nn(Cc2ccc(C(F)(F)F)cc2)c2ccccc12)c1cncs1] | N-(1-(4-(trifluoromethyl)benzyl)-1H-indazol-3-yl)thiazole-5-carboxamide |
| 39 | 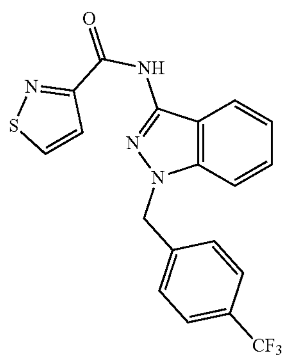 [SMILES: O=C(Nc1nn(Cc2ccc(C(F)(F)F)cc2)c2ccccc12)c1ccsn1] | N-(1-(4-(trifluoromethyl)benzyl)-1H-indazol-3-yl)isothiazole-3-carboxamide |
| 40 | 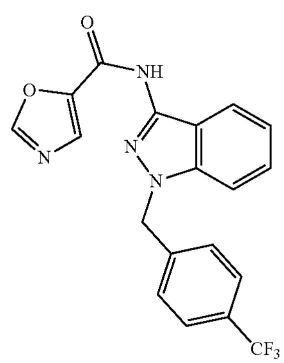 | N-(1-(4-(trifluoromethyl)benzyl)-1H-indazol-3-yl)oxazole-5-carboxamide |
| 43 | 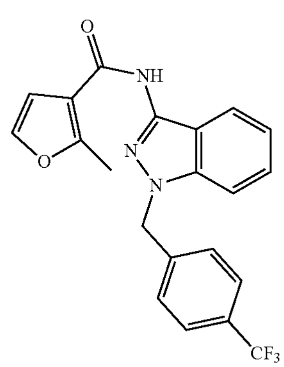 [SMILES: Cc1occc1C(=O)Nc1nn(Cc2ccc(C(F)(F)F)cc2)c2ccccc12] | 2-methyl-N-(1-(4-(trifluoromethyl)benzyl)-1H-indazol-3-yl)furan-3-carboxamide |

TABLE 2-continued

| Compound | Structure | Name |
|---|---|---|
| 44 | 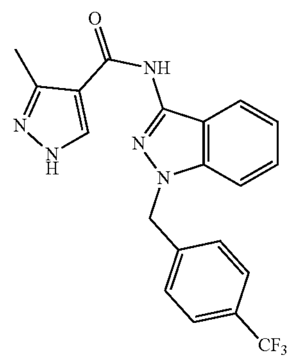 [SMILES: Cc1n[nH]cc1C(=O)Nc1nn(Cc2ccc(C(F)(F)F)cc2)c2ccccc12] | 3-methyl-N-(1-(4-(trifluoromethyl)benzyl)-1H-indazol-3-yl)-1H-pyrazole-4-carboxamide |
| 49 | 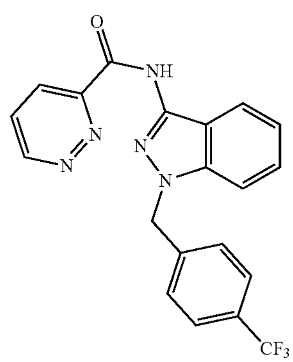 [SMILES: O=C(Nc1nn(Cc2ccc(C(F)(F)F)cc2)c2ccccc12)c1cccnn1] | N-(1-(4-(trifluoromethyl)benzyl)-1H-indazol-3-yl)pyridazine-3-carboxamide |
| 56 | 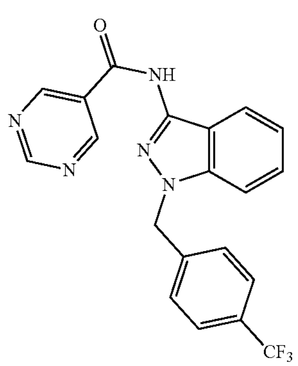 [SMILES: O=C(Nc1nn(Cc2ccc(C(F)(F)F)cc2)c2ccccc12)c1cncnc1] | N-(1-(4-(trifluoromethyl)benzyl)-1H-indazol-3-yl)pyrimidine-5-carboxamide |
| 64 | 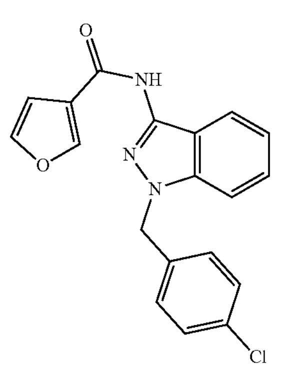 [SMILES: O=C(Nc1nn(Cc2ccc(Cl)cc2)c2ccccc12)c1ccoc1] | N-(1-(4-chlorobenzyl)-1H-indazol-3-yl)furan-3-carboxamide |

TABLE 2-continued
| Compound | Structure | Name |
|---|---|---|
| 65 | 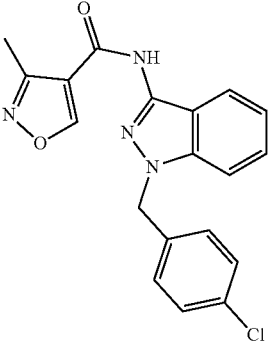 [SMILES: Cc1nocc1C(=O)Nc1nn(Cc2ccc(Cl)cc2)c2ccccc12] | N-(1-(4-chlorobenzyl)-1H-indazol-3-yl)-3-methyl-isoxazole-4-carboxamide |
| 66 | 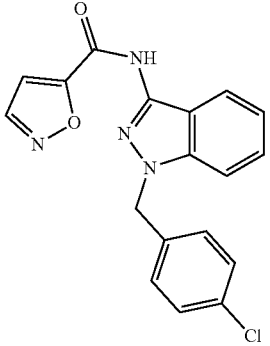 [SMILES: O=C(Nc1nn(Cc2ccc(Cl)cc2)c2ccccc12)c1ccno1] | N-(1-(4-chlorobenzyl)-1H-indazol-3-yl)isoxazole-5-carboxamide |
| 67 | 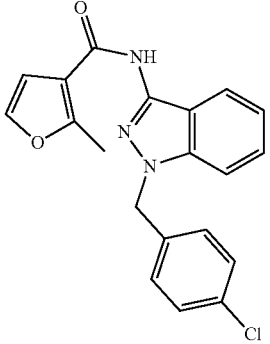 [SMILES: Cc1occc1C(=O)Nc1nn(Cc2ccc(Cl)cc2)c2ccccc12] | N-(1-(4-chlorobenzyl)-1H-indazol-3-yl)-2-methyl-furan-3-carboxamide |
| 68 | 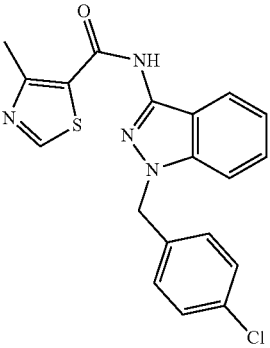 [SMILES: Cc1ncsc1C(=O)Nc1nn(Cc2ccc(Cl)cc2)c2ccccc12] | N-(1-(4-chlorobenzyl)-1H-indazol-3-yl)-4-methyl-thiazole-5-carboxamide |

TABLE 2-continued

| Compound | Structure | Name |
| --- | --- | --- |
| 69 | 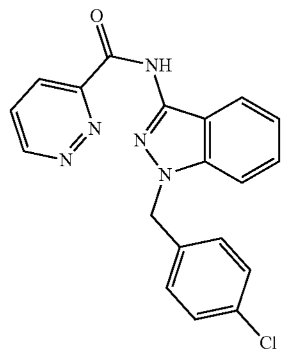 [SMILES: O=C(Nc1nn(Cc2ccc(Cl)cc2)c2ccccc12)c1cccnn1] | N-(1-(4-chlorobenzyl)-1H-indazol-3-yl)pyridazine-3-carboxamide |
| 73 | 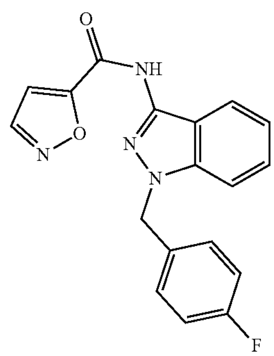 [SMILES: O=C(Nc1nn(Cc2ccc(F)cc2)c2ccccc12)c1ccno1] | N-(1-(4-fluorobenzyl)-1H-indazol-3-yl)isoxazole-5-carboxamide |
| 80 | 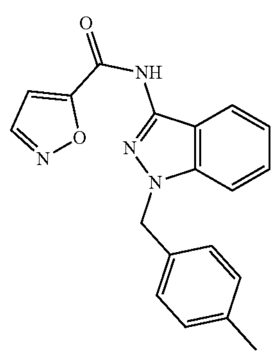 [SMILES: Cc1ccc(Cn2nc(NC(=O)c3ccno3)c3ccccc32)cc1] | N-(1-(4-methylbenzyl)-1H-indazol-3-yl)isoxazole-5-carboxamide |
| 137 | 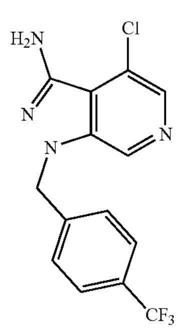 [SMILES: N=C(N)c1c(Cl)cncc1NCc1ccc(C(F)(F)F)cc1] | 4-chloro-1-(4-(trifluoromethyl)benzyl)-1H-pyrazolo[3,4-c]pyridin-3-amine |

TABLE 2-continued

| Compound | Structure | Name |
|---|---|---|
| 138 | 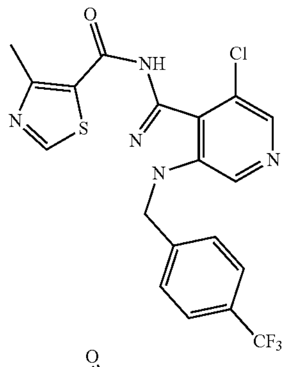 | N-(4-chloro-1-(4-(trifluoro-methyl)benzyl)-1H-pyrazolo[3,4-c]pyridin-3-yl)-4-methylthiazole-5-carboxamide |
| 139 | 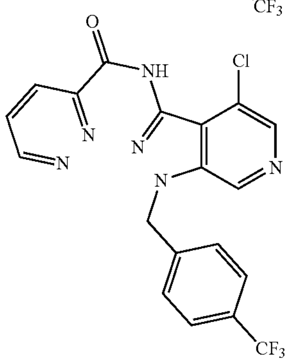 | N-(4-chloro-1-(4-(trifluoro-methyl)benzyl)-1H-pyrazolo[3,4-c]pyridin-3-yl)pyridazine-3-carboxamide |
| 151 | 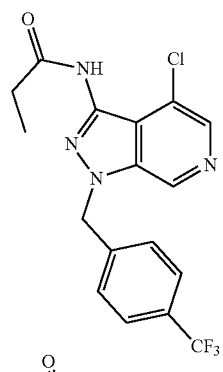 | N-(4-chloro-2-(4-(trifluoro-methyl)benzyl)-1H-pyrazolo[3,4-c]pyridin-3-yl)propionamide |
| 152 | 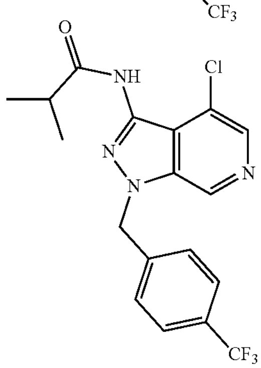 | N-(4-chloro-1-(4-(trifluoro-methyl)benzyl)-1H-pyrazolo[3,4-c]pyridin-3-yl)isobutyramide |

In one embodiment the present technology provides a metastasis inhibitor that is a fascin inhibitor that has a fascin inhibition $IC_{50}$ of no more than 100 μM. In some embodiments, the fascin inhibitor has a fascin inhibition $IC_{50}$ of no more than 50 μM. In some embodiments, the fascin inhibitor has a fascin inhibition $IC_{50}$ of no more than 20 μM. In some embodiments, the fascin inhibitor has a fascin inhibition $IC_{50}$ of no more than 8 μM.

Also provided is a method for evaluating a therapeutically effective dosage for treating a cancer (e.g., inhibiting metastasis) with a compound described herein, or pharmaceutically acceptable salt thereof, that includes determining the $IC_{50}$ of the agent in vitro. Such a method permits calculation of the approximate amount of agent needed per volume to inhibit cancer cell migration. Such amounts can be determined, for example, by standard microdilution methods. In some embodiments, the compound or composition as described herein can be administered in multiple doses over an extended period of time, or intermittently.

Second Agent

The metastasis inhibitors of the present disclosure may be part of a co-therapy with a second agent suitable for treating cancer. For example, in some embodiments, the second agent is a chemotherapeutic agent or an immunotherapeutic agent.

In some embodiments, the second agent is a chemotherapeutic agent. The chemotherapeutic agent may be, e.g., a known chemotherapeutic agent such as an FDA-approved chemotherapeutic agent. Examples of suitable chemotherapeutic agents include taxanes, such as docetaxel, paclitaxel, albumin-bound paclitaxel, etc.; cyclophosphamide, or anthracyclines, such as, doxorubicin, daunorubicin, pirarubicin, aclarubicin, and mitoxantrone.

In some embodiments, the second agent is an immunotherapeutic agent. The immunotherapeutic agent may be, e.g., a known immunotherapeutic agent such as an FDA-approved immunotherapeutic agent. Examples of suitable immunotherapeutic agents include immune checkpoint inhibitors such as anti-PD-1 antibody or anti-CTLA-4 antibody.

Patient Populations

The patients treated by the methods described herein may suffer from one or more cancer. The cancer may be selected from lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer.

In some embodiments, the cancer may be selected from one demonstrating a high fascin level. For example, this may be a subpopulation of a particular cancer having a high fascin level, e.g., as described in the following table, each reference of which is incorporated by reference in its entirety.

| Cancer Organ | Subtype | % with High Fascin Level | Publication |
| --- | --- | --- | --- |
| Pancreas | Low-grade PanIN-1a and -1b (pancreatic intraepithelial neoplasia) | 11% | Maitra, A. et al. (2002) Am. J. Clin. Pathol, 118: 52-59. |
| | High-grade PanIN-2 and -3 | 40% | |
| | PDAC (pancreatic ductal adenocarcinoma) | 95% | |
| Prostate | High-grade prostate intra-epithelial neoplasia (PIN) | 93% | Darnel, A. D. et al. (2009) Clin. Cancer Res. 15: 1376-1383. |
| | Localized prostate cancer | 70% | |
| | Metastatic prostate cancer | 45% | |

-continued

| Cancer Organ | Subtype | % with High Fascin Level | Publication |
| --- | --- | --- | --- |
| Lung | Non-small cell lung cancer (NSCLC) stages I | 44% | Ling, X. L. et al. (2015) OncoTarget and Therapy, 8: 1589-1595. |
| | Non-small cell lung cancer (NSCLC) stages II + III | 63% | |
| | Squamous cell carcinoma | 98% | Pelosi, G. et al. (2003) Br. J. Cancer. 88: 537-547. |
| | Adenocarcinoma | 78% | |
| | Large cell carcinoma | 83% | |
| Breast | Triple-negative | 88% | Wang, C. Q. et al., (2016) Cancer Med. 5: 1983-1988. |
| | HER-2 enriched | 38% | |
| | Luminal B | 17% | |
| | Luminal A | 12% | |
| Colon | Colonic adenocarcinoma Stages III and IV | 71% | Puppa, G. et al. (2007) Br. J. Cancer. 96: 1118-1126. |
| Esophagus | Esophageal squamous cell carcinoma (ESCC) | 68% | Takikita, M. et al. (2011) Anticancer Res. 31: 945-952. |
| Liver | Poorly differentiated primary hepatocellular carcinoma | 63% | Hayashi, Y. et al. (2011) Cancer Sci. 102: 1228-1235. |
| | Moderately differentiated HCCs | 16% | |
| Ovary | Stage III/IV ovarian cancer | 53% | Park, S. H. et al. (2014) Int. J. Oncol. 44: 637-646. |
| | Stage I/II ovarian cancer | 22% | |
| Lymphoma | Hodgkin lymphoma | 100% | Bakshi, N. A. et al. (2007) Arch. Pathol. Lab Med. 131(5): 742-747. |
| | Anaplastic larger cell lymphoma | 50% | |
| | Diffuse large B-cell lymphoma | 10-30% | |

In some embodiments, the cancer can be that which is described in: Strong association of fascin expression with triple negative breast cancer and basal-like phenotype in African-American women. Journal of Clinical Pathology. 2014; Prognostic Significance of Basal-Like Phenotype and Fascin Expression in Node-Negative Invasive Breast Carcinomas Clinical Cancer Research, 2006; Fascin expression predicts an aggressive clinical course in patients with advanced breast cancer Oncol Lett. 2015 July; 10(1):121-130. Epub 2015 May 8; Fascin Is a Key Regulator of Breast Cancer Invasion That Acts via the Modification of Metastasis-Associated Molecules *PLoS One.* 2011; 6(11): e27339; Fascin is involved in the chemotherapeutic resistance of breast cancer cells predominantly via the PI3K/Akt pathway British Journal of Cancer (2014) 111, 1552-1561; Fascin is Expressed in Basal-Liketype Triple Negative Breast Cancer Associated with High Malignant Potential in Japanese Women *Int J Cancer* Clin Res 2015, 2:5; Fascin expression in colorectal carcinomas Clinics vol. 65 no. 2 Sao Paulo 2010; Fascin-1 as a biomarker and prospective therapeutic target in colorectal cancer. Expert Rev Mol Diagn. 2015 January; 15(1):41-8; Overexpression of fascin-1 in advanced colorectal adenocarcinoma: Tissue microarray analysis of immunostaining scores with clinicopathological parameters, Disease Markers 23 (2007) 153-160; Prognostic Impact of Fascin-1 Expression is More Significant in Advanced Colorectal Cancer Journal of Surgical Research Volume 172, Issue 1, January 2012, Pages 102-108; Fascin overexpression promotes neoplastic progression in oral squamous cell carcinoma BMC Cancer 2012 12:32; Fascin upregulation in primary head and neck squamous cell carcinoma is associated with lymphatic metastasis Oncology Letters June 2014 Volume 7 Issue 6; OP050: Expression of fascin in squamous cell carcinoma of the oral cavity: Clinicopathological, prognostic significance and cell line study Oral Oncology Volume 49, Supplement 1, 1 May 2013, Pages S24-S25; Fascin Expression in Oral Squamous Cell Carcinoma using an Immunohistochemical Technique Journal of Dentomaxillofacial Radiology, Pathology and Surgery, Vol 4, No 2, Summer 2015; Independent prognostic value of fascin immunoreactivity in stage I nonsmall cell lung cancer.
Br J Cancer. 2003 Feb. 24; 88(4):537-47; Serological investigation of the clinical significance of fascin in non-small-cell lung cancer, Lung Cancer. 2013 November; 82(2):346-52. doi: 10.1016/j.lungcan.2013.08.017; Expression and diagnosis value of Fascin in non-small cell lung cancer patients Zhonghua Yi Xue Za Zhi. 2013 Aug. 20; 93(31): 2505-7; Expression of Fascin-1 on human lung cancer and paracarcinoma tissue and its relation to clinicopathological characteristics in patients with lung cancer, OncoTargets and Therapy 15 Sep. 2015 Volume 2015: 8: 2571-2576; EMMPRIN and fascin expression in non-small cell lung carcinoma
Central European Journal of Medicine, December 2010, Volume 5, Issue 6, pp 659-665; Significance of Immunohistochemical Expression of Fascin and Caveolin-1 in Non Small Cell Lung Cancer INTERNATIONAL JOURNAL OF CANCER RESEARCH 10(1):14-26 December 2013; Fascin 1 promoted the growth and migration of non-small cell lung cancer cells by activating YAP/TEAD signaling, TUMOR BIOLOGY; August 2016; Expression of Actin-bundling Protein Fascin and its Relationship with Altered E-cadherin and B-catenin Expressions in Ovarian Serous Neoplasms, The Korean Journal of Pathology 2005; 39: 258-64; Increased expression of fascin, motility associated protein, in cell cultures derived from ovarian cancer and in borderline and carcinomatous ovarian tumors, Clinical & Experimental Metastasis January 2000, Volume 18, Issue 1, pp 83-88; Prognostic significance of fascin expression in advanced poorly differentiated serous ovarian cancer, Anticancer Res. 2008 May-June; 28(3B):1905-10; Fascin is regulated by slug, promotes progression of pancreatic cancer in mice, and is associated with patient outcomes, Gastroenterology. 2014 May; 146(5):1386-96.e1-17; Fascin Regulates Prostate Cancer Cell Invasion and Is Associated with Metastasis and Biochemical Failure in Prostate Cancer Clin Cancer Res. 2009 Feb. 15; 15(4):1376-83. doi: 10.1158/1078-0432.CCR-08-1789; Fascin-1 expression correlates with repression of E-cadherin expression in hepatocellular carcinoma (HCC) cells and augments their invasiveness in combination with matrix metalloproteinases, Cancer Science. 14 Mar. 2011; Fascin expression is related to poor survival in gastric cancer, Pathology International. Volume 62, Issue 12. December 2012, Pages 777-784; Increasing expression of fascin in renal cell carcinoma associated with clinicopathological parameters of aggressiveness, Histology and Histopathology [1 Dec. 2006, 21(12):1287-1293; Phosphorylation of Fascin Decreases the Risk of Poor Survival in Patients With Esophageal Squamous Cell Carcinoma, J Histochem Cytochem. 2010 November; 58(11): 979-988; Effects of small interfering RNAs targeting fascin on human esophageal squamous cell carcinoma cell lines, Diagnostic Pathology 2010 5:41; Fascin and CK4 as Biomarkers for Esophageal Squamous Cell Carcinoma, Anticancer Res. Author manuscript; available in PMC 2011 Dec. 12; The Role of Fascin in the Migration and Invasiveness of Malignant Glioma Cells, Neoplasia, Volume 10, Issue 2—February 2008, Pages 149-159; Fascin-1 knock-down of human glioma cells reduces their microvilli/filopodia while improving their susceptibility to lymphocyte-mediated cytotoxicity, Am J Transl Res. 2015; 7(2): 271-284; Fascin-1 expression in papillary and invasive urothelial carcinomas of the urinary bladder, Human Pathology, Volume 36, Issue 7—July 2005, Pages 741-746; The Role of Fascin in Migration and Invasion of Urothelial Carcinoma of the Bladder, Urologia Internationalis, 2013; 91:227-235; Fascin Regulates Nuclear Movement and Deformation in Migrating Cells Developmental Cell. Volume 38, Issue 4, p 371-383, 22 Aug. 2016, each of which is incorporated by reference in its entirety.

In some embodiments, the cancer is a cancer of which chemotherapy or immunotherapy has been shown to be effective. Some embodiments include where the patient is suffering from a sub-group of one of the above cancers, for example, neuroendocrine prostate cancer, activated B-cell subtype of diffuse large B-cell lymphoma, triple-negative breast cancer.

In some embodiments, the patient is undergoing or about to undergo chemotherapy. In other embodiments, the patient has already undergone chemotherapy, e.g., in the past 2 weeks, 1, 2, 3, 4 5, 6, 7, 8, 9, 10, 11, 12, 15, 18 or 24 months. In some embodiments, the patient is undergoing or about to undergo immunotherapy. In other embodiments, the patient has already undergone immunotherapy, e.g., in the past 2 weeks, 1, 2, 3, 4 5, 6, 7, 8, 9, 10, 11, 12, 15, 18 or 24 months.

Methods

The present disclosure includes methods of treating cancer in a patient in need thereof, comprising administering to the patient a chemotherapeutic agent or an immunotherapeutic agent and a metastasis inhibiting compound, as described in this disclosure.

In some embodiments, the second agent is a chemotherapeutic agent. The chemotherapeutic agent may be, e.g., a known chemotherapeutic agent such as an FDA-approved chemotherapeutic agent. Examples of suitable chemotherapeutic agents include taxanes, such as docetaxel, paclitaxel, albumin-bound paclitaxel, etc.; cyclophosphamide; anthracyclines, such as, doxorubicin, daunorubicin, pirarubicin, aclarubicin, and mitoxantrone; platinum-based drugs, such as, carboplatin or cisplatin. The chemotherapeutic agent may be a combination of agents, as is known in the field. For example, clinical oncologists combine a platinum-based drug such as carboplatin or cisplatin with a taxane such as paclitaxel or docetaxel. Additional chemotherapeutic agents include carboplatin, cisplatin, oxaliplatin, paclitaxel, docetaxel, cabazitaxel, anastrozole, capecitabine, cyclophosphamide, doxorubicin, exemestane, 5-fluorouracil, gemcitabine, ixabepilone, letrozole, estramustine, mitoxantrone, etoposide, vinorelbine, or pemetrexed.

In some embodiments, the second agent is an immunotherapeutic agent. The immunotherapeutic agent may be, e.g., a known immunotherapeutic agent such as an FDA-approved immunotherapeutic agent. Examples of suitable immunotherapeutic agents include immune checkpoint inhibitors such anti-PD-1 antibodies, anti-PD-L1 antibodies, or anti-CTLA-4 antibodies.

In some embodiments, the compound represented by formula (I):

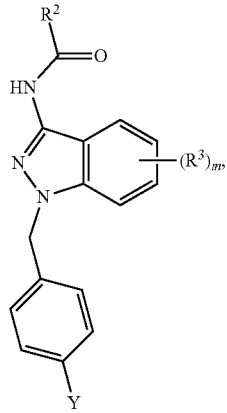

(IV)

or tautomer thereof, and/or a pharmaceutically acceptable salt thereof; wherein $R^2$ is 6- to 10-membered aryl or 5- to 10-membered heteroaryl; wherein the 6- to 10-membered aryl or 5- to 10-membered heteroaryl is optionally substituted with 1 to 4 $R^4$, wherein each $R^4$ is independently selected from the group consisting of lower alkyl, lower haloalkyl, —OH, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, SO$_2$NR$^{10}$R$^{10}$, phenyl (optionally substituted with lower alkyl, halo or lower haloalkyl, or —OH), and —NR$^{10}$SO$_2$R$^7$;

each $R^3$ is independently selected from the group consisting of lower alkyl, lower haloalkyl, —OH, —SH, —SR$^7$, —NR$^{10}$R$^{10}$, halo, cyano, nitro, —COH, —COR$^7$, —CO$_2$H, —CO$_2$R$^7$, —CONR$^{10}$R$^{10}$, —OCOR$^7$, —OCO$_2$R$^7$, —OCONR$^{10}$R$^{10}$, —NR$^{10}$COR$^{10}$, —NR$^{10}$CO$_2$R$^{10}$, —SOR$^7$, —SO$_2$R$^7$, SO$_2$NR$^{10}$R$^{10}$, and —NR$^{10}$SO$_2$R$^7$;

m is 0, 1, 2, or 3;
$R^7$ is lower alkyl; and
each $R^{10}$ is independently hydrogen or lower alkyl, or two $R^{10}$ together with the atom(s) attached thereto form a 4- to 6-membered ring;
Y is selected from the group consisting of CF$_3$, Cl, F, and Me.

In some embodiments, in the compound of Formula I, $R^2$ is optionally substituted with 1 to 4 $R^4$, and $R^2$ is selected from the group consisting of furan, benzofuran, pyridine, pyridazine, pyrimidine, pyrazine, thiophene, thiazole, isothiazole, oxazole, isoxazole, oxadiazole, imidazole, pyrrole, and pyrazole. In some embodiments, in the compound of Formula I, $R^2$ is selected from the group consisting of

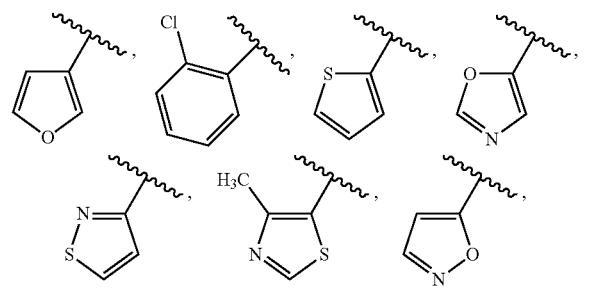

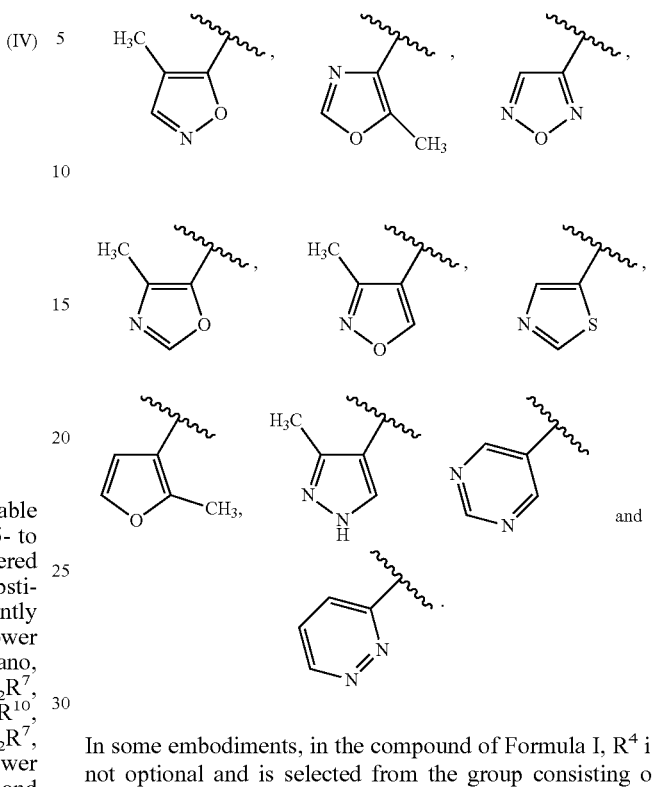

In some embodiments, in the compound of Formula I, $R^4$ is not optional and is selected from the group consisting of lower alkyl, halo, lower haloalkyl, —OH, —OR$^7$, cyano and phenyl optionally substituted methyl, and wherein $R^7$ is lower alkyl or lower haloalkyl. In some embodiments, in the compound of Formula I, m is 0. In some embodiments, the compound of Formula I is selected from:

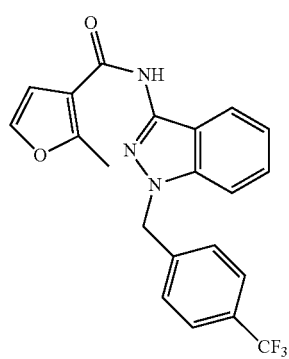

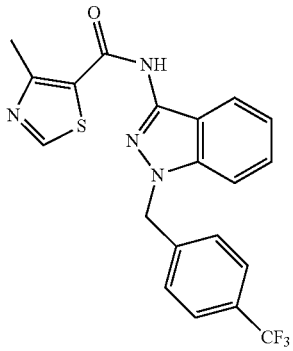

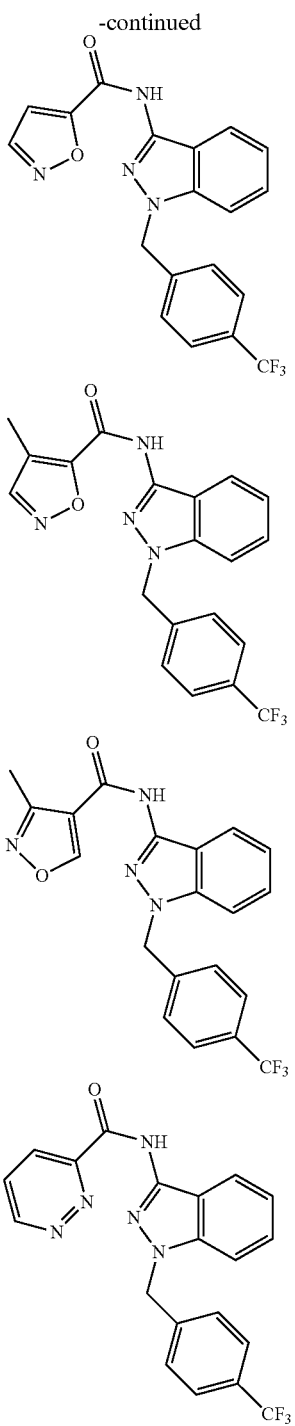

or tautomer thereof, and/or a pharmaceutically acceptable salt thereof.

In some embodiments, the cancer may be selected from lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer.

In some embodiments, the cancer is a cancer of which chemotherapy or immunotherapy has been shown to be effective. Some embodiments include where the patient is suffering from a sub-group of one of the above cancers, for example, neuroendocrine prostate cancer, activated B-cell subtype of diffuse large B-cell lymphoma, triple-negative breast cancer.

In some embodiments, the patient is undergoing or about to undergo chemotherapy. In other embodiments, the patient has already undergone chemotherapy, e.g., in the past 2 weeks, 1, 2, 3, 4 5, 6, 7, 8, 9, 10, 11, 12, 15, 18 or 24 months.

In some embodiments, the patient is undergoing or about to undergo immunotherapy. In other embodiments, the patient has already undergone immunotherapy, e.g., in the past 2 weeks, 1, 2, 3, 4 5, 6, 7, 8, 9, 10, 11, 12, 15, 18 or 24 months.

Other embodiments include a method of increasing a response to a chemotherapeutic agent or an immunotherapeutic agent in a patient in need thereof, comprising: administering to the patient a metastasis-inhibiting compound, as described in this disclosure.

In some embodiments, the second agent is a chemotherapeutic agent. The chemotherapeutic agent may be, e.g., a known chemotherapeutic agent such as an FDA-approved chemotherapeutic agent. Examples of suitable chemotherapeutic agents include taxanes, such as docetaxel, paclitaxel, albumin-bound paclitaxel, etc.; cyclophosphamide, or anthracyclines, such as, doxorubicin, daunorubicin, pirarubicin, aclarubicin, and mitoxantrone.

In some embodiments, the second agent is an immunotherapeutic agent. The immunotherapeutic agent may be, e.g., a known immunotherapeutic agent such as an FDA-approved immunotherapeutic agent. Examples of suitable immunotherapeutic agents include immune checkpoint inhibitors such as anti-PD-1 antibody or anti-CTLA-4 antibody.

In some embodiments, the compound represented by formula (I):

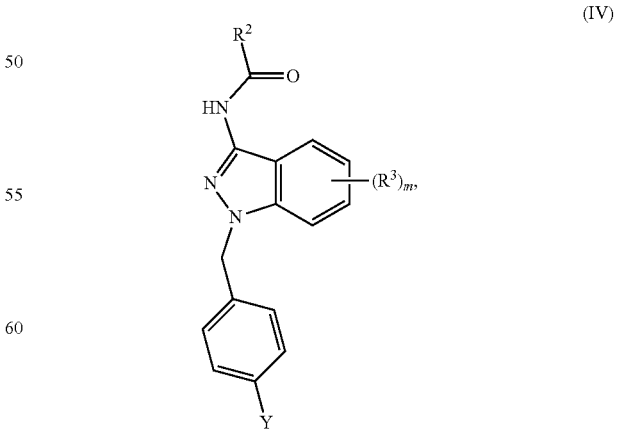

(IV)

or tautomer thereof, and/or a pharmaceutically acceptable salt thereof; wherein $R^2$ is 6- to 10-membered aryl or 5- to 10-membered heteroaryl; wherein the 6- to 10-membered aryl or 5- to 10-membered heteroaryl is optionally substituted with 1 to 4 wherein each $R^4$ is independently selected from the group consisting of lower alkyl, lower haloalkyl, —OH, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^{10}$, —$NR^{10}CO_2R^{10}$, —$SOR^7$, —$SO_2R^7$, $SO_2NR^{10}R^{10}$, phenyl (optionally substituted with lower alkyl, halo or lower haloalkyl, or —OH), and —$NR^{10}SO_2R^7$;

each $R^3$ is independently selected from the group consisting of lower alkyl, lower haloalkyl, —OH, —SH, —$SR^7$, —$NR^{10}R^{10}$, halo, cyano, nitro, —COH, —$COR^7$, —$CO_2H$, —$CO_2R^7$, —$CONR^{10}R^{10}$, —$OCOR^7$, —$OCO_2R^7$, —$OCONR^{10}R^{10}$, —$NR^{10}COR^{10}$, —$NR^{10}CO_2R^{10}$, —$SOR^7$, —$SO_2R^7$, $SO_2NR^{10}R^{10}$, and —$NR^{10}SO_2R^7$, m is 0, 1, 2, or 3;

$R^7$ is lower alkyl; and each $R^{10}$ is independently hydrogen or lower alkyl, or two $R^{10}$ together with the atom(s) attached thereto form a 4- to 6-membered ring;

Y is selected from the group consisting of $CF_3$, Cl, F, and Me.

In some embodiments, in the compound of Formula I, $R^2$ is optionally substituted with 1 to 4 $R^4$, and $R^2$ is selected from the group consisting of furan, benzofuran, pyridine, pyridazine, pyrimidine, pyrazine, thiophene, thiazole, isothiazole, oxazole, isoxazole, oxadiazole, imidazole, pyrrole, and pyrazole. In some embodiments, in the compound of Formula I, $R^2$ is selected from the group consisting of

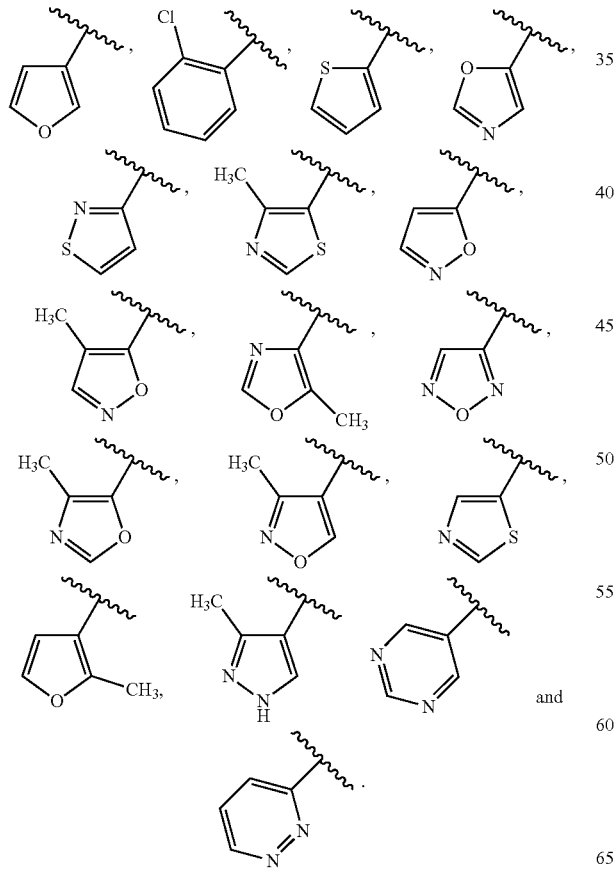

In some embodiments, in the compound of Formula I, $R^4$ is not optional and is selected from the group consisting of lower alkyl, halo, lower haloalkyl, —OH, —$OR^7$, cyano and phenyl optionally substituted methyl, and wherein $R^7$ is lower alkyl or lower haloalkyl. In some embodiments, in the compound of Formula I, m is 0. In some embodiments, the compound of Formula I is selected from:

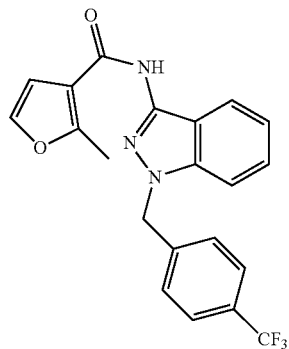

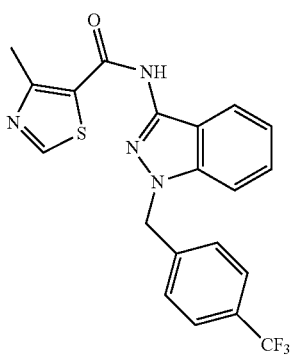

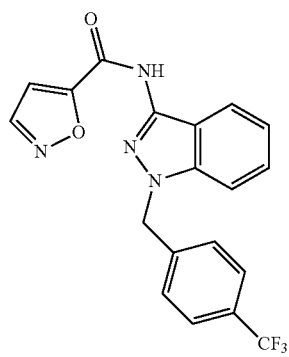

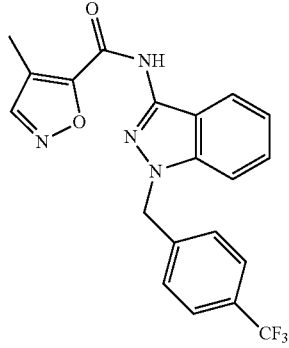

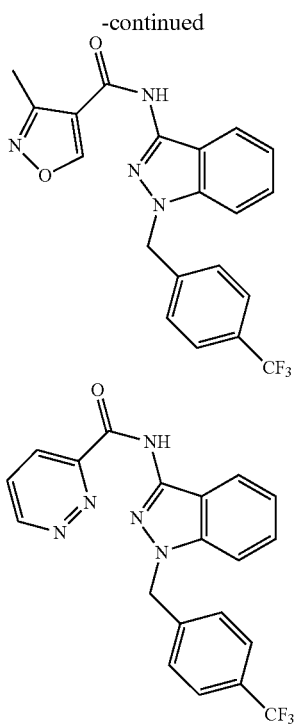

or tautomer thereof, and/or a pharmaceutically acceptable salt thereof.

In some embodiments, increasing a response to a chemotherapeutic agent or an immunotherapeutic agent means increasing the survival prognosis, e.g., the mean survival of a patient population and/or increasing the reduction in tumor growth or presence in a patient or patient population compared to therapy with the chemotherapeutic agent or immunotherapeutic agent and not the metastasis inhibiting compound. In some embodiments, the increase in a response to a chemotherapeutic agent or an immunotherapeutic agent is synergistic, meaning that the effect is greater than administering the chemotherapeutic agent or immunotherapeutic agent alone and greater than administering the metastasis-inhibiting compound alone. Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters.

The amount of metastasis inhibiting compound of the present disclosure may be determined by a medical professional. The daily dosage of the products may be varied over a wide range from 10 to 2,000 mg per adult human per day, or any range therein. For oral administration, the compositions are preferably provided in the form of tablets, capsules or other orally admisterable form containing, 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any range therein. Preferably, the range is from about 0.01 to about 50.0 mg/kg of body weight per day, or any range therein. More preferably, from about 0.01 to about 10.0 mg/kg of body weight per day, or any range therein. More preferably, from about 0.01 to about 1.0 mg/kg of body weight per day, or any range therein. The metastasis-inhibiting compound may be administered on a regimen of 1 to 4 times per day. For example, the metastasis-inhibiting compound of the present disclosure may be administered at one or more doses of from about 0.1 mg/kg to about 100 mg/kg. For example, the disclosed metastasis inhibiting compound may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 55, 60, 65, 70, 75, 80, 85, 90, 95 or about 100 mg/kg. Values and ranges intermediate to the recited values are also intended to be part of this disclosure. These values may apply to intravenous infusion and/or subcutaneous delivery. Other forms of delivery described herein may also be administered at these doses. The dosages may be varied depending upon the requirement of the patients, the severity of the condition being treated and the metastasis-inhibiting compound being employed. The use of either daily administration or post-periodic dosing may be employed.

The metastasis inhibiting compound may be administered concurrently with a chemotherapeutic agent or an immunotherapeutic agent, or may be administered within one year, or up to 18 months of administration of a chemotherapeutic agent or an immunotherapeutic agent, e.g., within 1, 2, 3, 4, 5, 6, or 7 days or within 1, 2, 3, 4 weeks or within 1, 2, 3, 45, 6, 7, 8, 9, 10, 11, 12, 13, 14, 15, 16, 17, 18, 19, 20, 21, 22, 23, 24 months.

Compositions

The compounds (e.g., metastasis inhibiting compounds) as described herein can be formulated as pharmaceutical compositions and administered to a mammalian host, such as a human patient in a variety of forms adapted to the chosen route of administration, i.e., orally or parenterally, by intravenous, intramuscular, topical, transdermally, intrathecally, ocularly, intranasally, intraperitoneally or subcutaneous routes.

The compounds (e.g., metastasis inhibiting compound) described herein may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. A material used in preparing any unit dosage form should be pharmaceutically acceptable and substantially non-toxic in the amounts employed. In addition, the active compound may be incorporated into sustained-release preparations and devices.

The active compounds described herein may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds described herein, or pharmaceutically acceptable salts thereof, to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds described herein, or pharmaceutically acceptable salts thereof, can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds described herein, or pharmaceutically acceptable salts thereof, in a liquid composition, such as a lotion, will be about 0.01 wt %, about 0.1 wt %, about 1.0 wt %, about 2.0 wt %, about 3.0 wt %, about 4.0 wt %, about 5.0 wt %, about 10.0 wt %, about 25.0 wt %, or a range between and including any two of these values. The concentration in a semi-solid or solid composition such as a gel or a powder will be about 0.01 wt %, about 0.1 wt %, about 1.0 wt %, about 2.0 wt %, about 3.0 wt %, about 4.0 wt %, about 5.0 wt %, about 10.0 wt %, about 25.0 wt %, or a range between and including any two of these values.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 1.0 to about 200 mg/kg, e.g., from about 1 to about 100 mg/kg of body weight per day, such as about 2.0 to about 100 mg/kg of body weight per day, such as about 3.0 to about 50 mg per kilogram body weight of the recipient per day, or in the range of about 5 to 20 mg/kg/day. Alternatively, the compositions can be administered five times a week on five consecutive days with a two day rest, or four times a week on four consecutive days with a three day rest, or every other day.

Methods for extrapolating effective dosages in mice and other animals, to humans are known in the art (See, for example, U.S. Pat. No. 4,938,949). For example, in some embodiments, compounds described herein, or pharmaceutically acceptable salts thereof, (for example those useful for the treatment of colon and/or ovarian cancer) may be administered at dosage levels of about 0.01 mg/kg to about 300 mg/kg, from about 0.1 mg/kg to about 250 mg/kg, from about 1 mg/kg to about 200 mg/kg, from about 1 mg/kg to about 150 mg/kg, from about 1 mg/kg to about 100 mg/kg, from about 1 mg/kg to about 90 mg/kg, from about 1 mg/kg to about 80 mg/kg, from about 1 mg/kg to about 70 mg/kg, from about 1 mg/kg to about 60 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 5 mg/kg to about 100 mg/kg, from about 5 mg/kg to about 90 mg/kg, from about 5 mg/kg to about 80 mg/kg, from about 5 mg/kg to about 70 mg/kg, from about 5 mg/kg to about 60 mg/kg, from about 5 mg/kg to about 50 mg/kg, from about 5 mg/kg to about 40 mg/kg, from about 5 mg/kg to about 30 mg/kg, from about 5 mg/kg to about 20 mg/kg, from about 10 mg/kg to about 100 mg/kg, from about 10 mg/kg to about 90 mg/kg, from about 10 mg/kg to about 80 mg/kg, from about 10 mg/kg to about 70 mg/kg, from about 10 mg/kg to about 60 mg/kg, from about 10 mg/kg to about 50 mg/kg, from about 10 mg/kg to about 40 mg/kg, from about 10 mg/kg to about 30 mg/kg, from about 10 mg/kg to about 20 mg/kg, from about 20 mg/kg to about 100 mg/kg, from about 20 mg/kg to about 90 mg/kg, from about 20 mg/kg to about 80 mg/kg, from about 20 mg/kg to about 70 mg/kg, from about 20 mg/kg to about 60 mg/kg, from about 20 mg/kg to about 50 mg/kg, from about 20 mg/kg to about 40 mg/kg, from about 20 mg/kg to about 30 mg/kg, of subject body weight per day, one or more times a day, to obtain the desired therapeutic effect. In some embodiments, compounds may be administered at a dosage of about 1 mg/kg or greater, 5 mg/kg or greater; 10 mg/kg or greater, 15 mg/kg or greater, 20 mg/kg or greater, 25 mg/kg or greater, 30 mg/kg or greater, 35 mg/kg or greater, 40 mg/kg or greater, 45 mg/kg or greater, 50 mg/kg or greater, 60 mg/kg or greater, 70 mg/kg or greater, of body weight. It will also be appreciated that dosages smaller than 0.01 mg/kg or greater than 70 mg/kg (for example 70-200 mg/kg) can be administered to a subject.

In some embodiments, the compounds described herein may be used in chemotherapy (i.e., to inhibit metastasis) and may be administered at higher dosage. For example, compounds to be used in chemotherapy may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In certain other embodiments, the compounds described herein may be used in supportive therapy (e.g., as an adjuvant to surgery or irradiation in a range of common types of tumor) and may be administered at lower dosage. For example, compounds to be used in supportive therapy may be administered from about 1 mg/kg to about 30 mg/kg, from about 1 mg/kg to about 25 mg/kg, from about 5 mg/kg to about 20 mg/kg, of subject body weight per day, one or more times a day, to obtain the desired therapeutic effect.

In certain other embodiments, the compounds described herein may be used for treating metastatic cancer (e.g., ovarian and/or colon cancer) and may be administered at an intermediate dosage. For example, compounds to be used in supportive therapy may be administered from about 1 mg/kg to about 100 mg/kg, from about 1 mg/kg to about 80 mg/kg, from about 5 mg/kg to about 70 mg/kg, from about 10 mg/kg to about 70 mg/kg, from about 10 mg/kg to about 60 mg/kg, from about 20 mg/kg to about 70 mg/kg, from about 20 mg/kg to about 60 mg/kg, of subject body weight per day, one or more times a day, to obtain the desired therapeutic effect.

The compound is conveniently administered in unit dosage form; for example, containing 45 to 3000 mg, conveniently 90 to 2250 mg, most conveniently, 450 to 1500 mg of active ingredient per unit dosage form. In some embodiments, the compound is administered at dosages of about 1 to about 100 mg/kg.

Ideally, the active ingredient should be administered to achieve peak plasma concentrations of the active compound of from about 0.5 nM to about 10 µM, or about 1 nM to 1 µM, or about 10 nM to about 0.5 µM. This may be achieved, for example, by the intravenous injection of a 0.05 to 5% solution of the active ingredient, optionally in saline, or orally administered as a bolus containing about 20-2000 mg of the active ingredient. Desirable blood levels may be maintained by continuous infusion to provide about 0.2 to 1.0 mg/kg/hr or by intermittent infusions containing about 0.4 to 20 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds described herein, or pharmaceutically acceptable salts thereof, are useful as therapeutic agents administered for inhibition of cell migration and treatment of metastatic cancer. Such cancers include but are not limited to, e.g., cancers involving the animal's head, neck, lung, mesothelioma, mediastinum, esophagus, stomach, pancreas, hepatobiliary system, small intestine, colon, colorectal, rectum, anus, kidney, ureter, bladder, prostate, urethra, penis, testis, gynecological organs, ovaries, breast, endocrine system, skin, or central nervous system. Thus, for example, the cancer can be a breast cancer, a leukemia, a lung cancer, a colon cancer, a central nervous system cancer, a melanoma, an ovarian cancer, a renal cancer, or a prostate cancer.

Additionally, compounds described herein, or pharmaceutically acceptable salts thereof, such as the exemplary salts described herein, may be useful as pharmacological tools for the further investigation of the inhibition of cell migration.

The compounds described herein, or pharmaceutically acceptable salts thereof, can also be administered in combination with other therapeutic agents that are effective for treating or controlling the spread of cancerous cells or tumor cells.

Moreover, the compounds described herein, or pharmaceutically acceptable salts thereof, can be tested in appropriate animal models. For example, the compounds described herein, or pharmaceutically acceptable salts thereof, can be tested in animals with known tumors, or animals that have been injected with tumor cells into a localized area. The degree or number of secondary tumors that form over time is a measure of metastasis and the ability of the compounds to inhibit such metastasis can be evaluated relative to control animals that have the primary tumor but receive no test compounds.

The compounds described herein, or pharmaceutically acceptable salts thereof, will also find use in treatment of brain disorders (Kraft et al., J. Neurosci. 2006 Aug. 23; 26(34):8734-47); Hodgkin's disease (Pinkus et al., Am J Pathol. 1997 February; 150(2):543-62); virus infection (Mosialos et al., Am J Pathol. 1996 February; 148(2):593-600); neuronal degeneration (Fulga et al., Nat Cell Biol. 2007 February: 9(2):139-48); lymphoid hyperplasia (Said et al., Mod Pathol. 1997 May; 10(5):421-7); and ischemia (Meller et al., J Neurosci. 2008 Jan. 2; 28(1):50-9.)

General Synthetic Methods

The metastasis inhibiting compounds described herein are commercially available or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the metastasis inhibiting compounds described herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), *March's Advanced Organic Chemistry*, (John Wiley and Sons, 4th Edition), and Larock's *Comprehensive Organic Transformations* (VCH Publishers Inc., 1989).

The various starting materials, intermediates, and compounds described herein may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Amide coupling reagents are known in the art and may include, but are not limited to, amininum and phosphonium based reagents. Aminium salts include N-[(dimethylamino)-1H-1,2,3-triazolo[4,5-b]pyridine-1-ylmethylene]-N-methyl-methanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP). Amide formation step may be conducted in a polar solvent such as dimethylformamide (DMF) and may also include an organic base such as diisopropylethylamine (DIEA) or dimethylaminopyridine (DMAP).

Cross-coupling reactions are well known in the art and, for example, are reported in Anna Roglans, et al. Diazonium Salts as Substrates in Palladium-Catalyzed Cross-Coupling Reactions, Chem. Rev., 2006, 106 (11):4622-4643; Brad M. Rosen, et al., Nickel-Catalyzed Cross-Couplings Involving Carbon-Oxygen Bonds, Percec Chem. Rev., 2011, 111 (3): 1346-1416; Jean-Pierre Corbet, et al., Selected Patented Cross-Coupling Reaction Technologies, Chem. Rev., 2006, 106 (7):2651-2710; Gwilherm Evano et al., Copper-Mediated Coupling Reactions and Their Applications in Natural Products and Designed Biomolecules Synthesis, Chem. Rev., 2008, 108 (8):3054-3131; Benny Bogoslaysky, et al., Formation of a Carbon-Carbon Triple Bond by Coupling Reactions In Aqueous Solution, *Science* 308 (5719): 234-235 (2005); and M. Lafrance, et al., Catalytic Intermolecular Direct Arylation of Perfluorobenzenes, J. Am. Chem. Soc. 128 (27): 8754-8756 (2006); Norio Miyaura, et al., "A new stereospecific cross-coupling by the palladium-catalyzed reaction of 1-alkenylboranes with 1-alkenyl or 1-alkynyl halides," Tetrahedron Letters, 1979, 20(36): 3437-3440; P. E. Fanta, "The Ullmann Synthesis of Biaryls", Synthesis, 1974, 1974: 9-21; M. Gomberg, and W. E. Bachmann, J. Am. Chem. Soc., 1924, 42(10):2339-2343; R. J. P. Corriu and Masse, J. P. "Activation of Grignard reagents by transition-metal complexes. A new and simple synthesis of trans-stilbenes and polyphenyls," Journal of the Chemical Society, Chemical Communications, 1972, (3):144a.

In some aspects, compounds of Formula I can be prepared according to Scheme 1 or other methods described herein.

Scheme 1

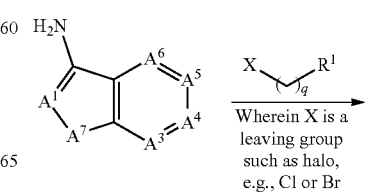

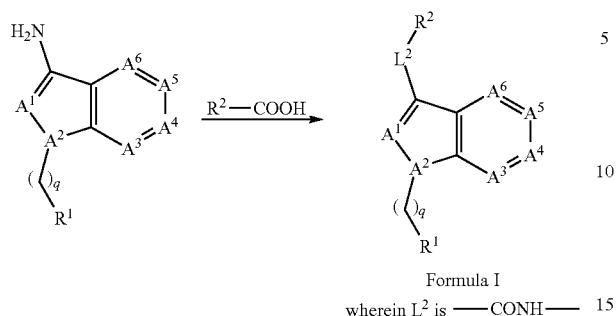

Formula I wherein L² is —CONH—

In some aspects, compounds of Formula IIIa wherein R³ is hydrogen (Compound 2-3) can be prepared from 1H-indazol-3-amine (Compound 2-1, available from e.g., Enamine LLC) according to Scheme 2 or other methods described herein.

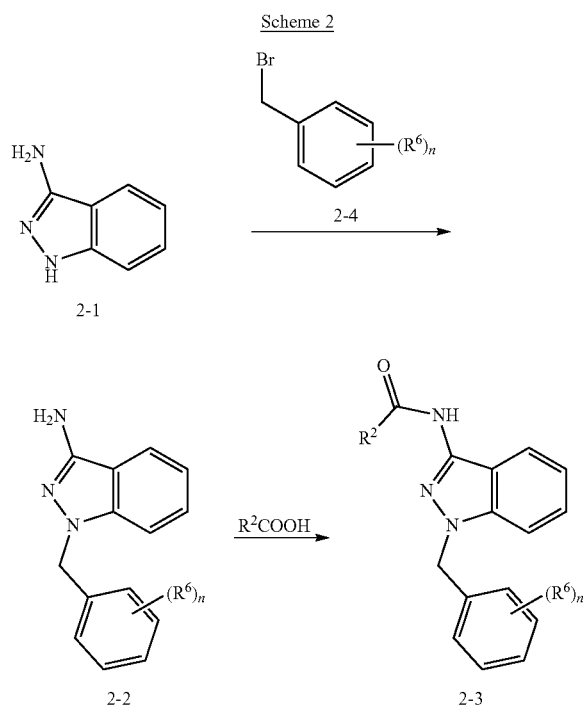

In some aspects, compounds of Formula VIIIa wherein R³ is 4-chloro (Compound 3-2 or 3-3) from 4-chloro-1H-pyrazolo[3,4-c]pyridin-3-amine (Compound 3-1, available from, e.g., Novasyn Organics PVT. Ltd.) can be prepared according to Scheme 3 or other methods described herein. Compounds of formula 2-4 are generally available from commercial sources or can prepared by methods known in the art. For example, 4-(bromomethyl)benzonitrile, 3-(bromomethyl)benzonitrile, 2-fluorobenzyl bromide, 3-fluorobenzyl bromide, 3-chlorobenzyl bromide, 4-chlorobenzyl bromide, 4-fluorobenzyl bromide, 4-methylbenzyl bromide, 3,4-difluorobenzyl bromide and 2,3-difluoro-4-methylbenzyl bromide, etc., are available from Sigma-Aldrich Co. LLC.

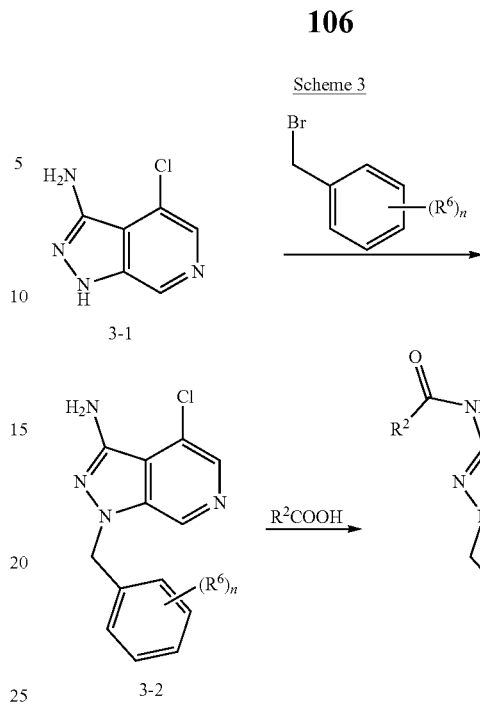

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following Examples, which is provided by way of illustration and is not intended to be limiting of the present technology. Other compounds were or may be prepared similarly or by methods known in the art.

EXAMPLES

Mouse Colony

Female BALB/c mice (female 6-8 week old) were purchased from commercial sources. NSG immunodeficient mice (female 6- to 10-week-old) were purchased from commercial sources.

Cell Culture

Mouse 4T1 mammary tumor cells and human MDA-MB-231 breast cancer cells were obtained from American Type Culture Collection. 4T1 cells and MDA-MB-231 cells were cultured in DMEM supplemented with 10% FBS as previously described. Chen, L., Yang, S., Jakoncic, J., Zhang, J. J. & Huang, X. Y. Migrastatin analogues target fascin to block tumour metastasis. *Nature* 464, 1062-1066 (2010); Huang, F. K. et al. Targeted inhibition of fascin function blocks tumour invasion and metastatic colonization. *Nat Commun* 6, 7465 (2015); Han, S. et al. Improving fascin inhibitors to block tumor cell migration and metastasis. *Mol Oncol* 10, 966-980 (2016).

Pharmacokinetic Study of Compound a in Mice

Concentrations of Compound A in plasma were determined using high performance liquid chromatography with tandem mass spectrometry (LC MS/MS). All blood samples were transferred into commercial tube containing Potassium (K2) EDTA and processed for plasma. Samples were centrifuged (3000×g for 10 minutes at 2 to 8° C.) within one hour of collection. The assays used a Sciex API 4000 detector and nifedipine as an internal standard. The calibration ranges for Compound A for were 5.00 to 5000 ng/mL. The plasma concentration of Compound A in mice was subjected to a non-compartmental pharmacokinetic analysis by using the Phoenix WinNonlin software (version 6.3, Pharsight, Mountain View, Calif.). The nominal dose levels and nominal sampling times were used in the calculation of all pharmacokinetic parameters. The linear/log trapezoidal rule was applied in obtaining the PK parameters. Compound A was observed to be stable after freeze-thaw, and during storage, processing and analysis.

4T1 Mammary Tumor Metastasis in Mice

Female BALB/c mice (6-8 week old) were purchased from Charles River. 4T1 tumor cells ($1\times10^5$) were injected subcutaneously into the abdominal mammary gland area of mice using 0.1 ml of a single-cell suspension in PBS on Day 0 as previously described. Chen, L., Yang, S., Jakoncic, J., Zhang, J. J. & Huang, X. Y. Migrastatin analogues target fascin to block tumor metastasis. *Nature* 464, 1062-1066 (2010); Huang, F. K. et al. Targeted inhibition of fascin function blocks tumor invasion and metastatic colonization. *Nat Commun* 6, 7465 (2015); Han, S. et al. Improving fascin inhibitors to block tumor cell migration and metastasis. *Mol Oncol* 10, 966-980 (2016). Starting on Day 8, when the tumors averaged about ~4-5 mm in diameter, Compound A or control solvent were given once or twice every day by oral gavage at 10, 30, 100 or 300 mg/kg per mouse until Day 27. On Day 28, the mice were sacrificed. This dosage regimen was well tolerated with no signs of overt toxicity. Numbers of metastatic 4T1 cells in lungs were determined by the clonogenic assay. In brief, lungs were removed from each mouse, finely minced and digested in 5 ml of enzyme cocktail containing 1×PBS and 1 mg/ml collagenase type IV for 2 hours at 37° C. on a platform rocker. After incubation, samples were filtered through 70-μm nylon cell strainers and washed twice with PBS. Resulting cells were suspended, plated with a series of dilutions in 10 cm tissue culture dishes in DMEM medium containing 60 μM thioguanine for clonogenic growth. As 4T1 tumor cells are resistant to 6-thioguanine, metastasized tumor cells formed foci after 14 days, at which time they were fixed with 4% paraformaldehyde and stained with crystal violet staining solution for counting.

For the experiments in FIG. 1h, 4T1 tumor cells ($1\times10^5$) suspended in PBS were injected subcutaneously into the abdominal mammary gland area of mice on day 1. Starting on day 4, 8, or 15, Compound A was given to mice once every day by oral gavage at 100 mg kg$^{-1}$ per mouse. Vehicle solvent was given to the control group of mice once every day by gavage. Starting on day 8, paclitaxel was given to mice twice a week by intraperitoneal injection at 20 mg kg' per mouse for two weeks. Primary tumors were removed on day 15. All mice were killed for clonogenic assay on day 35.

MDA-MB-231 Human Breast Tumor Metastasis in Mice

MDA-MB-231 cells (subclone LM2) ($1\times10^5$) suspended in PBS were injected subcutaneously into the abdominal mammary gland area of mice on day 1 as previously described. Chen, L., Yang, S., Jakoncic, J., Zhang, J. J. & Huang, X. Y. Migrastatin analogues target fascin to block tumor metastasis. *Nature* 464, 1062-1066 (2010); Huang, F. K. et al. Targeted inhibition of fascin function blocks tumor invasion and metastatic colonization. *Nat Commun* 6, 7465 (2015); Han, S. et al. Improving fascin inhibitors to block tumor cell migration and metastasis. *Mol Oncol* 10, 966-980 (2016). Starting on day 8, Compound A or control solvent were given once or twice a day for 6 days every week by gavage until the eighth week. On the first day of the ninth week, the mice were killed. This dosage regimen was well tolerated with no signs of overt toxicity. Numbers of metastatic MDA-MB-231 cells in lungs were determined by the clonogenic assay. In brief, lungs were removed from each mouse once sacrificed, finely minced and digested in 5 ml of enzyme cocktail containing 1×PBS and 1 mg/ml collagenase type IV for 2 h at 37° C. on a platform rocker. After incubation, samples were filtered through 70-μm nylon cell strainers and washed twice with PBS. Resulting cells were suspended, plated with a series of dilutions in 10 cm tissue culture dishes in medium containing 2.0 μg/ml puromycin for clonogenic growth. As these MBA-MB-231 tumor cells were stably transfected with the vector pSuper-puro, metastasized tumor cells formed foci after 14 days, at which time they were fixed with 4% paraformaldehyde and stained with crystal violet staining solution for counting.

For combination treatments with chemotherapy, MDA-MB-231 tumor cells ($1\times10^5$) suspended in PBS were injected subcutaneously into the abdominal mammary gland area of mice on day 1. Starting on day 1, 8, or 15, Compound A was given to mice once a day for 6 days every week by oral gavage at 300 mg/kg per mouse. Vehicle solvent was given to control mice once a day for 6 days every week. Starting on day 15, doxorubicin hydrochloride (Sigma) (2 mg/kg) and cyclophosphamide monohydrate (Sigma) (60 mg/kg) were given to mice once a week for four weeks. Primary tumors were removed on day 29. Death of mice was used as the endpoint.

Combination Treatment with Compound a and Immunotherapy

Female BALB/c mice (6- to 8-week-old) were purchased from Charles River Laboratories. 4T1 breast tumor cells ($1\times10^5$) suspended in PBS were injected subcutaneously into the abdominal mammary gland area of mice on day 0 as previously described. Chen, L., Yang, S., Jakoncic, J., Zhang, J. J. & Huang, X. Y. Migrastatin analogues target fascin to block tumor metastasis. *Nature* 464, 1062-1066 (2010); Huang, F. K. et al. Targeted inhibition of fascin function blocks tumor invasion and metastatic colonization. *Nat Commun* 6, 7465 (2015); Han, S. et al. Improving fascin inhibitors to block tumor cell migration and metastasis. *Mol Oncol* 10, 966-980 (2016). Starting on day 8 or 22, Compound A was given to mice once every day for 5 days a week by oral gavage at 100 mg/kg per mouse. Tumor-bearing mice were given 10 mg/kg anti-PD-1 and 10 mg/kg anti-CTLA-4 antibodies i.p. on day 11, 13, 15, and 17 as previously described. Kim, K. et al. Eradication of metastatic mouse cancers resistant to immune checkpoint blockade by suppression of myeloid-derived cells. *Proc Natl Acad Sci USA* 111, 11774-11779 (2014). Control group mice were given control mouse IgG at the same time. Primary tumor volume was calculated as length×width$^2$×π/6.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed:

1. A method of increasing a response to a chemotherapeutic agent or an immunotherapeutic agent in a patient in need thereof, comprising:

administering to the patient a compound A represented by formula:

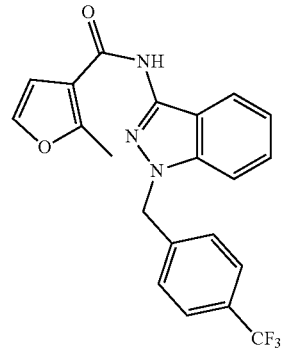

or tautomer thereof, and/or a pharmaceutically acceptable salt thereof, wherein the patient is undergoing or about to undergo chemotherapy; and wherein the chemotherapeutic agent is paclitaxel, cyclophosphamide, or doxorubicin.

2. The method of claim 1, wherein the compound and a chemotherapeutic agent are administered within one year of one another.

3. The method of claim 1, wherein the compound and a chemotherapeutic agent are administered within one month of one another.

4. The method of claim 1, wherein the compound and a chemotherapeutic agent or an immunotherapeutic agent are co-administered.

5. The method of claim 1, wherein the patient suffers from cancer.

6. The method of claim 5, wherein the cancer is selected from group consisting of a carcinoma, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer.

7. The method of claim 1, wherein the patient is an adult human.

8. A method of treating cancer in a patient in need thereof, comprising administering to the patient a chemotherapeutic agent that is paclitaxel, cyclophosphamide, or doxorubicin, or an immunotherapeutic agent and a compound A represented by formula:

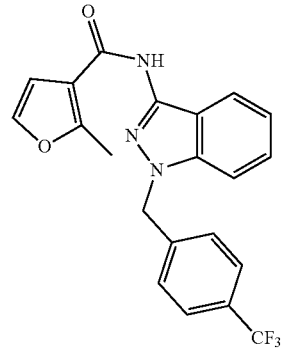

or tautomer thereof, and/or a pharmaceutically acceptable salt thereof.

9. The method of claim 8, wherein the patient is undergoing or about to undergo chemotherapy.

10. The method of claim 1, wherein the cancer is selected from group consisting of a carcinoma, lymphoma, sarcoma, melanoma, astrocytoma, mesothelioma, colon carcinoma, pancreatic carcinoma, esophageal carcinoma, stomach carcinoma, urinary carcinoma, bladder carcinoma, breast cancer, gastric cancer, leukemia, lung cancer, colon cancer, central nervous system cancer, ovarian cancer, renal cancer, prostate cancer, liver cancer, head and neck cancer, thyroid cancer, brain cancer, oral cancer, gallbladder cancer, ampulla cancer, biliary duct cancer, and larynx cancer.

11. The method of claim 10, wherein the cancer is selected from group consisting of neuroendocrine prostate cancer, activated B-cell subtype of diffuse large B-cell lymphoma, and triple-negative breast cancer.

\* \* \* \* \*